United States Patent [19]
Melton et al.

[11] Patent Number: 6,127,185
[45] Date of Patent: Oct. 3, 2000

[54] INSTRUMENT AND METHOD FOR MEASUREMENT OF STABILITY OF OILS

[75] Inventors: Sharon L. Melton, Rockford, Tenn.; Hung-Wei Lin, Marshall, Mich.

[73] Assignee: University of Tennessee Research Corporation, Knoxville, Tenn.

[21] Appl. No.: 09/305,902

[22] Filed: May 5, 1999

Related U.S. Application Data

[60] Provisional application No. 60/084,337, May 5, 1998.

[51] Int. Cl.[7] ........................... G01N 33/06; G01N 33/26; G01N 27/00
[52] U.S. Cl. ........................... 436/60; 73/53.02; 73/53.05; 324/71.1
[58] Field of Search ................................ 73/61.76, 53.02, 73/53.05, 61.77; 324/71.1, 439, 149; 702/19; 436/60; 422/82.01

[56] References Cited

U.S. PATENT DOCUMENTS

| 5,339,254 | 8/1994 | Matlock et al. ........................... 702/19 |
| 5,463,321 | 10/1995 | Matlock et al. ........................ 324/439 |
| 5,594,327 | 1/1997 | Sagredos et al. . | |

FOREIGN PATENT DOCUMENTS

| 60-003549 | 1/1985 | Japan ........................... G01N 33/03 |

*Primary Examiner*—Hezron Williams
*Assistant Examiner*—Jay L. Politzer
*Attorney, Agent, or Firm*—Nixon Peabody LLP

[57] ABSTRACT

The present invention relates to an instrument and methods for determining stability of oils and fats. The instrument includes a sample reaction vessel for containing a sample of an oil or fat, a moisturized gas source operably connected to the vessel for contacting a moisturized gas with the sample, a compound trap containing water operably connected to the vessel to contact the moisturized gas from the vessel with the water, and an automatic data acquisition and control system for monitoring the electrical conductivity of the water. The method is carried out by heating an oil or a fat, contacting the oil or fat with a moisturized gas, contacting the moisturized gas with water to form a trap solution, measuring the electrical conductivity of the trap solution, and determining the stability of the oil or fat.

39 Claims, 12 Drawing Sheets

Microfiche Appendix Included
(1 Microfiche, 42 Pages)

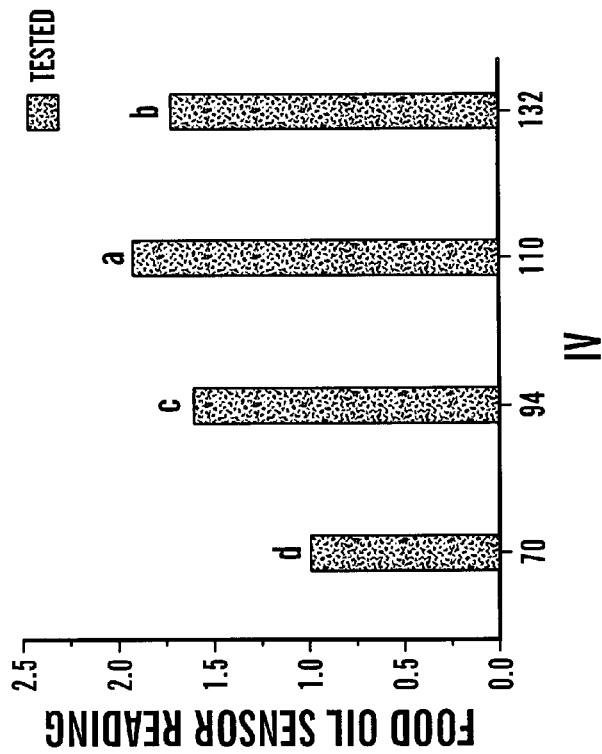
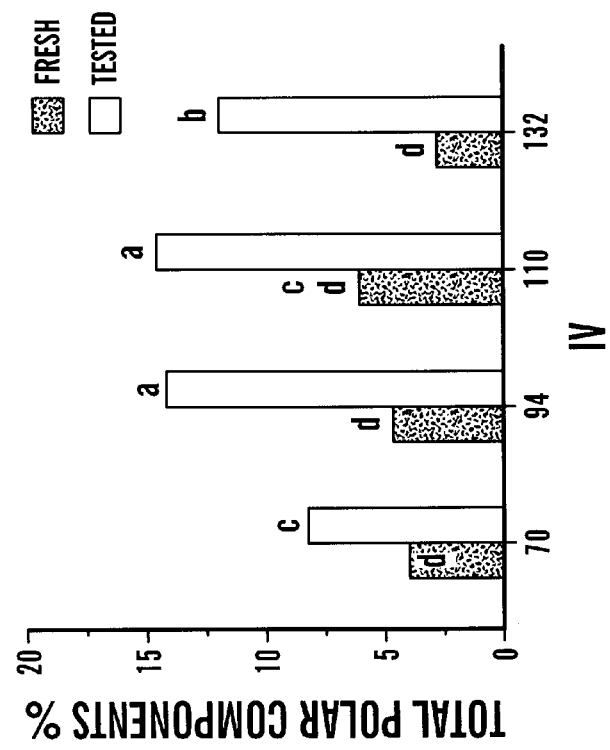
FIG. 6B
FIG. 6A

INSTRUMENT AND METHOD FOR MEASUREMENT OF STABILITY OF OILS This application claims the benefit of U.S. Provisional Patent Application Ser. No. 60/084,337, filed May 5, 1998.

Accompanying the present application is a Microfiche Appendix which contains 1 piece of microfiche having a total of 42 frames.

FIELD OF THE INVENTION

The present invention relatesto instruments and methods for measuring the stability of fats and oils, particularly consumable frying fats and oils.

BACKGROUND OF THE INVENTION

Introduction

Oxidative stability is an important parameter in determining quantitatively the deterioration rate of oils/fats (Laubli et al., "Determination of the Oxidative Stability of Fats and Oils: Comparison Between the Active Oxygen Method (AOCS Cd-12-57) and the Rancimat Method," *J. Am. Oil Chem. Soc.*, 63:792–795 (1986) ("Laubli"), which is hereby incorporated by reference). This measurement is crucial to both oil processors and users in specifying and examining the quality of their products. Deep-fat frying is one of the major oil applications in the United States (Stevenson et al., "Quality Control in the Use of Deep Frying Oil," *J. Am. Oil Chem. Soc.*, 61:1102–1108 (1984) ("Stevenson"), which is hereby incorporated by reference). In 1992, 38.4% of the total amount (2.4 million kg) of edible fats/oils consumed by Americans was used for frying and baking (USDA, "Oil Crops Situations and Outlook," October 1992. OCS-35. Dept. of Agriculture, Washington, D.C., which is hereby incorporated by reference). The edible oil industry has long sought for a rapid method to predict oxidative stability of fats/oils (Hill, "Comparisons: Measuring Oxidative Stability," *Inform*, 5:104–109 (1994) ("Hill"), which is hereby incorporated by reference); however, the most up-to-date instrument, the Oil Stability Instrument, requires many hours (10 to over 100) to complete an analysis. A rapid and accurate method for such a measurement is needed to provide both time efficiency and accurate results for the oil industry.

Oxidative decomposition of a fat/oil is detrimental to the acceptability and nutritional quality of foods (Nawar, "Lipid," Ch. 4. in *Food Chemistry*, $2^{nd}$ ed. O. R. Fennema (ed.), New York: Marcel Dekker, nc. ("Nawar"), which is hereby incorporated by reference). The major causes of the decomposition of a fat/oil are lipid hydrolysis and autoxidation (Arroyo et al., "High-Performance Size-Exclusion Chromatographic Studies on Polar components Formed in Sunflower Oil Used for Frying," *J. Am. Oil Chem. Soc.*, 69:557–563 (1992) ("Arroyo"); Frankel, "Recent Advances in Lipid Oxidation," *J. Sci. Food Agric.*, 54:495–511 (1991), which are hereby incorporated by reference). Many methods have been designed to measure the stability of a fat/oil based on the chemical or physical changes caused by the decomposition of the fat/oil. These methods such as the Active Oxygen Method ("AOM"), peroxide value ("PV"), thiobarbituric acid ("TBA") value, iodine value ("IV"), Shaal oven test, oxygen adsorption, chromatographic methods, and thermogravimetric analysis generally are used for evaluating the oxidative stability of a fat/oil (deMan et al., "Formation of short Chain Volatile Organic Acids in the Automated AOM Method," *J. Am. Oil Chem. Soc.*, 64:993–996 (1987) ("deMan"); Mikula et al., "Reaction Conditions for Measuring Oxidative Stability of Oils by Thermogravimetric Analysis," *J. Am. Oil Chem. Soc.*, 62:1694–1698 (1985) ("Mikula"), which is hereby incorporated by reference; Nawar). However, none of these tests are fully representative of oxidative stability of a fat/oil in terms of practical applications such as frying and cooking (Nawar). These tests are time consuming, labor intensive, and costly (Laubli). Therefor, a low-cost, rapid, accurate, and precise instrument for fat/oil oxidative stability measurement is needed.

AOM is the most popular method for determining the oxidative stability of a fat/oil (Hill). the oil sample (5 g) is heated to 98.7° C. and bubbled with a stream of dry air (140 mL/min flow rate). AOM value is determined by the time at which the oil sample reaches 100 meq of peroxide per kg of sample (AOCS Cd 12-57; AOCS, *Official and Tentative Methods of Analysis of the American Oil Chemists Society*, American Oil Chemists Society, Champaign, Ill. 1993), which is hereby incorporated by reference). The Rancimat method and Oil Stability Instrument are modified versions of AOM but use a higher temperature than that used by AOM. These instruments measure the increases of conductivity in water, caused by oxidation products such as volatile acids, to determine the oxidative stability (Hill; Laubli). AOM and its modified versions are either costly or time consuming.

Drozdowski et al., "A Rapid Instrumental Method for the Evaluation of the Stability of Fats," *J. Am. Oil Chem. Soc.*, 64:1008–1010 (1987) ("Drozdowski"), which is hereby incorporated by reference, analyzed the resistance to oxidation of oils by an oxygen adsorption instrument. They reported large variations in amounts of oxygen adsorption among 4 oil samples that had similar fatty acid composition, iodine value, and peroxide value. This method is rapid but expensive, and the accuracy of the results is questionable. Snyder et al., "Headspace Volatile Analysis to Evaluate Oxidative and Thermal Stability of Soybean Oil. Effect of Hydrogenation and Additives," *J. Am. Oil Chem. Soc.*, 62:1675–1679 (1986) ("Snyder"), which is hereby incorporated by reference, used gas chromatography ("GC") to measure the volatiles in the headspace of heated oil samples. They reported that the concentrations of volatiles formed in the headspace had good correlations with oil stability. However, their method needs sophisticated instrumentation and cannot handle a large volume of samples. Garcia-Mesa et al., "Factors Affecting the Gravimetric Determination of the Oxidative Stability of Oils," *J. Am. Oil Chem. Soc.*, 70:245–247 (1993) ("Garcia-Mesa"), which is hereby incorporated by reference, used a gravimetric method to determine the oxidative stability of oil; the weight gains by oil samples heated in the hot air oven were positively correlated ($P<0.05$) with peroxide values. This method requires intensive work; the samples must be weighed frequently and each test requires at least 20 hr.

In addition to the disadvantages of low time efficiency and high cost, the methods mentioned above overlook the hydrolysis occurring in fats/oils in a frying system. An ideal method for evaluating the stability of a fat/oil under frying conditions should look into all chemical reactions occurring during that process. For example, the frying oil is exposed to air, moisture, and high temperatures (160–190° C.). The moisture causes hydrolysis of triglycerides, producing free fatty acids and mono- and diglycerides. The air, absorbed by the oil, initiates oxidative decomposition. High frying temperatures (160–190° C.) can trigger the thermal decomposition in the fats/oils (Arroyo; Boskou, "Stability of Frying Oils," Varela, eds., *Frying of Food: Principles, Changes, New Approaches*, Chichester, England: Ellis Horwood Ltd., ch. 13, pp. 174–182 (1988) ("Boskou"), which is hereby incorporated by reference). Frying fats come into contact with moisture, which is released from food during frying. While this moisture can increase in free fatty acids in the frying oils, it also aids in removing other oxidative degradation products from the oil via steam distillation. This stem distillation effect actually prolongs the useful life of a frying fat. All these reactions occurring in fats/oils during frying should be taken into consideration when building a reliable instrument for measuring oil oxidative stability.

A prototype instrument 20 for measuring frying oil stability made in accordance with the present invention was developed in The University of Tennessee Food Science and Technology department. The instrument 20 permits oxidation of fats at frying temperatures while moisturized air is bubbled through the hot oil. This computer-based instrument 20 is similar to the Oil Stability Instrument in that it measures the increase in conductivity of water-trapped decomposition products from the oil, but it has several unique differences, which are further discussed below.

Literature Review

1. Chemical changes in the Lipid During Frying

Lipid oxidation is preceded primarily by an autoxidation mechanism and initiated by free radicals. The production of free radicals may occur by thermolysis (thermal dissociation), hydroperoxide decomposition, metal catalysis, and exposure to light (photolysis) with or without initiation by photosensitizers. Autoxidation undergoes a chain mechanism of three stages and includes initiation, propagation, and termination. Hydroperoxides are primary products of lipid oxidation. Due to their unstable nature, hydroperoxides readily break down and produce free radicals, alcohols, aldehydes, and ketones; these decomposition compounds can undergo further oxidation to produce carboxylic acids or they may polymerize (Frankel, "Lipid Oxidation," *Lipid Res.*, 19:1–22 (1980), which is hereby incorporated by reference; Laubli; Lin, "Flavor and Stability of Potato Chips Fried in Canola, High Oleic Sunflower, Sunflower, and Cottenseed Oils," *Master's Thesis*, the University of Tennessee, Knoxville (1983) ("Lin"), which is hereby incorporated by reference).

A variety of chemical reactions occur in the oil/fat during the frying process in which the fat/oil is subjected to air, high temperature, and steam. The air incorporated into the frying media is an oxygen source for oxidation and triggers the formation of free radicals. Steam causes hydrolysis of triglycerides (Cuesta et al., "Thermoxidative and Hydrolytic Changes in Sunflower Oil Used in Frying With a Fast Turnover of Fresh Oil," *J. Am. Oil Chem. Soc.*, 70:1069–1073 (1993) ("Cuesta"), which is hereby incorporated by reference). A high frying temperature provides energy to favor chemical reactions and causes thermolysis. In general, unsaturated fatty acids in oil/fat undergo the autoxidation reaction by a free radical mechanism. However, even saturated fats may undergo thermal decomposition at frying temperatures (Frank et al., "Automatic Determination of Oxidation Stability of Oil and Fatty Products," *Food Technol.*, 35:71–76 (1982), which is hereby incorporated by reference; Lin; Paquette et al., "The Mechanisms of Lipid Autoxidation. I. Primary Oxidation Products," *Can. Inst. Food Sci. Technol.*, 18:112–118 (1985), which is hereby incorporated by reference). In addition to the decomposition compounds formed during lipid oxidation, hydrolysis of triglycerides also causes formation of free fatty acids, glycerol, and mono- and di-glycerides (Cuesta).

In general, decomposition compounds of oil/fat oxidation are categorized into volatile decomposition products ("VDP") and non-volatile decomposition products ("NVDP"). These compounds usually are used as the indicators of oil/fat deterioration. Many factors, such as type of frying fat, type of food, conditions of operation, and type of fryer can cause variations in the physical and chemical changes occurring in frying fat during deep-fat frying (Fritsch, "Measurement of Frying Fat Deterioration: A Brief Review," *J. Am. Oil Chem. Soc.*, 58:272–274 (1981) ("Fritsch"), which is hereby incorporated by reference).

Cuesta used refined sunflower oil to fry potatoes continuously with rapid turnover rate. They discovered more thermoxidative than hydrolytic reactions during deep-fat frying. Total polar components ("TPC") level was used as a representative measurement of the total alterations of the oil. Oxidized, dimeric, and polymeric triglycerides indicated thermoxidative alteration of the oil. Free fatty acids plus diglycerides represented the major products of hydrolytic reaction. The relationship between TPC levels and total thermoxidative alteration in the frying oil or numbers of times used for frying could be explained by third order polynomial regression equations, in which the regression coefficients were 0.9957 and 0.9949, respectively. TPC level and polymer content increased rapidly during the earlier frying stage then tended to level off during the latter stage of frying. The diglyceride content and total hydrolytic modifications (diglycerides plus free fatty acids) in the frying oil increased slightly as the number of times the oil was used for frying increased, but the magnitudes of the increases with increasing number of times that the oil was used for frying were not statistically significant. The relationship between free fatty acid content and the number of frying times was irrelevant because free fatty acids were partially lost to the atmosphere during frying. Other researchers also noted that the linoleic acid content of the frying oil decreased while oleic, stearic, and palmitic acids remained unaltered after the sunflower oil was used for frying potatoes for 15 times (Arroyo; Cuesta; Sánchez-Muniz et al., "Sunflower Oil Used for Frying: Combination of Column, Gas and High-Performance Size-Exclusion Chromatography for its Evaluation," *J. Am. Oil Chem. Soc.*, 70:235–240 (1993) ("Sánchez-Muniz"), which is hereby incorporated by reference).

Farag et al, "Comparative Study on the Deterioration of Oils by Microwave and Conventional Heating," *J. Food Prot.*, 55:722–727 (1992), which is hereby incorporated by reference, heated oil by microwave and deep-fat frying. They discovered a significant decrease in levels of oleic and linoleic acids and an increase in the amount of palmitic acid in heated refined cottonseed oil. They explained that the heating process may have caused an abstraction of a hydrogen atom from the active methylene group adjacent to the carboxyl group to produce free radicals, followed by oxidative degradation to produce shorter chain fatty acids such as palmitic and acetic acids.

Smith et al., "changes in Physical and Chemical Properties of Shortenings Used for Commercial Deep-Fat Frying," *J. Am. Oil Chem. Soc.* 63:1017–1023 (1986) ("Smith"), which is hereby incorporated by reference, surveyed the quality of the oils used for commercial deep-fat frying. A variety of oil quality indicators such as free fatty acids ("FFA"), TPC, fatty acid profile, and dielectric constant (measured as the Food Oil Sensor, or FOS, reading) were determined and compared with the number of frying times of the samples. They observed marked increases of dielectric measurements, TPC, and FFA in the used oil samples. The greatest change in fatty acid profiles occurred in the trans-C18:1 fatty acid level, which decreased over 40%. Stearic acid (C18:0) concentration also decreased during frying while level of C16:0 increased. Increase of C18:1 and C18:2 over frying times was not due to the effects of frying but to an exchange of the frying fat with the lipid in the foods.

2. Effects of Antioxidant on Retardation of Lipid Oxidation

Antioxidants retard the deterioration of lipid oxidation by interfering with free radical formation or quenching a pro-oxidant such as singlet oxygen. Antioxidants such as butylated hydroxyanisole ("BHA"), butylated hydroxytoluene ("BHT"), butylated hydroquinone ("TBHQ"), and propyl gallate interfere with free radicals by a chain-breaking mechanism during initiation or propagation stage of lipid oxidation. The antioxidant compounds mentioned above generally lose their efficiency at elevated temperatures by homolytic decomposition of hydroperoxides or by reaction with oxygen (Frankel, "Lipid Oxidation," *Lipid Res.*, 19:1–22 (1980), which is hereby incorporated by reference). Tocopherols have been reported as free radical scavengers. The ($\alpha$-tocopherol is known for quenching singlet oxygen, considered as a pro-oxidant formed by photochemical sensitizers such as chlorophylls. The amounts of $\alpha$-, $\beta$-, $\gamma$-, and $\delta$-tocopherols present in soybean oil are reported as 91–118, 21–43, 640–795, and 325–406 ppm, respectively. The optimum concentration of total tocopherols for retarding lipid oxidation in a soybean oil is between 400 and 600 ppm (Jung et al., "Effects of $\alpha$-, $\gamma$-, and $\delta$-Tocopherol on Oxidative Stability of Soybean Oil," *J. Food Sci.*, 55:1464–1465 (1990) ("Jung I"); Jung et al., "$\alpha$-, $\gamma$-, and $\delta$-Tocopherol Effects on Chlorophyll Photosensitized Oxidation of Soybean Oil," *J. Am. Oil Chem. Soc.*, 56:807–810, 815 (1991) ("Jung II"); Weiss, *Foods Oils and Their Uses*, $2^{nd}$ Ed., Westport, Conn.: AVI Publishing Co., Inc. (1983) ("Weiss"), which are hereby incorporated by reference).

Asap et al., "Effect on TBHQ on Quality Characteristics of RBD Olein During Frying," *J. Am. Oil Chem. Soc.*, 63:1169–1175 (1986), which is hereby incorporated by referenced, examined the effect of TBHQ on the quality characteristics, including TPC, iodine value ("IV"), and fatty acid profile, of refined, bleached, and deodorized ("RBID") palm olein during frying. Treatments included an initial 200 ppm of TBHQ with or without replenishment of the loss of TBHQ during each day of frying. Results were compared to those of a control sample. The authors concluded that the addition of TBHQ reduced the levels of TPC and polymers in the oil, decreased the rate of change in iodine value ("IV") and dielectric constant, and decreased the rate of C18:2 oxidation. When the loss of TBHQ during frying was replenished each day, the reduction rates of the undesirable changes were even more profound than without the replenishment of TBHQ loss.

Augustin et al., "Efficacy of the Antioxidants BHA and BHT in Palm Oleic During Heating and Frying," *J. Am. Oil Chem. Soc.*, 60:1520–1523 (1983), which is hereby incorporated by referenced, assessed the effectiveness of BHA and BHT in retarding the deterioration of RBD palm olein during static heating (180° C.) and frying of potato chips; the effectiveness was assessed by peroxide value ("PV"), anisidine value, FFA level, IV, fatty acid profile, and dienoic acid level. In general, PV, anisidine value, FFA, and dienoic acids increased over the period of heating or frying while the IV and ratio of C18:2/C16:0 decreased. Heated oil had lower rates of the changes of the above measurements than did the oil used for frying. The authors noted also that BHA was more effective than BHT in retarding oil oxidation during static heating, whereas, both BHA and BHT became ineffective for antioxidative function during intermittent frying of potato chips.

Jung I examined the effectiveness of $\alpha$-, $\gamma$-, and $\delta$-tocopherons at various concentrations on oxidative stability of soybean oil stored in the dark at 55° C. PV and headspace oxygen consumption were used to measure the effectiveness. Tocopherols had antioxidative effects at the lower concentrations but acted as pro-oxidants at higher concentrations. The optimum concentrations of ($\alpha$-, $\gamma$-, and $\delta$-tocopherol for antioxidative effect on purified soybean oil were 100, 250, and 500 ppm, respectively. In other words, under these conditions, $\alpha$-tocopherol was more effective in protecting soybean oil from oxidation than $\gamma$- and $\delta$-tocopherol. Jung II used a similar experimental model to assess the effects of $\alpha$-, $\gamma$-, and $\delta$-tocopherol on chlorophyll b-photosensitized oxidation of soybean oil. They observed that as the concentrations of tocopherols increased, PV decreased and headspace oxygen increased. The $\alpha$-tocopherol showed highest and $\gamma$-tocopherol showed lowest antioxidant effects on photosensitized lipid oxidation. Jung II confirmed that $\alpha$-tocopherol quenched singlet oxygen to reduce photosensitized lipid oxidation.

3. Measurements of Fat/Oil Oxidative Stability

Oxidative stability is defined as quantitative measurement of the susceptibility of an oil to autoxidative breakdown. The edible oil industry has long looked for a rapid analytical method to measure the oxidative stability of oils/fats. Active Oxygen Method ("AOM") is the most widely used test. The modified versions of AOM such as the Rancimat and Oil Stability Instrument methods are commonly used in the oil industry due to their convenience, even though their results are not consistent with the AOM values. Three methods based on oxygen consumption or oxygen intake are commonly employed; these methods include gravimetric measurement and measurement of oxygen consumption or pressure change in the headspace of a closed oil container. Gas chromatographic ("GC") methods determine the oxidative stability of oils by examining the concentration changes over time of certain volatile compounds in the headspace of a closed oil sampler held at an elevated temperature. A thin-film method speeds up the oxidative stability measurement by exposing an oil sample to ultraviolet ("UV") radiation; PV change in the oil over time is used to interpret the oxidative stability of oil (Gordon et al., "Assessment of Thin-Film Oxidation with Ultraviolet Irradiation for Predicting the Oxidative Stability of Edible Oils," *J. Am. Oil Chem. Soc.*, 71:1309–1313 (1994) ("Gordon"), which is hereby incorporated by reference; Hill).

Active Oxygen Method (AOM)

AOM measures the time in hours required for a sample of fat/oil to attain a predetermined peroxide value (PV 100 meq/kg) under specific conditions. The oil/fat sample (5 g) is bubbled with dried air at a flow rate of 140 mL/min at a temperature of 98.7° C. (AOCS, *Official and Tentative Methods of Analysis of the American Oil Chemists Society*, American Oil Chemists Society, Champaign, Ill. 1993); Laubli). The progress of oxidation is monitored by periodic examination of PV in the testing fat/oil. This method is time-consuming, labor intensive, and cost inefficient (deMan).

The Rancimat and Oil Stability Instrument

Rancimat and Oil Stability Instrument are two modified and automated versions of AOM but differ in several ways. Both methods measure the conductivity in deionized water as it increases due to the absorption of volatile acids and the decomposed products of fat/oil oxidation. Increasing conductivity is an indication of peroxide breakdown that occurs at the same time as PV increases (AOCS, *Official and Tentative Methods of Analysis of the American Oil Chemists*

*Society*, American Oil Chemists Society, Champaign, Ill. 1993); Laubli).

The end-points of the automated AOM are indicated by fast increases in conductivity in the water solutions due to the rapid production of volatile fatty acids by the oils at the end of the induction period. The volatile fatty acids produced by several oils include formic, acetic, propionic, butyric, valeric, and caproic acids, among which formic acid is the major component and acetic and caproic acids are present in significant amounts. Production of formic acid is due mainly to peroxidation of aldehydes during autoxidation of oil. The increase in the formic acid concentration in the water solutions through which gas bubbled through the oil exits is responsible for the increase in their conductivity (deMan).

The Oil Stability Instrument uses a similar instrumental design as the Rancimat to measure oxidation stability of oils but is modified in many areas. The Rancimat contains only six sample holders but the Oil Stability Instrument can handle twenty-four at one time. The Rancimat has only one aluminum heating block while the Oil Stability Instrument has two, which can be set at two different temperatures. The Rancimat uses sophisticated glass joints which are replaced with rubber tubing or disposable glass by the Oil Stability Instrument. Any sample in the Oil Stability Instrument can be started and stopped at any time; this is impossible with the Rancimat. Data in the Oil Stability Instrument can be stored and handled by a personal computer, while the Rancimat is limited to its electronic recorder which stores only a set of non-transferrable data. Basically, the Oil Stability Instrument has the same application and precision as the Rancimat method (Hill).

Laubli analyzed oil stability of different oils at 100, 110, and 120° C. by AOM and Rancimat methods. The results of the Rancimat method were correlated highly with those of the AOM (r=0.987) at all temperatures. The temperature coefficient of the induction time for a temperature change of 10° C. ranged between 1.8 and 2.1 with a regression coefficient better than 0.99 among all the different oils.

Hasenhuettl et al., "Temperature Effects on the Determination of Oxidative Stability with the Metrohm Rancimat," *J. Am. Oil Chem. Soc.*, 69:525–527 (1992) ("Hasenhuettl"), which is hereby incorporated by reference, observed that the logarithm of induction time of different oils analyzed by the Rancimat method was correlated highly with reaction temperature up to 140° C. The conductivity curve of an oil sample tested by the Rancimat method at a reaction temperature of 150° C. appeared to be inverted concave downward; this caused difficulty in placing the tangent lines. The coefficient of variation ("CV") of oxidation stability index tested by the Rancimat method was 2.3% among 6 tubes on a single test run and 10.4% among 8 different runs test at a reaction temperature of 120° C. They noted that temperature variations in heating blocks can cause variations in the reported oil stability index. A collaborative study of reproducibility of the Rancimat method showed an 11.3% CV with a reaction temperature of 110° C. (Hill).

Volatile antioxidants are ineffective at typical Oil Stability Instrument and Rancimat operation temperatures. Reynhout, "The Effect of Temperature on the Induction Time of a stabilized Oil," *J. Am. Oil Chem. Soc.*, 68:983–984 (1991) ("Reynhout"), which is hereby incorporated by reference, used the Rancimat method to measure the induction time of oil treated with different types of antioxidants, including BHT, BHA, TBHQ, Herbalox (a rosemary extract), and tocopherols. Soybean oil was treated with 200 ppm of synthetic antioxidant or 400 ppm natural antioxidant. The induction time of the oil treated with BHT, BHA, and tocopherols did not appear to be different than that of the control. The oil treated with TBHQ had a longer induction time in comparison to the other treatments at different temperatures. The induction time of oil treated with Herbalox was higher than those of other treatments except for the oil treated with TBHQ. Use of the Rancimat method at 80° C. to assess the effectiveness of volatile antioxidants in oil/fats improved the accuracy of the results. However, the induction times of an oil sample tested by the Rancimat at 80° C. are 2 to 6 times longer than that tested at 100° C. (Gordon).

Both the Rancimat and Oil Stability Instrument have limitations when analyzing as oil such as olive oil with a high AOM value for which the reported AOM value is more than 200 hr. During a long analysis procedure, the receiving water in the Rancimat or Oil Stability Instrument tends to evaporate and limits the accuracy of the instruments. Both Rancimat and Oil Stability Instrument methods use different conditions than those specified by the official AOCS method; this creates a wide variability in their reported AOM time (Hill).

Schaal Oven Test

The Schaal oven test measures the induction time both chemically (PV greatly increases) and organoleptically (the time where the first sign of rancidity occurs) in order to measure the oxidative stability of oil. In the Schaal oven test, a 100 g sample of oil or food containing oil is sealed in a bottle and placed in a dry cabinet at 65° C. The sample is checked periodically by both organoleptic observation until the first sign of rancid odor is noticed and PV increases; this time is determined as the induction time (Hill).

Thin Film Ultraviolet Irradiation Method

Gordon predicted the oxidative stability of edible oils by a thin-film oxidation method accelerated by ultraviolet ("UV") irradiation. They compared the induction time of edible oils analyzed by thin-film oxidation with ultraviolet irradiation and the Rancimat methods. The GC-headspace volatiles, PVs, and conjugated dienes in the oil samples increased as the time of their exposure to the UV light increased; the induction time of the thin-film oxidation method is determined by the mean of induction time obtained by those three measurements. The mean induction time of oil samples obtained by the thin-film oxidation method were highly correlated (r=0.99) with the those tested by the Rancimat method at both 80° C. and 100° C., except for cocoa butter. Cocoa butter may contain more carotenes and chlorophyll than the refined oils, causing acceleration of the oil oxidation in the presence of light. They noted that the Rancimat test gives the order of stability as cocoa butter>>olive oil>rapeseed oil>corn oil>soybean oil>sunflower oil>safflower oil. The oxidative stability of oil samples as measured by the thin film UV irradiation method was in the order of cocoa butter>>rapeseed oil~olive oil>soybean oil>corn oil~safflower~sunflower oil.

Thermogravimetric ("TGA") Method

Oxidation of fats/oils can be indicated by the weight change of the fats/oils in a hot air oven. TGA can be measured isothermally or dynamically under a stream of flowing hot air. Many factors, such as surface to volume ratio, temperature of the oven, air flow rate, method of sampling, and sample size affect the accuracy of the TGA method (Garcia-Mesa; Mikula). However, neither the accuracy nor reproducibility of the TGA method was reported in these articles.

Mikula analyzed the oxidative stability of soybean oils by the TGA method with a highly sensitive electronic balance.

They noted that a typical thermogravimetric curve of a soybean oil sample analyzed isothermally at 150° C. consisted of three phases. The first phase was the induction period ("IP"), during which only minimal weight change was observed. Rapid weight increases occurred in the second phase ("Phase II") of this analysis. Upon reaching the maximum weight gain, the weight of the testing oil began decreasing ("Phase III"). The IP, measuring the resistance of the oil to oxidation, is determined by extrapolating the baseline and upward portion of the curve until they intersect. Using the same size of platinum sample pan, IP decreased with decreased sample weight because the smaller sample exposed a greater surface area per volume than that with a larger weight. The maximum slopes of upward and downward curves were called $R_{wg}$ and $R_{wl}$, respectively. The $R_{wg}/R_{wl}$ ratio increased with sample weight. They examined the effects that temperatures between 80 and 190° C. imposed on the results of the TGA test. They observed that the IP was inversely proportional to the reaction temperature. The IP had a linear relationship with the reciprocals of temperatures between 80 and 150° C., giving an activation energy of 21 kcal/mole. The activation energy changed at temperatures above 150° C. After they compared the results between isothermal and dynamic TGA, they concluded that the TGA obtained isothermally at 150° C. was more suitable than dynamic TGA for rapid and routine evaluation of oxidative stability of freshly processed oils.

Garcia-Mesa evaluated the factors affecting the gravimetric determination of the oxidative stability of oils including reaction temperature and sample surface-to-volume ratio. They presented a different model: the weight of the oil sample increased with a corresponding increase of PV until the degradation of peroxides began. After the degradation of peroxides further weight gain of the tested oil was only slight. An increase in ether oven temperature or surface/volume ratio accelerated the oxidation process.

The precision of the gravimetric test was only legitimate up to an oven temperature of 100° C.; the results of the test were not reproducible at an oven temperature greater than 100° C. Limitations of this test are that discontinuous heating of the sample may affect the reproducibility of the results; the method involves intensive human work, and working conditions, including sample size, dimensions of container, and oven temperature, may cause variations in the results (Garcia-Mesa).

Oxygen Absorption Method

Drozdowski devised a rapid method to evaluate the oxidation stability of oils/fats by measuring the consumption of headspace oxygen based on the pressure difference on a manostatic device. They found that oxygen consumption in the tested oil increased as the PV of the oil increased up to the point where peroxides began degrading. Increase in the reaction vessel temperature reduced the induction time of the tested oil. The initial oil with higher PV had a shorter induction time than those with lower initial PVs. However, they analyzed a set of four low erucic acid rapeseed oils ("LEAR") with similar IVs and PVs. The results of the rapid instrumental method showed significant differences in the oxygen absorption curves among the four oils and indicated that those oils were different in oxidation stability.

Gas Chromatographic ("GC") Methods

As mentioned in the previous section, Jung II examined the oxygen consumption from the headspace of an oil sample over storage time by GC to determine the antioxidative effects of tocopherols on lipid oxidation (Jung I; Jung II). Examination of fatty acid profiles in an oil sample by GC is commonly used to determined the oxidative stability of an oil/fat due to oil formula, processing and storage conditions, or additive treatment (Cuesta; Lin; Smith). These GC methods can be rather complex and time consuming (Hill).

Snyder measured total volatiles in vegetable oils stored at 60° C. for 0, 8, and 16 days, using GC-headspace analysis; the results were compared to the oxidation levels in the oil samples as indicated by PV. Total volatiles were determined by the total peak areas of volatile components on a GC chromatogram. They noted that the total volatiles for each oil tested increased with storage time at 60° C. following a trend similar to PV. The production of total volatile compounds during storage of the oils was related to their fatty acid compositions. Safflower, sunflower, corn, and cottonseed oil, which have the highest amounts of linoleic acid among all oil samples, formed more volatile compounds than canola, soybean, and olive oils, which have lower levels of linoleic acid than the previously listed oils. Pentane, hexanal, and 2-pentenal, formed from oxidative decomposition of linoleic acid, showed the greatest increases during storage. The 2,4-heptadienals, oxidative decomposition products of linolenic acid and found in soybean and canola oils, increased after extended storage. VDP such as heptanal, octanal, and nonanal produced by oxidation of oleic acid did not increase between 8 and 16 days of storage.

4. Measurements of Frying Fat Deterioration

Measurements for frying fat deterioration usually are based on the physical or chemical changes of the frying oils/fats during deep-fat frying. These measurements include free fatty acid level, peroxide value, iodine value, diene concentration, refractive index, viscosity, color, Kreis test, anisidine value, levels of carbonyls, non-urea-adduct forming esters, oxirane compounds, petroleum ether-insoluble oxidized fatty acids, total polar components, and dielectric constant. The factors affecting the rate of fat deterioration during deep-fat frying are complex and yield neither a single measurement procedure leading to reliable results in all situations nor an ideal chemical method correlating well with changes in organoleptic properties of oxidized lipids throughout the entire course of autoxidation (Fritsch; Gray, "Measurement of Lipid Oxidation: A Review," *J. Am. Oil Chem. Soc.*, 55:539–546 (1978) ("Gray"), which is hereby incorporated by reference).

During deep-fat frying, a fat/oil is exposed to air, moisture, and high temperatures. The moisture causes hydrolysis of triglycerides and produces free fatty acids and mono- and diglycerides. The air, incorporated into the fat/oil, initiates an oxidative reaction and induces the formation of hydroperoxides, conjugated dienic acids, epoxides, hydroxides, and ketones on one or more of the fatty acid chains of the triglyceride. The oxidized triglyceride may continue breaking down into smaller fragments or may undergo polymerization with other oxidation products into dimeric and higher polymeric triglycerides. High frying and cooking temperatures (170–200° C.) also trigger the thermal decomposition and polymerization in the fats/oils (Arroyo; Boskou; White, "Methods for Measuring Changes in Deep-Fat Frying Oils," *Food Technol.*, 45:75–80 (1991), which is hereby incorporated by reference). these reactions cause changes of the functional, sensory, and nutritional properties in frying fats and may lead to a point where the quality of fried foods is no longer acceptable and where frying fats should be discarded.

As mentioned in the previous section, decomposition compounds of oil/fat oxidation are categorized into VDP and NVDP; these compounds usually are used as the indicators of oil/fat deterioration. Chang et al., "Chemical Reactions Involved in the Deep-Fat of Frying Foods," *J. Am. Oil*

*Chem. Soc.,* 55:718–727 (1978), which is hereby incorporated by reference, measured the VDP collected from a simulated deep-fat frying system using corn oil, hydrogenated cottonseed oil, triolein, and triolein by a GC method. A total of 220 compounds were identified. Because measurement of VDP is very time-consuming and complicated, little additional work has been conducted with VDP since the 1970s. The formation and accumulation of NVDP change the physical and chemical properties of frying fat/oil. Physical changes include increases in viscosity, color, dielectric constant, and foaming, and a decrease in smoke point. Chemical changes involve increases in FFA, PV, conjugated dienoic acids, TPC, polymers, carbonyl value, hydroxyl content, saponification value, and a decrease in unsaturation (Fritsch; White). Many factors such as type of fat, type of food, conditions of operation and dryer can cause variations in the physical and chemical changes occurring in frying fat during deep-fat frying; the variations make it difficult to select any standard to interpret the results across different types of oils and frying applications (Fritsch). However, no single test can be used universally to determine the point where a frying fat needs to be discarded (Melton et al., "Review of Stability Measurements for Frying Oils and Fried Food Flavor," *J. Am. Oil Chem. Soc.,* 71:1301–1308 (1994) ("Melton"), which is hereby incorporated by reference).

Cut-off levels are the maximum and minimum acceptable values for the fat to be considered as good quality. Examples include a 1% level of petroleum ether-insoluble oxidized fatty acids or a smoke point of 170° C. Alternatively, a TPC level of 27%, corresponding to 1% level of petroleum ether-insoluble oxidized fatty acids, also is commonly accepted by the edible oil industry as a critical indicator for the quality control of frying oil (Fritsch).

Peroxide Value

Hydroperoxides are the primary products of lipid oxidation and generally are referred to as peroxides. The concentration of peroxides may be used as an assessment of the degree of lipid oxidation. However, hydroperoxides are very unstable and sensitive to temperature changes; they readily decompose into carbonyl and hydroxyl compounds. PV of an oil sample continues to increase after the sample is removed from the fryer. The PV method is limited in that it measures only the initial stage of oxidation; the PV increases initially then decreases over the entire course of oxidation (Gray).

Thiobarbituric Acid ("TBA") Test

The TBA method is based on the color formation between two TBA molecules and one molecule of malonaldehyde. Malonaldehyde is a secondary product of oxidation of polyunsaturated fatty acids with two or more double bonds. Formation of malonaldehyde, is achieved by cyclization of the peroxide group and the $\beta$ and $\gamma$ double bonds next to the peroxide group. Oxidized lipid lacking polyunsaturated fatty acids such as linoleate forms no color reaction with TBA even at a PV of 2000 or greater (Gray).

Non-volatile Carbonyl Compounds

Carbonyl compounds, which are degraded compounds from hydroperoxides, are secondary products of lipid oxidation. Non-volatile carbonyl compounds are probable flavor precursors to more volatile compounds, but they yield no direct contribution to the flavor. The most reliable method for measuring non-volatile carbonyl compounds is based on the reaction of saturated and unsaturated aldehydes with anisidine (p-methoxyaniline). A high correlation between the anisidine values of salad oils and their flavor scores has been reported (Gray). A multiple correlation showed a correlation coefficient of 0.81 between flavor scores, anisidine values, and peroxide values; however, this method, as the peroxide value, is limited to measuring the early stage of lipid oxidation.

Oxirane Determination

Oxirane compounds, containing $\alpha$-epoxy groups, are formed during oxidation of unsaturated lipid material. The ($\alpha$-epoxy groups are measured by the consumption of a halogen by a fat sample reacting with a known excess amount of halogen in a suitable solvent. This method is reported to be particularly suitable for determination of epoxides in heated fats in which the oxirane level is less than 0.1% (Gray).

Conjugated Diene Method

Oxidation of polyunsaturated fatty acids causes formation of conjugated unsaturated fatty acids which exhibit strong absorption from 230 to 375 nm. Conjugated diene and triene unsaturation have maximum absorptions at 234 nm and 268 nm, respectively. Increase in the absorption at 234 nm usually is used to indicate the degree of oxidation of a fat sample containing linoleate or a more highly unsaturated fatty acid. The magnitude of the UV absorption is not related to the degree of oxidation because different fatty acids vary in their absorption at 234 nm. However, the change of absorption at 234 nm of a given fat sample can be used as a relative measure of oxidation. This test is most useful in measuring heat abuse of polyunsaturated oils, but is less applicable to fat containing few unsaturates (Gray; Peled et al., "Effect of Water and BHT on Stability of Cottonseed Oil During Frying," *J. Sci. Food Agric.,* 26:1655–1659 (1975), which is hereby incorporated by reference).

Refractometry

Refractive indices of fats/oils increase upon autoxidation. The change in refractive index of a fat sample follows the three stages of fat/oil oxidation. During the induction period, the peroxide formation is low and the refractive index remains constant. In the secondary stage, the refractive index increases sharply as the peroxide value increases before reaching the maximum point. The development of conjugated unsaturation contributes to the increase in refractive index during this stage of oxidation. In the tertiary stage, where the peroxides decompose, the refractive index continues to increase at a steady rate, which is less than that in the secondary stage. Polymerization of partially oxidized fats is responsible for this increase in refractive index during the tertiary stage of oxidation (Arya et al., "Refractive Index as an Objective Method for Evaluation of Rancidity in Edible Oils and Fats," *J. Am. Oil Chem. Soc.,* 46:28–30 (1969), which is hereby incorporated by reference).

Total Polar Components

Determination of TPC has proved to be accurate, simple, and reproducible (Dobarganes et al., "High Performance Size Exclusion Chromatography of Polar Compounds in Heated and Non-Heated Fats," *Fat Sci. Technol.,* 90:308–311 (1988), which is hereby incorporated by reference). Total polar materials are determined by dissolving a weighed amount of fat (2.5 g) in light petroleum ether:diethyl ether (87:13) and passing it through a silica gel column that absorbs the polar compounds. After evaporation of the eluted solvent, the nonpolar fat is weighted and the total polar material is estimated by difference. A level of 27% TPC has been suggested as the upper limit to discard a frying fat (Paradis et al., "Evaluation of New Methods for Assessment of Used Frying Oils," *J. Food Sci.,* 46:449–451 (1981); Paradis et al., "A Gas Chromatography Method for the Assessment of Used Frying Oils: Comparison With Other Methods," *J. Am. Oil Chem. Soc.,* 58:635–638 (1981) ("Paradis"), which are hereby incorporated by reference).

Fatty Acid Analysis and 18:2/16:0 Ratio

Thompson et al., "Lipid Changes in French Fries and heated Oils During Commercial Deep Frying and Their Nutritional and Toxicological Implications," Can. Inst. Food Sci. Technol. J., 16:246–253 (1983), which is hereby incorporated by reference, found that a lightly hydrogenated frying oil, after 100 hr of frying, had 50% less total linoienic and linoleic acids than the fresh oil. Thus, the relative amount of saturated fatty acids increased. Miller et al., "High-Temperature Stabilities of Low-Linolenate, High-Stearate and Common Soybean Oils," J. Am. Oil Chem. Soc., 65:1324–1327 (1988), which is hereby incorporated by reference, also reported a decrease in linoleic and linolenic fatty acids and an increase in relative amounts of saturated fatty acids in soybean oils heated at 180° C. for 40 hr.

Gas Chromatographic Method

Paradis evaluated the quality of used frying oil by measuring the dimeric polymer content in the oil sample with a GC. Corn oil was heated at 185° C. for various periods of time followed by chemical analysis. Percentage of dimeric polymers in the total triglycerides, total polar compounds, and dielectric constant of the corn oil increased over the heating time but no correlation among those three methods was tested. The GC method had the highest correlation coefficient between the values and heating times among the three methods.

High Performance Size-exclusion Chromatographic Method ("HPSEC")

White et al., "A High Performance Size-Exclusion Chromatographic method for Evaluating Heated Oils," J. Am. Oil Chem. Soc., 63:914–920 (1986) ("White"), which is hereby incorporated by reference, measured the changes of polymer content in heated oils by the HPSEC method to determine the quality of frying oils. Four peaks were found in the heated soybean oils by HPSEC. Peaks 1, 2, 3, and 4 were referred to as triglycerides ("TG") and fatty acids, dimeric TG, tetrameric TG, and polymers larger than tetrameric TG, respectively. Only peaks 1 and 2 were present in unheated oils. Areas of peaks 1, 2, and 3 behaved less predictably than that of peak 4. The area of peak 4 increased continuously over entire heating periods while the areas of peaks 1, 2, and 3 tended to increase in the early stage of heating then decrease toward the end of the heating period. The increases in the areas of peak 4 over heating time were highly correlated with the total polar compounds in the heated oils; a 27% level of total polar compounds, the recommended level for discarding a frying fat, corresponded to a 5 $cm^2$ area of peak 4 when a 10 $\mu$g sample was injected. The authors also provided the following experiment to demonstrate the relationship between the HPSEC method and the total polar compounds in the heated oils. The non-polar fraction ("F-1") and polar fraction ("F-2") of a heated oil sample eluted by the column chromatographic method were run by HPSEC; the F-1 of a heated oil contained only peak 1, while all four peaks occurred in the F-2. The peak 1 area of F-1 of the heated oil decreased gradually through the entire heating time, but peak 1 area of F-2 increased in the early stage of the heating period then leveled off toward the end of heating period. The authors reported also that most conjugated TG in the fresh oils were weakly oxidized and were thus non-polar. Decrease of unoxidized TG (peak 1) from F-1 was accompanied by an increase of oxidized TG that appeared as peak 1 in the F-2. areas of all peaks in F-2 increased then leveled off during heating; this was caused by incomplete recovery of polar compounds after 42 hr of heating. The magnitude of increase in peak 4 area in F-2 of a heated oil was much greater than that of other peaks; this corresponds to the increase in the total polar compounds in the heated oil. One of the advantages of this method is its speed; it requires 2 min of sample preparation and 20 min of HPSEC run time.

Petroleum Ether-Insoluble Oxidized Fatty Acids Method

It is recommended that a frying fat be discarded if the concentration of petroleum ether-insoluble oxidized fatty acids ("PEIOFA") is 1.0% higher. The PEIOFA is determined by the following steps. A frying fat sample is saponified with potassium hydroxide in ethanol, and the soap solution is acidified and thoroughly extracted with ether. After evaporation of solvent, the mixture of fatty acids is reextracted with boiling petroleum ether. The ratio of weight of remaining petroleum ether insoluble material to the sample weight is determined as PEIOFA. Billek et al., "Quality Assessment of Used Frying Fats: A Comparison of Four Methods," J. Am. Oil Chem. Soc., 55:728–733 (1978), which is hereby incorporated by reference, compared the results of frying fat quality measured by the PEIOFA method with those measured by gel permeation chromatography ("GPC"), liquid chromatography ("LC"), and column chromatography ("CC") methods. They concluded that 1% of PEIOFA in frying fat corresponded to 15% of polymeric triglycerides measured by the GPC method, 28% of total polar artifacts measured by LC method, and 27% of total polar components measured by CC methods, respectively.

Gray reviewed measurements of lipid oxidation. He noted that no single chemical method correlated with changes in organoleptic properties of oxidized lipids throughout the entire course of autoxidation. As mentioned earlier, Smith surveyed the qualities of used frying fat from fast food restaurants by evaluating the dielectric constant, TPC, FFA, and fatty acid profiles. In general, they found close correlations between frying times and increases in dielectric constant (r=0.84), percentage of TPC (r=0.80), and percentage of FFA (r=0.88). The correlation coefficients between increase in dielectric constant and TPC, and between increase in dielectric constant and FFA were 0.93 and 0.92, respectively, and showed that the dielectric constant method was an easy and convenient alternative method of quality control of frying fats for a fast food restaurant. The greatest changes in fatty acid profiles occurred with trans-C18 monoenes (elaidic acid), which decreased with hours of use (r=−0.69). Palmitic acid increased (r=0.69), but stearic acid decreased (r=−0.66) over the use periods of the frying fats (Gray; Smith).

In spite of the many methods for measuring oil stability to oxidation and of many measurements of oil degradation products formed during frying, there is still a need for a rapid method for measuring stability of an oil to frying. The current methods of Oil Stability Instrument or Rancimat for measuring resistance of fats/oils to thermal oxidation still require rather long periods of time (hr) and fail to take into consideration the effect of hydrolysis on frying oil stability. These tests also do not measure the stabilizing effect of surface active agents such as siloxanes on the frying oils (Melton). therefore, a need still exists for a more rapid and reliable method for measurements of the stability of frying fats/oils and the effects of the different additives, such as antioxidants and surface active agents, on that stability.

SUMMARY OF THE INVENTION

The present invention relates to a novel instrumental method for rapid and accurate measurement of the oxidative stability of fats/oils was developed. An instrument made in accordance with the present invention utilizing this method has also been developed. The instrument permitted oxidation of fats at frying temperatures while moisturized air was bubbled through the hot oil. Measurements were based on increase in conductivity of water-trapped decomposition products from the oil.

The instrument comprises four major parts: a moisturized air source, a sample reaction vessel, a volatile compound trap, and an automatic data acquisition and control system. Two hundred grams of oil were placed in a glass flask and heated at a controlled temperature. A steady stream of air (200 mL/min) was moisturized by passing it through the headspace of a closed water canister at a controlled temperature. The moisturized air bubbled into the oil sample, and then through the head space, which was transferred by the positive flow of the air stream into receiving water consisting of 200 mL of HPLC-grade deionized water ("DW") at 18° C. for a volatile trap. Conductivity in the volatile trap was monitored and recorded by a personal computer. All temperature controls and data acquisition were automated and computerized using a computer interface with a personal computer. The volatile decomposition compounds ("VDP") of the oxidized oil increased conductivity of the volatile trap.

The instrument provided two measurements of the oil oxidative stability based on the conductivity increase in the volatile trap with respect to time of analysis; this curve was termed the instrument curve. The instrument curve was a third degree polynomial curve. The linear slope was defined as the linear slope of the instrument curve between the conductivity of 4.0 and 11.0 $\mu$S/cm, which was within the induction period of the oil oxidation. The linear slope indicated the formation rate of the VDP produced by the oil during the initiation stage of lipid oxidation. The linear slope is directly proportional to the oxidative stability of an oil. The induction time was defined as the time at which the oxidation of an oil turned from the initiation stage into the propagation stage. The induction time was determined as the time for an oil sample to exceed 0.2 mM of the acid concentration (acetic acid equivalents) during the instrument test. The acid concentration in the volatile trap was calculated from the conductivity by an exponential relationship between the conductivity and a series of acetic acid solutions of known concentrations. The induction time measured the duration of the initiation stage of lipid oxidation and was inversely proportional to the oxidative stability of an oil.

The oil temperature and water temperature settings of the instrument were optimized to obtain maximum precision. Regular sunflower oils were analyzed for linear slope and induction time by the instrument at different combinations of oil temperature and water temperature settings. Optimum operating parameters of the instrument were determined by selecting the combination of oil temperature and water temperature settings that exhibited minimum coefficients of variation ("CV") for the linear slope and induction time during testing of sunflower oil. By setting the oil temperature setting at 160° C. and the water temperature setting at 50° C., the minimum CV of linear slope and induction time, which were 2.72% and 2.37%, respectively, were obtained. Since both CV of the linear slope and induction time of the sunflower oil at the optimum temperature settings were less than 5%, the maximum tolerance for a precise instrument, the results of the instrument method were found to be precise and reproducible.

Four soybean oils with a series of iodine values (70, 94, 110, and 132) were tested for oxidative stability by the instrument. The oxidative stabilities of these oils were differentiated ($P<0.05$) by the linear slope and induction time. The linear slope increased with increasing iodine values, while the induction time decreased. The linear slopes for the oil with iodine values of 70, 94, 110, and 132 were 0.12, 0.24, 0.31, 0.46 $\mu$S/cm.min, respectively. The linear slope of each oil was different ($P<0.05$) from the others. The linear slopes of the oils suggest that the higher the unsaturation level, the larger the formation rate of VDP during the induction period. The induction time ranged from 95.5 min for the most saturated oil to 32.4 min for the most unsaturated oil. The longer the induction time of an oil, the greater its resistance to oxidation.

The soybean oil with an iodine value of 94, indicating a medium oxidative stability, was treated with 5 ppm dimethyl siloxane ("DMS"), 100 ppm tertiary-butylatedhydroquinone ("TBHQ"), or both DMS and TBHQ, and was tested for oxidative stability by the instrument. The linear slope of the soybean oil tested by the instrument was greatly reduced by the addition of DMS, TBHQ, or a combination of both; this indicated that addition of DMA, TBHQ, or both DMS and TBHQ to the frying oil increased its oxidative stability. The linear slope of oil treated with TBHQ or with both DMS and TBHQ was lower ($P<0.1$) than that of the oil treated with DMS. In addition, the induction time of the oil containing DMS was lower ($P<0.1$) than in that treated with TBHQ or both DMS and TBHQ. These results suggested that the oil treated with TBHQ was more resistant to oxidation under frying conditions. The linear slope and induction time of the oil containing both DMS and TBHQ were not different from those of the oil treated with TBHQ alone; this indicated that the addition of DMS to the oil already containing TBHQ did not increase its oxidative stability. The oil stability index of the oil treated with 5 ppm DMS measured by the Oil Stability Instrument was not different from that of the control oil. The instrument is more sensitive than the Oil Stability Instrument in detecting the difference in oxidative stability between the oils with and without treatment of DMS.

The volatile fatty acid ("VFA") level in the DW trapped from the oils during the instrument test followed a trend similar to that of linear slopes among the soybean oils with different unsaturation levels or with different additive treatments. This indicated that the VFA accounted mainly for the conductivity increase in the volatile trap. Formic and acetic acids were the most abundant acids of all volatile fatty acids produced by both sunflower and soybean oils during the instrument test.

Total polar components ("TPC") of soybean oils increased after the oils were tested for 200 min by the instrument. The more saturated oil had a smaller increase ($P<0.05$) in TPC in the oil after the instrument test than the more unsaturated ones. The increase in the TPC in the oil treated with DMS, TBHQ, or a combination of both was less ($P<0.05$) than that in the control oil. The dielectric constant of the oils followed the same distribution pattern as TPC. Increase in the free fatty acids in the instrument-tested oils suggested that the moisture brought into the oil sample during the instrument sample increased the hydrolytic reactions in the oil. Dienoic acid levels in the instrument-tested oils were higher ($P<0.05$) than those in the untested oils. Levels of fatty acid C18:2 in the oil decreased after the instrument test but the concentrations of C16:0, C18:0, and C18:1 increased. After the instrument test, the ratio of C18:2 to C16:0 ("RATIO") of the fresh oil with an iodine value of 94 decreased from 3.06 to 2.77. The RATIOs of the instrument-tested oils containing TBHQ (including the oil treated with both DMS and TBHQ) were slightly smaller that of the control oil; this was not expected. The oils that were more resistant to oxidation during the instrument test had lower levels of degradation products in the oils.

The tocopherols in the oils before and after the instrument test were monitored in order to understand the effect of tocopherols on the oxidative stability of the oils. The antioxidative efficiency of tocopherols was in the order of γ->α->Δ-tocopherol. The hydrogenated soybean oils suffered from more destruction (P<0.05) of total tocopherols (91.3% and 97.8% for the oils with IVs of 70 and 94, respectively) during the instrument test than the unhydrogenated one (57.6%). The oils treated with additives had less total tocopherol destruction than the control oil. Both DMS and TBHQ contributed antioxidative activities to the oil and thus reduced the oxidative destruction of tocopherols in the oils.

The ability of the instrument to measure oil stability to oxidation was represented by the high correlation relationships between the linear slope or induction time and the oil stability index of the soybean oils as measured by the Oxidative Stability Instrument. The oil stability index of soybean oils with different unsaturation levels or different additive treatments (except for the oil containing DMS) can be estimated with either the induction time or the linear slope of the instrument measurement using regression equations (oil stability index with respect to induction time or linear slope) of which the regression coefficients ("R-square") were 96% and 90%, respectively. The high regression coefficients indicate that the instrument is accurate in measurement of oil stability to thermal oxidation. The instrument provides a fast, reproducible, accurate, simple, and potentially economical analytical method to analyze the oxidative stability of fats/oils.

BRIEF DESCRIPTION OF THE DRAWINGS

FIGS. 6A–B are a least-squares mean total polar component levels and dielectric constants (Food Oil Sensor reading), respectively, of soybean oils with different iodine values (IVs) or degrees of unsaturation (Tested=instrument-tested oil and Fresh=before instrument test); bars with unlike letters are different (P<0.05).

DETAILED DESCRIPTION OF THE INVENTION

Materials and Methods

Figure 1:
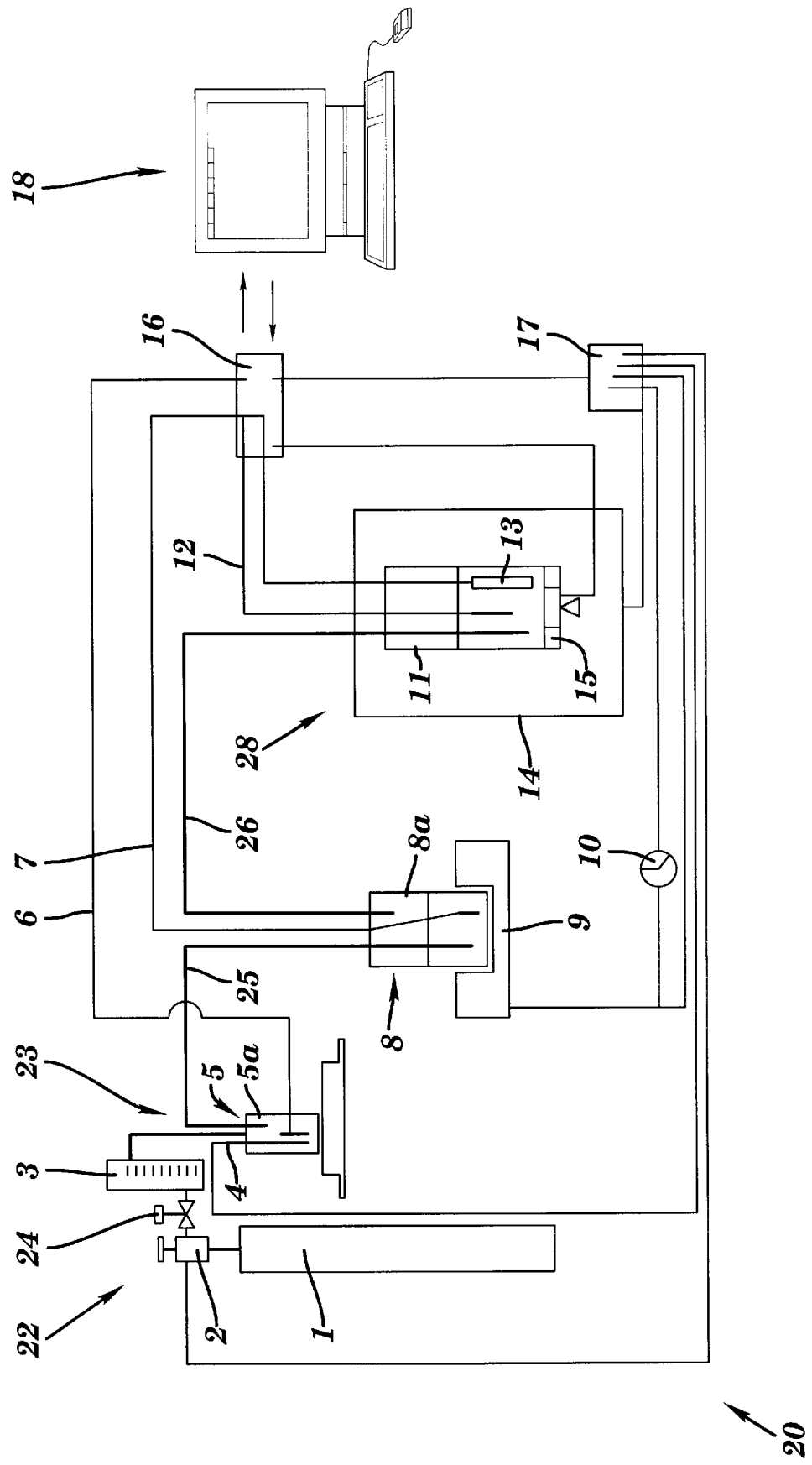
FIG. 1 is a flow diagram of an instrument made in accordance with the present invention.

The experimental procedures were divided into four sections: (1) the design and performance assessment of an instrument 20 for measurement of stability of fats and oils, (2) optimization of the conditions for a method for measurement of stability of fats and oils, (3) evaluation of effects of different unsaturation levels in an oil on the instrument 20 measurements, and (4) determination of the effects of different additives (silicones and antioxidants) in a single oil on the instrument 20 measurements. The chemical changes in the oils occurring during the instrument tested oils in objectives 3 and 4 were determined. The total level and concentration of volatile fatty acids collected in the HPLC-grade deionized water during the instrument tests of the oils in objectives 2, 3, and 4 were analyzed also. The experimental design of this study was a completely randomized block design. For a fuller understanding of the nature and desired objects of this invention, reference should be made to the following detailed description taken in connection with the accompanying drawings, wherein like reference numerals designate corresponding parts throughout the several figures.

1. Design of the Instrument

In accordance with the present invention, an instrument 20 for oil oxidative stability measurement automatically measures the conductivity of deionized water that traps oil volatile decomposition compounds ("VDP") formed in a heated oil sample. A purpose of the instrument 20 for oil stability measurement is to achieve overall automation of the measuring process by using both an automatic data acquisition system and automatic device controls. An embodiment of the instrument 20 made in accordance with the present invention is shown in FIG. 1. Four major components comprise the instrument 20: moisturized air source 22, sample reaction vessel 8, volatile compound trap 28, and automatic data acquisition and control system 16 and 18.

Moisturized Air Source

The moisturized air source 22 provides constant air flow and moisture to the heated oil sample in order to accelerate hydrolysis and oxidation reactions. This part of the instrument comprises a compressed air tank 1, air regulating devices 2, a solenoid valve 24, a flow meter 3, and a moisture supplier 23. The air regulating devices 2 are adjusted to provide a constant air flow (200 mL/min) to the instrument. An air regulator, Fisher® Brand multistage cylinder regulator for air (Fisher Scientific Co., Pittsburgh, Pa.), reduces the high pressure of the compressed air tank to 1 psi. The flowmeter 3, Gilmont flowmeter model GF-4340

(Gilmont Instrument In., Barrington, Ill.) is calibrated with air and used to measure the flow rate of the air stream. A valve placed in line with the air regulator is adjusted to deliver 200 mL/min of air flow. A solenoid valve 24, placed between the air regulating devices 2 and the flow meter 3, opens when the oil temperature in the reaction vessel 8 reaches 15° C. below the set point of oil temperature at which the instrument test is conducted. The moisture supplier 23 comprises of a 600-mL flask 5, a thermal sensor 6, a magnetic mixer (not shown), and an immersion heater 4. Three hundred milliliters of distilled water is placed in the flask 5, which is sealed with a rubber stopper (not shown) and controlled at 50° C. by a system comprising a temperature sensor 6, a sheath immersion heater 4, model VPT-107 (Omega Engineering, Inc., Stanford, Conn.), and an analog interface 16, Model CIO-DAS08AOH (Computer Board Nc., Mansfield, Mass.). the temperature sensor 6 comprises Type-T thermocouple wires (Omega Engineering, Inc., Stanford, Conn.) inserted into a 1.59 mm inside diameter (i.d.) stainless steel tube of which the probe end is sealed by compression. Water in the flask 5 is stirred by a magnetic stirrer driven by a Fisher Magnetic Automixer (Fisher Scientific, Pittsburgh, Pa.). Water temperature can be controlled in the range of 30–100° C. At a constant temperature, this device provides that a constant water vapor pressure is maintained in the headspace 5a of the flask, or reservoir 5. The temperature sensor 6 transmits an electric voltage to the computer interface 16, which produces feedback to control the immersion heater 4, thus controlling the water temperature. When the air flow rate and water vapor pressure in the headspace 5a of the water reservoir 5 are constant, the moisture level brought into the oil sample is also assumed to be constant. The air blows into the water reservoir, picks up a constant amount of moisture, and bubbles into the oil sample through a stainless steel tube (i.d. 1.59 mm) 25. This part of the instrument automatically provided air with a constant moisture level to the oil sample.

Sample Reaction Vessel

The sample reaction vessel 8 holds a 200 g oil sample at a controlled temperature, ranging from ambient temperature to 220° C. This part of the instrument 20 comprises a 600-mL flask with a rubber stopper (not shown), a stainless steel temperature sensor 7, a heat source 9, such as, a Corning PC-35 hotplate (Corning Glass Works, Inc., Corning, N.Y.), and a timer relay 10, Model GT3W-A66AF20 (Idec Inc., Tokyo, Japan).

The temperature of the oil sample is controlled semi-automatically by two stages of heating. The first stage brings the temperature of the oil sample from the ambient temperature up to 20° C. below the set point. The second stage of heating maintains the oil at the set point temperature. During the first stage of heating, the hotplate 9 is heated continuously. The second stage of heating does not take place until the oil temperature reaches 20° C. below the set point temperature. The timer relay 10 periodically interrupts the electric current to the hot plate 9 in order to reduce its energy output and smooth the temperature curve over time.

The next step is to transfer the VDP from the oil to HPLC grade deionized water ("DW"). This is accomplished when the headspace 8a above the sample reaction vessel 8 is transferred into DW. After the moisturized air is introduced into the heated oil, the steam and the fumes produced by the heated oil are transferred with the positive air flow to the DW through a stainless steel tube (i.d. 4.0 mm) 26.

The stainless steel tube 26 is then recycled through a thorough washing procedure. The tube is first sprayed with pressurized petroleum ether ("PE") (aerosol PE canister), then rinsed with hot water. The tube 26 is washed again with 400 mL of hot detergent, Dawn® concentrated dish washing detergent (Procter & Gamble Co., Cincinnati, Ohio), and rinsed with hot water and distilled water. The interior of the washed tube 26 is dried with a stream of hot air, generated by a heat gun (not shown) at one end and pulled by a vacuum pump (not shown) at the other end.

Volatile Compound Trap

Figure 2:
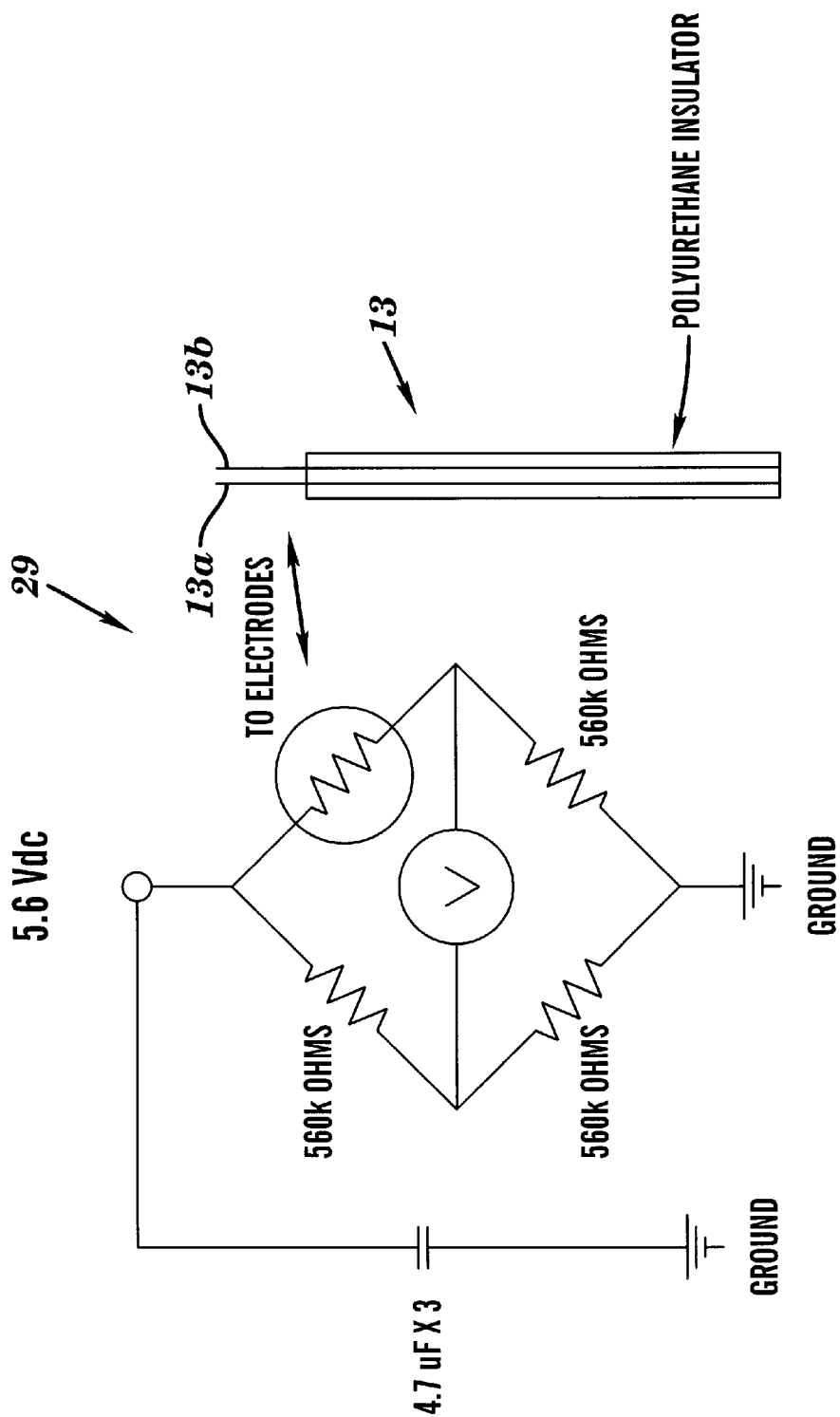
FIG. 2 is an electrical schematic of a conductivity probe of the instrument.

The volatile compound trap 28 provides for substantially the total collection of the VDP in the headspace 8a above the oil sample reaction vessel 8. The volatile compound trap comprises a 600-mL glass beaker 11, a type-T thermocouple 12, a conductivity probe 13, a thermal electric cooling box 14, and a 0–500 g electronic scale (Sartorius Type 1002 MP9, Sartorius Corp., Bohemia, N.Y.). The beaker 11 is filled with 200 mL of DW, which is used to trap oil volatiles and of which the conductivity is measured by the conductivity probe 13 and the computer interface 16. The design of the conductivity probe 13 is shown in FIG. 2. The voltage drop across the water/solution between two stainless steel rods 13a and 13b (diameter 2.24 mm), set 9.5 mm apart, is measured by a bridge circuit 29 and the computer interface 16, which is used to calculate the conductivity. The bridge circuit 29 utilizes a 5.6 Vdc voltage supply. Each resistor used by the bridge has 560 KΩ resistance with 2% tolerance. The conductance and the conductivity of the trap solution are calculated by Equations 1 and 2, respectively.

Equation 1: $$G = \frac{1}{R} = \frac{(2.8-V)}{(2.8+V)560000}$$

where R=resistance of deionized water, G=conductance in siemens, and V=volts.

Equation 2: $$L = \frac{G \cdot d}{A} \times \frac{(200\,g = \text{Weight Change})}{200\,g}$$

where L=conductivity in siemens/cm, G=conductance in siemens, d=0.95 cm (distance between two electrodes), A=0.079137 cm$^2$ (the area of the electrodes exposed to current flow).

The conductivity in the trap solution is adjusted by the weight change detected by the electronic scale 15 connected to the PC 18. The weight change is the difference in total weight of the beaker containing the trap solution between the initial stage and any conductivity measurement time. The weight change is mainly due to the moisture condensation from the air bubbling through water and hot oil before entering the volatile compound trap 28; the weight change is used to compensate for the dilution in the trap solution.

The temperature of the trap solution is controlled at 18° C. by the thermocouple 12, computer interface 16, and an electric cooler 14. The trap solution is placed inside the electric cooler 14, of which the temperature is monitored and controlled by the computer 18. The loss of volatiles such as volatile acids to the surroundings is minimized by maintaining the temperature of the trap below 20° C. (deMan).

Data Acquisition and Automatic Control System

The data acquisition system 16 reads data from sensors, including temperature (6, 7, and 12) and conductivity (13) sensors, and stores it into a personal computer ("PC") 18, IBM model 350-100DX4 (International Business Machine Inc., New York). The PC 18 reads and processes the data and then produces digital output to control the peripheral devices. The computer interface 16, CIO-DAS08AOH, which has 8 channels of analogue signal inputs and 8 channels of digital output, is installed in the PC 18. The signals, transmitted from the sensors 6, 7, 12, and 13, are logged into the PC 18 automatically through the differential input channels on the computer interface 16.

Figure 12:
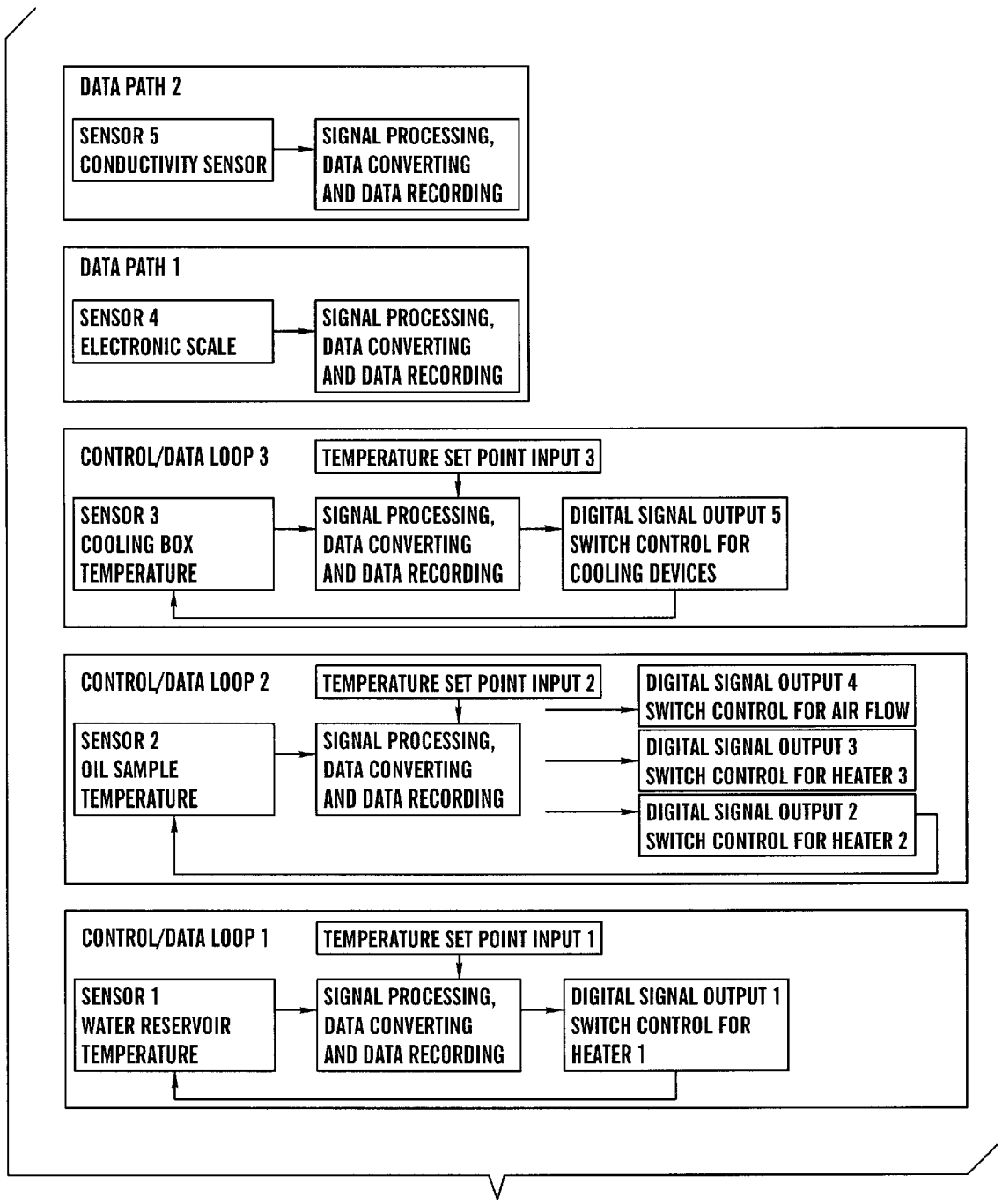
FIG. 12 is a logic flow diagram of the instrument operation system.

The computer system 18 controls the peripheral devices using a software program and the digital output on the computer interface 16. The peripheral devices are operated by relay switches controlled by the digital output on the computer interface. The computer program, written in Visual Basic® (Microsoft Corp., Beaverton, Oreg.) as shown in Appendix A, converts, analyzes, and compares the analogical input, controls the digital output for relay switching and stores the data in the PC 18. The control logic of the software program is shown in FIG. 12. All data are compiled by the computer 18 at 8-sec intervals. Data, including conductivity, time, oil setting temperature, water setting temperature, and weight change, are recorded by the computer at 30-sec intervals. The computer 18 starts timing and collecting data when the oil temperature reaches 10° C. below the set point temperature.

Determination of Oil Oxidative Stability

The oxidative stability of oils is determined by the conductivity of the DW with respect to time (instrument curve). A typical instrument curve is a third order polynomial curve, of which only the linear portion of the curve ranging between 4 $\mu$S/cm and 10 $\mu$S/cm is used. The slope of the linear regression lien of conductivity with respect to time within this range is determined as the linear slope. Time is zeroed at 4 $\mu$S/cm conductivity on the instrument curve to assess the linear slope.

Conversion of conductivity in the solution of the volatile trap into acid concentration forms another measuring parameter. The conductivity probe is calibrated with a series of acetic acid solutions ranging between 0.01 mM and 20 mM concentrations. The conductivity in the trap solution is converted to the concentration of acetic acid according to Equation 3 based on the logarithmic regression between the conductivity and acid concentrations.

Equation 3: $\quad$ Acid concentration $= e^{\frac{(conductivity - 15.56)}{2.442}}$ The acid concentration is plotted with respect to time again and forms another curve referred to as the acid curve. The acid curve comprises of a log phase and a log phase, which starts leveling off after passing 0.2 mM acid concentration. Therefore, the time required to reach 0.2 mM acid concentration on the acid curve is determined as the induction time.

2. Experimental Plan

The experimental design objective 2 was a randomized complete block using a single oil (regular sunflower oil). Refined, bleached and deodorized ("RBD") sunflower oil (1.0 L) was obtained from an oil processor in the United States and was used to complete all planned research for this objective. The instrument curves were obtained at three different oil temperatures (160, 175 and 190° C.) with 200 mL/min of air bubbling through the oil. Different levels of moisture were achieved by controlling the water reservoir temperature at one of three different temperatures (40, 50 and 60° C.). A single replication, as shown in Table 1, comprising all combinations of oil temperature (160, 175 and 190° C.) with water temperature (40, 50 and 60° C.). Three replications of these nine different combinations were completed. The order in which each replication-combination was run was randomized across replication and combination of oil and water temperatures. Water-soluble fatty acids (C1–C7) collected during one replication at the different oil and water temperatures were analyzed by gas chromatography ("GC") using a modified method of deMan, as described later.

TABLE 1

A single replication showing the combinations of the different oil temperature settings (OTSs) and water temperature settings (WTSs) used for objective 2

| WTS (° C.) | 160 (a) | 175 (b) | 190 (c) |
|---|---|---|---|
| 40 (1) | a1 | b1 | c1 |
| 50 (2) | a2 | b2 | c2 |
| 60 (3) | a3 | b3 | c3 |

The experimental design for objective 3 was also a randomized compete block model for determination of instrument 20 parameters, levels of volatile fatty acids in trap solution, and measurements of instrument 20 tested oils. Four soybean oils, each representing a different level of saturation, were tested. Unhydrogenated soybean oil with an iodine value ("IV") of 132 and soybean oils that had been hydrogenated to three other levels of saturation (IVs=70, 94, and 110) were obtained from an U.S. oil processor. Enough (3.8 L) of each oil was obtained at one time to complete all research planned for this objective. A replication consisted of testing each of the four oils, and three replications were completed. The order in which each oil-replication combination was run was randomized across oil and replication. The instrument curves were determined at 160° C. oil temperature and 50° C. water temperature for 200 min.

In addition, the water-soluble volatile fatty acids were collected for each oil-replication combination and were analyzed as described later. A sample of each type of fresh oil and each oil sample analyzed by the instrument 20 were analyzed for total free fatty acids ("FFA") content, fatty acid composition, total polar components, conjugated dienes level, dielectric constant, and concentrations of tocopherols (AOCS, *Official and Tentative Methods of Analysis of the American Oil Chemists Society*, American Oil Chemists Society, Champaign, Ill. (1993), which is hereby incorporated by reference).

The experimental design for objective 4 was a randomized complete block design. An RDB soybean oil with 94 IV was selected to this experiment. In order to complete this research, 15.2 L of this oil were obtained at one time from the oil processor mentioned earlier. The RDB soybean oil served as the control treatment. To one 3.8-L portion of this oil, 5 ppm of dimethyl siloxanes ("DMS") were added; to a second 3.8-L portion, 100 ppm of TBHQ were added; to a third 3.8-L portion, 5 ppm DMS and 100 ppm TBHQ were added. Each oil portion with its additive was considered a treatment. The levels of DMS and TBHQ added were the same as those levels normally added to frying oils/fats in the U.S. A replication consisted of the four treatments of the oil including the untested control oil for the baseline comparison, and three replications were completed. The order in which replication-treatment combinations were run was randomized across replication and treatment. The linear slope and induction time for each replication-oil sample combination were obtained, as described later. The water-soluble volatile fatty acids in the DW solution from each replication-treatment combination were analyzed as described previously. Samples of each fresh oil and each instrument-tested oil were analyzed for total FFA content, fatty acid profile, total polar components ("TPC"), conjugated dienes level, dielectric constant, and concentrations of tocopherols (AOCs, *Official and Tentative Methods of Analysis of the American Oil Chemists Society*, American Oil Chemists Society, Champaign, Ill. (1993)).

3. Chemical Changes Occurring in the Volatile Trap Solution

Volatile Fatty Acids in the Volatile Trap Solution

The trap solution samples were analyzed for total acid content and volatile fatty acids ("VFA") by a method modified by deMan. Twenty milliliters of solution, with 1 mg of isovaleric acid added as an internal standard, were neutralized with 1 mL of 0.1 N sodium hydroxide. The neutralized solution was dried on a rotary evaporator at 55° C. to near dryness. The dried sample was acidified with 1 ml of 0.2 N hydrochloric acid and analyzed by gas liquid chromatography ("GLC"). The acidified sample (1.5 µL) was injected into and analyzed on a 0.25 mm i.d.×25 m long HP-FFAP capillary column (Supelco, Inc., Bellefonte, Pa.), in a Shimadzu Model 9-AM GC (Shimadzu, Columbia, Md.) using an injection splitter with a split ratio of 8 to 1. Temperature program of the column oven increased from 70° C. to 200° C. at a rate of 6° C./min. The flow rate of carrier gas (helium) was controlled at 2 mL/min.

An internal standard method was used to calculate the concentrations of VFA in the trap solution. A standard solution containing known levels of VFA (Sulpelco Inc., Bellefonte, Pa.) and isovaleric acid as the internal standard (Table 2) was prepared, analyzed by GLC, and used to determine the relative response factors ("RRx") of different VFA versus isovaleric acid as shown by Equation 4.

Equation 4: $$RRx_{Std} = \frac{Area_{Std} \times Conc._{Isovaleric\ Acid}}{Area_{Isovaleric\ Acid} \times Conc._{Std}}$$

where area=GC peak area, conc.=concentration, and std=standard compound. Positive identification of each component peak was made by matching the retention time ("RT") of the component peak with that of the standard peak (Table 2) with a 2% tolerance level. The concentration of the identified component was calculated according to Equation 5.

Equation 5:
$$Conc._{Component\ Peak} = \frac{Area_{Component\ Peak}}{Area_{Isovaleric\ Acid} \times RRx} \times Conc._{Isovaleric\ Acid}$$

The recovery rates of different VFA analyzed by this method also were determined. Twenty milliliters of one of the trap solutions collected during the experiment for objective 2 were spiked with known concentrations of standard VFA as shown in Table 2, and four repetitions were completed. The spiked samples and unspiked sample were analyzed for VFA. The recovery rate (%) of each VFA was determined by Equation 6.

TABLE 2

Retention time, concentration, and amounts of spike for different volatile fatty acids

| Retention time (min) | Volatile fatty acid | Concentration of standard mix | Amounts of spike (mg)[a] |
|---|---|---|---|
| 3.59 | Acetic | 10 mM | 0.600 |
| 4.58 | Propionic | 10 mM | 0.741 |
| 4.92 | Isobutyric | 10 mM | 0.881 |

TABLE 2-continued

Retention time, concentration, and amounts of spike for different volatile fatty acids

| Retention time (min) | Volatile fatty acid | Concentration of standard mix | Amounts of spike (mg)[a] |
|---|---|---|---|
| 5.80 | Butyric | 10 mM | 0.881 |
| 6.40 | Isovaleric | 10 mM | 1.121 |
| 7.50 | n-Valeric | 10 mM | 1.121 |
| 8.57 | Isocaproic | 10 mM | 1.162 |
| 9.27 | n-Caproic | 10 mM | 1.162 |
| 11.07 | Heptanoic | 10 mM | 1.302 |

[a]Added to 20 mL of the solution sample from the volatile trap.

Equation 6: $$Recovery\ \% = \frac{Conc._{Spiked\ Sample} - Conc._{Control}}{Amounts\ of\ spiked\ concentration} \times 100\%$$

Finally, the concentration for each identified volatile fatty acid in the deionized water was compensated for by the recovery rate of the fatty acid according to Equation 7.

Equation 7:
$$Conc._{Component\ Peak} = \frac{Area_{Component\ Peak}}{Area_{Isovaleric\ Acid} \times RRx} \times \frac{Conc._{Isovaleric\ acid}}{Recovery\ \%}$$

Free Fatty Acids in the Trap Solution

Free fatty acids (FFA) in the trap solution sample were measured by the titration method. Twenty milliliters of the trap solution containing several drops of 1% phenolphthalein indicator solution (W/V in 95% alcohol) were titrated with 0.01 N sodium hydroxide until the color of the mixture turned from colorless to light pink. The actual concentration of sodium hydroxide was determined according to AOAC, *Official and Tentative Methods of Analysis of the Association of Official Analytical Chemists*, 12th ed., Association of Official Analytical Chemists, Washington, D.C. (1975), which is hereby incorporated by reference, Official Method 50.003 and expressed as millimolarity of acid concentration. The concentration of total FFA in the sample was expressed in mM acid concentration and calculated by Equation 8.

Equation 8: $$FFA(mM) = \frac{mL\ of\ alkali \times N}{20\ mL} \times 1000$$

were N=normality of sodium hydroxide solution.

4. Chemical Changes Occurring in the Oils Tested by the Instrument

Free Fatty Acids in Oil

Free fatty acids levels in the oils tested by the instrument 20 were determined according to AOCS Official Method Ca 5a-40 (AOCS, *Official and Tentative Methods of Analysis of the American Oil Chemists Society*, American Oil Chemists Society, Champaign, Ill. (1993)). Thirty grams of oil were weighed into a 200-mL flask. Fifty milliliters of hot (80° C.) neutralized alcohol and 2 mL of 1% phenolphthalein solution were added. The mixture was titrated immediately with sodium hydroxide solution as described previously until the color of the mixture turned from a cloudy white to a pale pink color for approximately 30 sec. The percentage of free fatty acids in each oil tested by the instrument 20 for objectives 3 and 4 was expressed as percentage of oleic acid and was calculated by Equation 9.

Equation 9: $$FFA(\% \text{ oleic acid}) = \frac{\text{mL of alkali} \times N \times 28.2}{\text{Wt. of Sample (g)}}$$

where N=normality of sodium hydroxide solution.

Fatty Acid Profile

The fatty acid compositions of oils tested by the instrument 20 for objectives 3 and 4 were determined according to AOCS Official Method Ce 2-66 (AOCS, Official and Tentative Methods of Analysis of the American Oil Chemists Society, American Oil Chemists Society, Champaign, Ill. (1993)). Triglycerides were converted to methyl esters of their fatty acids before they were analyzed by GC. The fatty acids were esterified according to the following steps. An oil sample (approximately 100 mg) was weighed into a 125-mL Erlenmeyer flask and 4 mL of 0.5 N methanolic sodium hydroxide solution were added. The mixture was boiled under reflux for 10 min, then 5 mL of 14% boron trifluoride-methanol reagent (Supelco Inc., Bellafonte, Pa.) were added. After another 2 min of refluxing, the mixture was cooled to ambient temperature. Eight milliliters of hexane were added to the mixture to extract the fatty acid methyl esters ("FAME"). The hexane layer was separated by adding saturated sodium chloride to the mixture. The hexane was transferred to a test tube and dried with a small amount of anhydrous sodium sulfate. The FAME were analyzed within 24 hr of their preparation.

FAME were analyzed by GC according to AOCS Official Method Ce 2-66 (AOCS, Official and Tentative Methods of Analysis of the American Oil Chemists Society, American Oil Chemists Society, Champaign, Ill. (1993)). FAME were analyzed on a 0.25 mm i.d.×25 m long fused silica SP2330 column (Supelco, Inc., Bellefonte, Pa.), in a Shimadzu Model 9-AM GC (Shimadzu, Columbia, Md.). For each sample, a FAME solution (1.5 $\mu$L) was injected into and analyzed by the GC using an injection splitter with a split ratio of 10 to 1. The injector and detector temperatures were set at 250 and 280° C., respectively. The signal of the GC was processed by a Shimadzu CR-5-A integrator (Shimadzu, Columbia, Md.). The column temperature started at 150° C. and increased to 200° C. at a rate of 2° C./min. The flow rate of carrier gas, helium, was set at 2 mL/min. AOCS Oil Reference Mixture RM-1 (Matreya, Inc., Pleasant Gap, Pa.) was analyzed by the same GC method and was used as the reference for retention times and calibration factors of the standard fatty acids. The calibration factor was calculated by comparison of relative GC response for each fatty acid component to that of methyl palmitate, according to (AOCS, Official and Tentative Methods of Analysis of the American Oil Chemists Society, American Oil Chemists Society, Champaign, Ill. (1993)). Positive identification was made by matching the retention time of the component fatty acid in the oil sample with that of standard compound with a 2% tolerance range. The percentages of the following fatty acids in each oil were determined: palmitic (C16:0), stearic (C18:0), oleic (C18:1), linoleic (C18:2), and linolenic (C18:3).

Total Polar Components

A rapid method was used to determine the total polar components ("TPC") in the oils tested by the instrument 20 (Melton et al., "A Rapid Method for Determination of Total Polar Component in Frying Oils," J. Am. Oil Chem. Soc., 64:664—665 (1987), which is hereby incorporated by reference). Approximately 0.2 g of oil sample was dissolved in 4 mL of petroleum ether:diethyl ether ("PE:EE") (92:8 v/v) and delivered onto a Bond-Elut column (Analytichem, Harbor City, Calif.) containing 2 g of silica. The loaded Bond-Elut column was eluted with 30 mL of the PE:EE solvent under 5 mm-Hg vacuum to separate the non-polar components ("NPC") from the polar components. The separation of TPC from HPC was confirmed by thin layer chromatography (TLC) using AOCS Official Method Cd 20-9 (AOCS, Official and Tentative Methods of Analysis of the American Oil Chemists Society, American Oil Chemists Society, Champaign, Ill. (1993)). The TLC developing solvent was a mixture containing PE, EE, and acetic acid with a ratio of 70:30:2, respectively. The solvent in the eluted solution containing NPC was removed by heating on a stem bath under a gentle stream of nitrogen; the container was then dried in a 105° C. hot air oven. The TPC in oil was determined by Equation 10.

Equation 10:
$$TPC\% = \frac{(\text{Oil Wt.} - \text{Dried } NPC \text{ Wt.})}{\text{Oil Wt.}} \times 100\%$$

Dienoic Acid

Conjugated dienoic acids in the oils tested by the instrument 20 were determined according to AOCS Official Method Ti 1a-64 using spectrophotometry (AOCS, *Official and Tentative Methods of Analysis of the American Oil Chemists Society*, American Oil Chemists Society, Champaign, Ill. 1993)). Three grams of the oil sample were diluted to a final volume of 10 mL with 2,2,4-trimethylpentane (isooctane). Each diluted oil sample was loaded into a quartz cuvette, with alight path of 1 cm. The absorbance of the diluted oil sample at a wavelength of 233 m was measured by a Shimadzu Spectrophotometer Model UV-2101 (Shimadzu Scientific Instruments, Columbia, Md.), which was calibrated with deionized water prior to the measurement. The concentration of conjugated dienoic acid in the oil was calculated by Equation 11.

Equation 11:
$$\text{Dienoic acid}\left(\frac{mg}{100 \text{ g oil}}\right) = \left(0.84 \times \left(\frac{A_s}{bc}\right) - K_0\right) \times 1000$$

where $K_o$=0.07, interference by ester; $A_s$=absorbance at 233 nm; b=cuvette length=1 cm; c=concentration of sample=300 g/L.

Tocopherol Content

Analysis of tocopherols used a modified high performance liquid chromatography ("HPLC") procedure of Carpenter, "Determination of Tocopherols in Vegetable Oils," *J. Am. Oil Chem. Soc.*, 66:668–671 (1979), which is hereby incorporated by reference. The HPLC system consisted of a Water's Model 510 HPLC pump (Water's Associates, Inc., Milford, Conn.), a Water's Model U6K injector, a Shimadzu Model RF-530 fluorescence detector (Shimadzu Scientific Instrument, Columbia, Md.), and a Shimadzu Model C-R6A data processor. Tocopherols were separated on a 300×3.9 mm Bondclone 10 $\mu$M diam silica column (Phenomenex, Torrance, Calif.) with 1.5% of isopropanol in hexane at a flow rate of 1.6 mL/min. Tocopherols were detected at an excitation wavelength of 295 nm and emission wavelength of 335 nm. standard tocopherol solutions were made by dissolving ($\alpha$-, $\gamma$-, and $\Delta$-tocopherol (Sigma chemical Co., St. Louis, Mo.) in hexane and making a series of dilutions to obtain final concentrations of 0.1428, 0.0071, and 0.3571 mg/mL, respectively. One gram of the oil sample was diluted to a final volume of 10 mL with the eluting solvent. The diluted oil sample (10 $\mu$L was injected into the HPLC and analyzed under the same conditions as the standard tocopherol mix. The concentration of each tocopherol in the oil was determined by Equation 12.

Equation 12:

$$\text{Tocopherol (mg/100 g oil)} = \frac{\text{Area}_{\text{sample}} - x}{y} \times 10^{-1}$$

were x=608 and y=976 for α-tocopherol; x=2566 and y=1423.5 for γ-tocopherol; and x=328 and y=1308.6 for Δ-tocopherol.

Positive identification was made by matching the retention time of the component peak in the oil sample with that of the standard tocopherol. Linear regression of the peak areas on the HPLC chomatogram with respect to the amounts of injected standard determined with tocopherol concentrations of the oil sample. The destruction of tocopherols is the loss of all tocopherols in an oil during the instrument test and was calculated as the percentage loss of the original total tocopherol concentration.

Dielectric Constant

The dielectric constant was determined by using the Food Oil Sensor ("FOS") Model NI-20 (Northern Instrument Corp., Lino Lakes, Minn.). The FOS reading of the oil sample was used to indicate the dielectric constant of the oil. The FOS was calibrated to a zero reading with the fresh oil for each treatment before the instrument tested oil samples were measured.

Other Tests

Fresh soybean oils with different iodine values (70, 94, 110 and 132) and the soybean oil (IV=94) containing no additives, 5 ppm DMS, 1000 ppm TBHQ, and both 5 ppm DMS and 100 ppm TBHQ were all analyzed for oil stability index. Samples of soybean oil containing 100 ppm TBHQ and both 5 ppm DMS and 100 ppm TBHQ, before and after the instrument test, were analyzed for level of TBHQ.

5. Statistical Analysis

For the performance of the instrument 20, the means of the dependent variables, including induction time and linear slope, were analyzed statistically as functions of the independent variables, including replication (n=3), oil temperature setting (n=3), water temperature setting (n=3), and the interaction of the oil temperature and water temperature settings. Throughout this study, analysis of variance was done using the General Linear Model ("GLM") procedure in SAS® (SAS Institute Inc., SAS® User Guide: Basics, Version 5 Edition, Cary, N.C.: SAS Institute Inc. (1985), which is hereby incorporated by reference). Also, the least-squares means for independent variables were obtained; the significantly different means were identified by the PDIFF option of the GLM procedure with a probability level of 5% except where other levels are designated.

Coefficient of variations ("CV") or the precision for the induction time and linear slope from the instrument test were determined. The CV were determined individually by dividing the standard deviation by the least-squares mean and were used to indicate the precision performance of the instrument 20. The combination of oil temperature and water temperature settings, at which the minimum CV of linear slope and induction time were obtained, was selected as the optimum conditions for the instrument test. Also, the average water temperature and oil temperature for each instrument test were recorded by PC. The mean water temperature and CV across all oil temperature settings were determined for each water temperature setting. Likewise, the mean oil temperature and CV across all water temperature settings were determined for each oil temperature setting.

For the effects of unsaturation on the oxidative stability of oils measured by the instrument tests, the dependent variables (induction time and linear slope) were analyzed as a function of replication (n=3) and unsaturation level (n=4). To measure the effects of unsaturation levels of oils on the chemical changes occurring in the trap solution, dependent variables such as concentration of different VFA (C1–C7) were analyzed as functions of replication (n=3) and unsaturation level (n=4). To measure the effects of unsaturation levels of oils on the chemical changes occurring in the oils tested by the instrument 20, the dependent variables, including TPC, FFA, fatty acid profile, FOS, and tocopherol contents, were analyzed as a function of replication (n=3) and the effect of instrument test (fresh vs tested; n=2) and unsaturated levels (n=4). Since there was only one measurement of oil stability index with respect to each unsaturation level, no statistical analysis was performed for this variable.

For the effects of additives on oxidative stability of an oil, the dependent variables (induction time and linear slope) were analyzed as functions of replication (n=3) and additive treatment (n=4), which included the control oil and the oils treated with 5 ppm DMS, 100 ppm TBHQ, or both DMS and TBHQ. For effects of additives on the chemical changes occurring in the trap solution, dependent variables such as concentrations of different VFA (C1–C7) were analyzed as functions of replication (n=3) and additive treatment (n=4). For effects of additive on the chemical changes occurring in the oils tested by the instrument 20, the dependent variable dielectric constant (FOS reading) was analyzed as functions of replication (n=3) and additive treatment (n=4). The dependent variables, including TPC, FFA, fatty aid composition, and tocopherol contents, were analyzed as functions of replication (n=3) and additive treatment (n=5), which included the untested control oil in addition to the treatments mentioned previously in order to provide the baseline comparison.

The overall accuracy of the instrument 20 was determined by the correlation between the induction time (n=18) and linear slopes (n=18) of the oils measured by the instrument 20 with their oil stability index values (n=6) using the Regression ("REG") procedure in SAS® (SAS Institute Inc., SAS® User Guide: Basics, Version 5 Edition, Cary, N.C.: SAS Institute Inc. (1985)). Since the Oil Stability Instrument detected little difference in OST at 110° C. between the control oil and the oil treated with DMS, this data set was omitted.

RESULTS AND DISCUSSION

1. Optimization of the Instrument

The measurements of the instrument 20 are discussed before the selection of the optimum parameters of the instrument 20 operation in order to understand their significance. Optimum operation parameters, oil and water temperature settings, were determined as the combination of set temperatures giving the best precision or lowest coefficients of variation ("CV") for the instrument 20 measurements. Volatile compounds, including volatile fatty acids, produced by oils during instrument test and trapped in HPLC-grade deionized water (trap solution), will be discussed to explain the measurements of the instrument 20 from the chemical point of view.

Measurements of the Instrument

Figure 3:
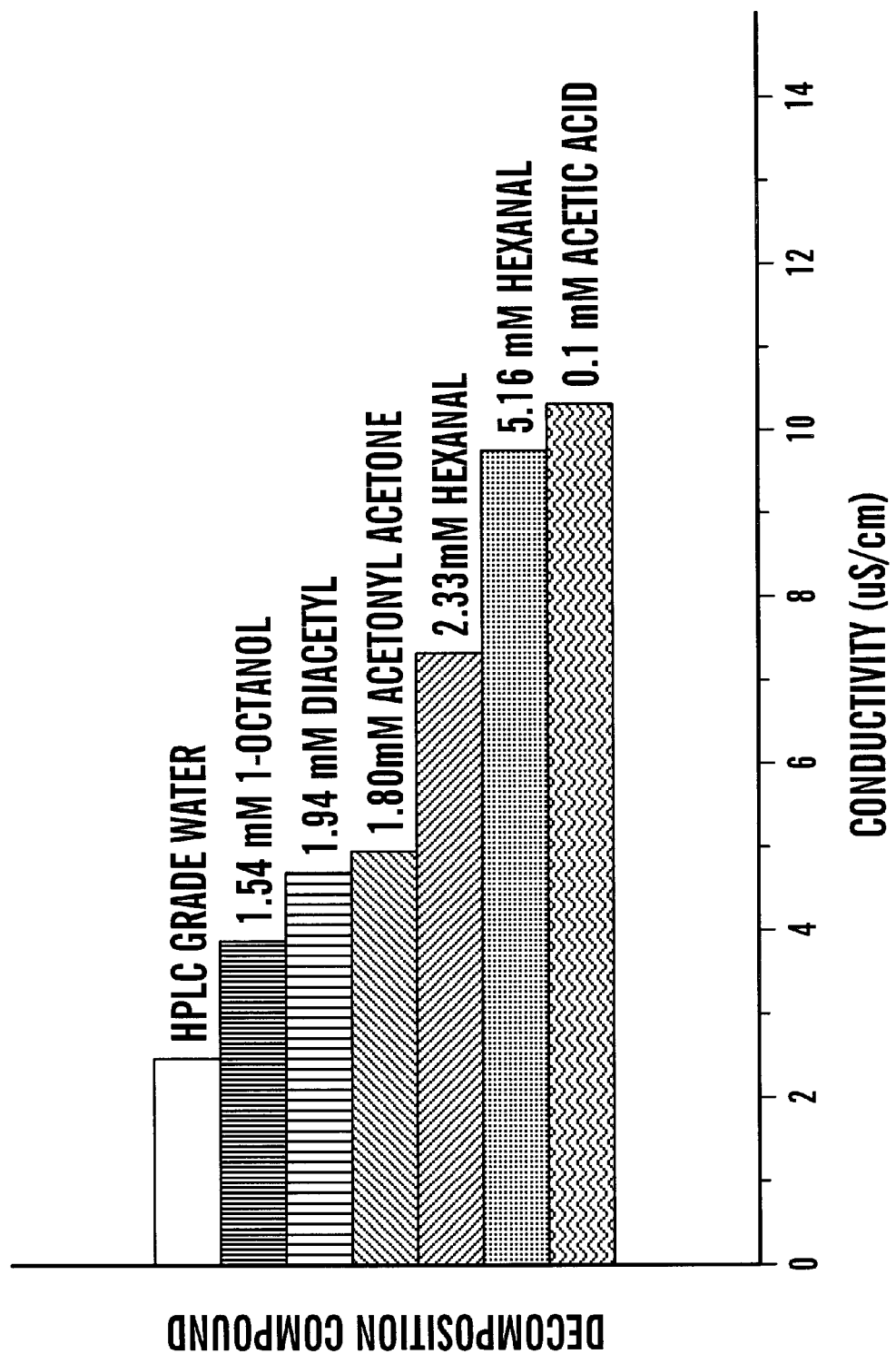
FIG. 3 is a graph showing the conductivity of typical oil decomposition compounds measured by the instrument conductivity sensor.

It is important to understand what causes the conductivity of the trap solution to increase during the test. The conductivities of different aqueous concentrations of compounds such as an acid, alcohol, ketone, and aldehyde are showing in FIG. 3. These compounds are typical volatile decomposition products ("VDP") that occur during fat/oil oxidation. Conductivity in a trap solution of each compound was measured individually by the conductivity sensor of the instrument 20. In general, the greatest increase in conductivity of the trap solution was due to acetic acid followed by hexanal. Conductivity of acetic acid and hexanal solutions increased as their concentrations in the trap solutions increased. Di-ketones and alcohol increased conductivity of their respective solutions, but to a much lesser degree than the acid. Therefore, the increase of VDP during the progress of fat/oil oxidation can be indicated by the conductivity of the deionized water solution in which the VDP are trapped.

Figure 4:
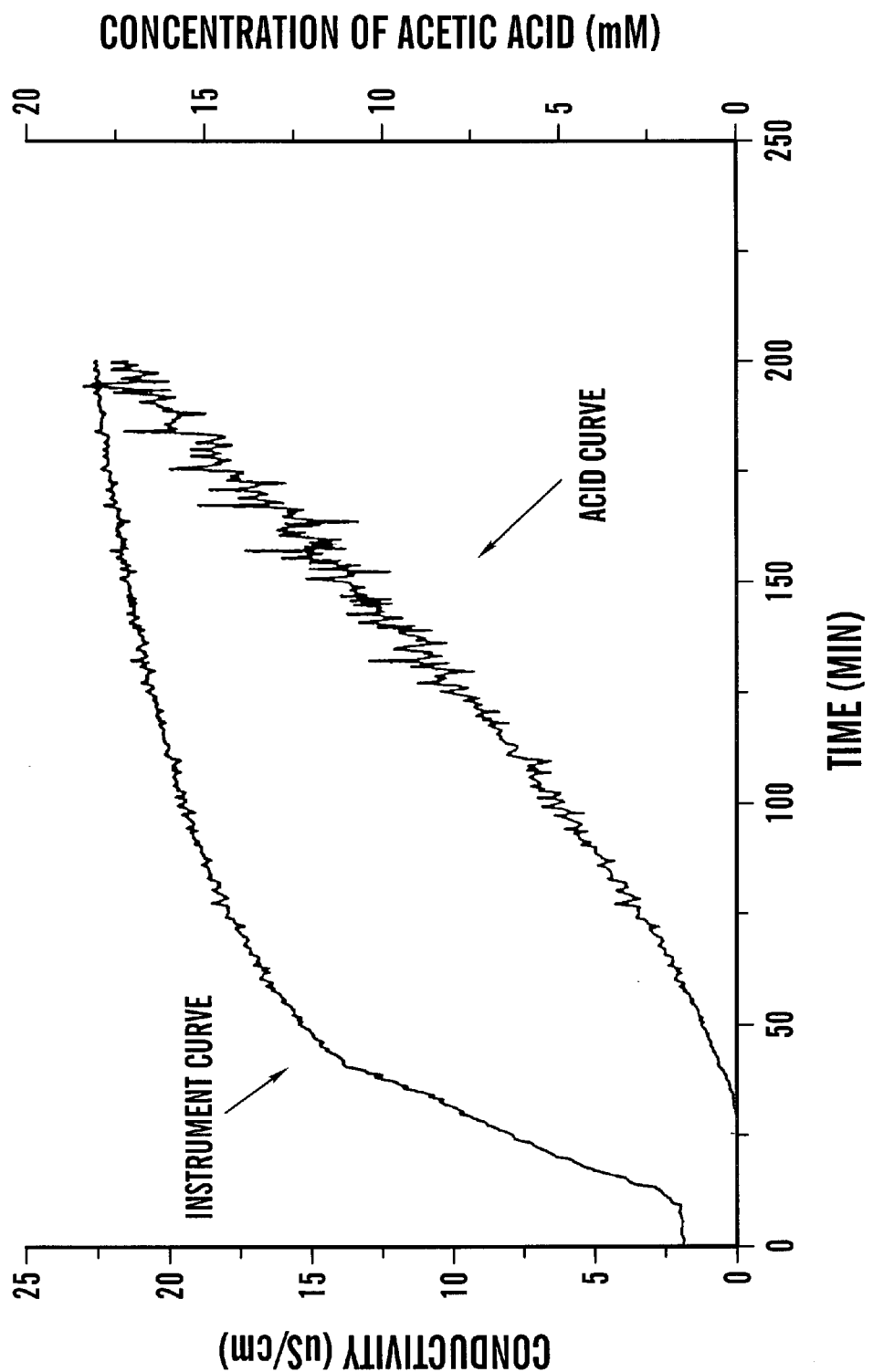
FIG. 4 is an instrument curve of soybean oil (IV=110) and the corresponding acetic acid curve measured by the instrument.
Figure 5:
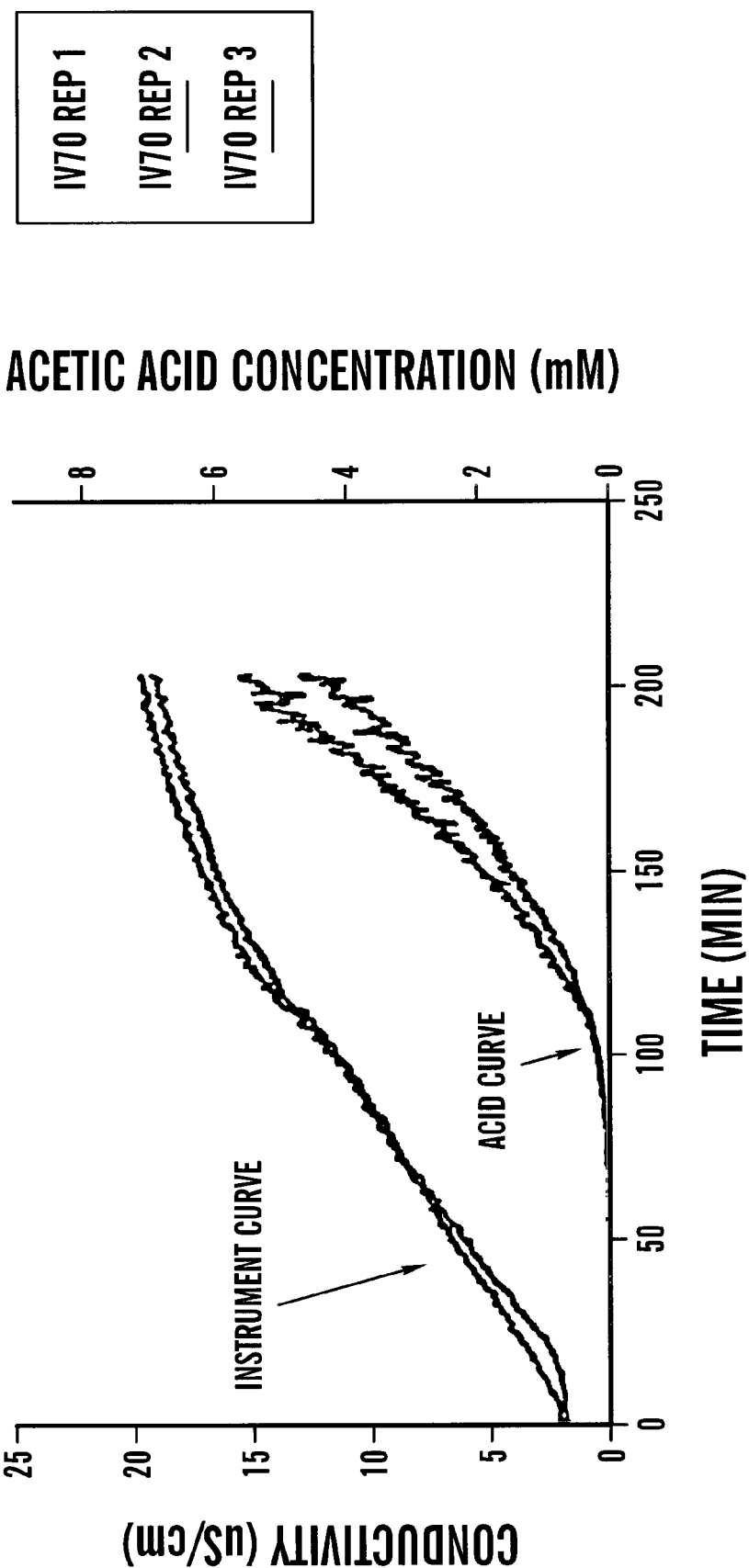
FIG. 5 is an instrument curve of soybean oil (IV=70) and the corresponding acetic acid curve measured by the instrument.

The measurements of the instrument 20 can be explained by the instrument curves and the acid curves. Typical instrument curves and typical acid curves of soybean oil (IV=110 and 70) are shown in FIGS. 4 and 5. The instrument curve was fitted to a third order polynomial function, with respect to the time of the measurements. After a short period of holding at an initial level, the conductivity of the trap solution increased rapidly and then tended to level off at 21 $\mu$S/cm.

The conductivity value for the trap solution was converted to acid concentration according to the calibration of the instrument 20 conductivity probe 13 with a series of acetic acid solutions; this calibration showed an exponential regression between the conductivity and different concentrations of the acid solutions. The linear slope of the conductivity from 3.5 to 11 $\mu$S/cm in the trap solution with respect to time represented the formation speed and collection of the VDP in the trap solution. The linear slope thus was selected as one of the instrument measuring parameters. A plot of the acid concentration with respect to time, which formed the acid curve, is shown also in FIG. 4. A typical oil oxidation pattern was observed in the shape of the acid curve (FIG. 4), which includes two phases, a lag phase and a log phase. The lag phase was the initial holding period before the oil sample started producing noticeable amounts of acids that were trapped in the trap solution during the instrument test. After passing the lag phase, the acid concentration started increasing rapidly; this indicated the log phase of oil oxidation. The lag phase can be referred to as the initiation stage of lipid oxidation, whereas the log phase corresponds to the propagation stage of lipid oxidation. The point where the lag phase passed into log phase was determined to be 0.2 mM of acid concentration by the change in the linear slope. The slope of the linear regression between the acid concentration and time on the acid curve increased by a 29.34 fold after surpassing this concentration. Therefore, the time to reach 0.2 mM acetic acid concentration on the acid curve was determined as the induction time, another parameter of the instrument measurements.

In consideration of both the instrument curve and the acid curve shown in FIG. 4, the linear slope indicates the formation rate of VDP during the initiation stage of lipid oxidation. The formation of VDP with respect to time during the initiation stage of lipid oxidation is linear and is inversely proportional to the oxidative stability of a lipid. The induction time indicates the duration of the initiation stage of the oil sample during oxidation under the instrument test conditions and is directly proportional to the oxidative stability of the oil.

Selection of the Optimum Instrument Operation Parameters

The optimum operation parameters for the instrument 20 were determined by selecting the combination of oil temperature and water temperature settings that had the minimum CV among all oil temperature and water temperature setting combinations. The linear slopes and induction times of sunflower oils and their corresponding CV analyzed at different combinations of oil temperature and water temperature settings are shown in Table 3 and 4, respectively. The lowest CV of linear slope and induction time were obtained by setting the oil temperature setting at 160° C. and the water temperature setting at 50° C. for the instrument measurement. Operating under such conditions, the instrument 20 had CV of 2.72% and 2.37% for linear slope and induction time measurements, respectively. According to Smith, "Evaluation of Analytical Data," Ch. 4 in *Introduction to the Chemical Analysis of Foods,* S. S. Neilsen (Ed.), Boston, Mass.: Johns and Bartlett, Inc., pp. 54–65 (1994), which is hereby incorporated by reference, an instrument measurement with a CV of 5% or less is considered to be precise. Therefore, the instrument 20 of the present invention may be classified as a precise instrument under such a guideline.

The precision of the instrument 20 also can be explained by the low CV of linear slope and induction time under the optimum operation conditions and high coefficients of linear regression ("R-square") of the instrument curves. The mean of R-squares of the linear regression lines for obtaining the linear slopes of the sunflower oils tested by the instrument 20 under the optimum conditions was 0.97 with a CV of 1.14%. The high R-square (97%) indicates that linear regression very adequately explains the instrument curve. The low CV (1.14%) indicates that the results of such a linear regression of the instrument curves are highly reproducible The analyses of variance for the effects of oil temperature, water temperature setting, their interactions, and replication on the linear slope and induction time of the sunflower oils measured by the instrument 20 are shown in Appendix B-1. The linear slope and induction time of sunflower oil tested by the instrument 20 were different (P<0.05) among the oil temperature settings.

The mean linear slopes and induction time of the sunflower oils measured by the instrument 20 with respect to the oil temperature setting are also shown in Table 3 and Table 4, respectively. The linear slope of sunflower oil increased as the oil temperature setting of the instrument 20 increased. Generally speaking, a chemical reaction rate increases with the increased reaction temperature (Barrow, *Physical Chemistry,* Halliday Litho Corp., Carmel Valley, Calif. (1973), which is hereby incorporated by reference). Higher oil temperature settings increased the oxidative reaction rates and favored the formation of VDP during the instrument test so that the linear slope of the oil increased.

TABLE 3

Least-squares means (n = 3) and coefficients of variation (CV) of linear slope (LS)[a]
for sunflower oil determined at different water temperature and oil temperature settings
by the instrument 20 and the overall least-squares means across water temperature settings

| | Oil temperature (° C.) | | | | | |
|---|---|---|---|---|---|---|
| | 160 | | 175 | | 190 | |
| Water temperature (° C.) | LS ($\mu$S/cm-min) | CV (%) | LS ($\mu$S/cm-min) | CV (%) | LS ($\mu$S/cm-min) | CV (%) |
| 40 | 0.2078 | 11.12 | 0.2650 | 20.58 | 0.3280 | 17.48 |
| 50 | 0.2131 | 2.72 | 0.2647 | 12.07 | 0.3409 | 14.15 |
| 60 | 0.1983 | 13.21 | 0.2429 | 19.91 | 0.3070 | 17.24 |
| Overall Lsmean[b,c] | 0.2064 c | | 0.2575 b | | 0.3253 a | |

[a]Linear slope of conductivity between 3.5 and 11 $\mu$S/cm versus time (min) from instrument curves.
[b]N = 9.
[c]Overall LSmeans followed by unlike letters are different ($P < 0.05$).

TABLE 4

Least-squares means (n = 3) and coefficients of variation (CV) of
induction time (IT)[a] for sunflower oil determined at different
water temperature and oil temperature settings by the instrument 20
and the overall least-squares means across water temperatures

| | Oil temperature (° C.) | | | | | |
|---|---|---|---|---|---|---|
| Water temperature (° C.) | 160 | | 175 | | 190 | |
| | IT (min) | CV (%) | IT (min) | CV (%) | IT (min) | CV (%) |
| 40 | 53.58 | 13.66 | 44.98 | 15.96 | 36.74 | 9.13 |
| 50 | 48.83 | 2.37 | 41.04 | 10.22 | 34.95 | 11.57 |
| 60 | 51.77 | 15.30 | 45.46 | 12.20 | 34.78 | 16.28 |
| Overall Lsmean[b,c] | 51.39 a | | 43.83 b | | 35.49 a | |

[a]Time to reach a conductivity equal to 0.2 mM acetic acid in trap solution during instrument test.
[b]N = 9.
[c]Overall LSmean followed by unlike letters are different ($P < 0.05$).

The induction time of sunflower oil measured by the instrument 20 decreased as the oil temperature setting increased; higher oil temperature settings reduced the duration of the initiation stage of lipid oxidation. The observation agreed with Hasenhuettl, who reported that the reduction of oil stability index values of the oils measured by the Metrohm Rancimat with respect to the increase of the oil temperature can be described by an exponential regression equation up to 140° C. of the oil temperature. Most of the oils analyzed by the latter researchers had oil stability index values higher than 10 hr at 100° C. oil temperature; those values decreased to less than 2 hr when the oils were analyzed, at 140° C. The mean induction time of the sunflower oils analyzed at 160° C. was 51.39 min and approached the magnitude of the oil stability index values at 140° C. reported by Hasenhuettl.

The instrument 20 has many different features in comparison to those of Rancimat or Oil Stability Instrument, even though the shape of the instrument curve was similar to that of the Rancimat curve observed by Hasenhuettl at 150° C. oil temperature. They noted that when the oils were analyzed at 150° C. by the Rancimat, the curves appeared to be concave and inverted downward, making determination of oil stability index difficult. The instrument 20 can measure the oxidative stability of oil at a higher temperature than the Rancimat or Oil Stability Instrument because of its design. First of all, the instrument 20 uses a more sensitive conductivity probe than the Rancimat or Oxidative Stability Instrument. The sensitivity probe of the instrument 20 measures 0 to 22 $\mu$S/cm conductivity and has a linear response to the conductivity between 0 and 11 $\mu$S/cm. According to AOCS, *Official and Tentative Methods of Analysis of the American Oil Chemists Society*, American Oil Chemists Society, Champaign, Ill. (1993), Official Method Cd 12b-92, the sensitivity probe of the Oil Stability Instrument has a full-scale of 300–500 $\mu$S/cm, which is much higher than that of the instrument 20. Second, the instrument 20 monitors the progression of lipid oxidation in a different manner than the Rancimat or Oil Stability Instrument. The conversion of the conductivity values into acid concentration by the instrument 20 interprets the oxidative measurement from the view point of progression of the oxidation reaction, which clearly indicates the turning point between the initiation and the propagation stages of lipid oxidation. Third, the linear slope of the instrument 20 measures the formation speed of VDP from the oil degradation during the initiation stage of the lipid oxidation, while the Rancimat and Oil Stability Instrument do not include such a measurement. However, whether the linear slope indicates the oxidative stability of lipid more accurately than the induction time of the instrument 20 or oil stability index remains to be studied.

Moisture levels bubbled into the oil sample did not affect the linear slope and induction time of sunflower oils measured by the instrument 20. The hydrolysis reaction occurring in the oil during the instrument test due to the moisture in the air stream did not affect the linear slope and induction time of the instrument 20 measurements. However, the moisture level did affect the reproducibility of the instrument 20 measurements. The reason for this effect remains to be explored.

The Performance of the Instrument

The control system of the instrument 20 accounts for its performance for the oxidative stability measurement. Two major variables, the oil temperature and water temperature were controlled by the instrument 20, while the air flow rate was controlled manually. Because the actual air flow rate was not monitored by the PC 18 in this study due to the unavailability of the equipment, only the actual oil sample temperature and water temperature were monitored during the instrument test. The mean oil and water temperatures and their CV during the instrument test of the sunflower oils at different oil temperature and water temperature settings are listed in Table 5. The actual oil and water temperatures fluctuated approximately 2.5° C. and 0.4° C., respectively, from the set points. The instrument 20 exerted more control over the water temperature than over the oil temperature.

The performance of oil temperature control by the instrument 20 was limited by many factors. The efficiency of the hot plate 9, the heat transfer between the glassware and the hot plate 9, and the heat exchange of the hot plate 9 and glassware with the environment contributed to the temperature variation from the set point. The water in the instrument 20 was heated by an immersion heater 4, which provided heat to the water by direct contact; this improved the heat transfer efficiency of the water control. The instrument 20 did not use direct heating to control the oil temperature in order to prevent an over-heating problem that could occur at the heater-oil interface around the immersion heater; this would lead to gumming and polymerization of the oil surrounding the heater. In general, the temperatures of the oil sample and water were controlled adequately by the instrument 20 because all CV of temperatures were less than 2%; this indicated a highly repeatable temperature pattern.

TABLE 5

The mean temperatures[a] and coefficients of variation (CV) of sunflower oil samples and water during the instrument tests.

| Oil temperature | | | Water temperature | | |
|---|---|---|---|---|---|
| OTS (° C.)[b] | (° C.)[c] | CV (%) | WTS (° C.)[b] | (° C.)[c] | CV (%) |
| 160 | 160.6 | 1.9 | 40 | 40.6 | 0.9 |
| 175 | 175.6 | 1.8 | 50 | 50.5 | 0.7 |
| 190 | 190.3 | 1.6 | 60 | 60.5 | 0.7 |

[a]N = 9.
[b]OTS = oil temperature setting on personal computer and WTS = water temperature setting on personal computer.
[c]Average recorded temperature for oil and water during instrument tests.

Recovery of Volatile Fatty Acids during Analysis

The recovery rate of different volatile fatty acids (VFA) in DW collected after the instrument test and analyzed by the proposed VFA analysis method are shown in Table 6. In general, the recovery rate increased as the molecular weight of the VFA decreased. The low solubility of the six- and seven-carbon VFA, such as isocaproic, caproic, and heptanoic acids in DW, may account for the loss of some VFA in the concentrating process during the VFA analysis. Since formic and acetic acids could not be separated by the GLC method in this study, both acids were counted as one group.

All CV of the recovery rate of VFA were less than 5% except for the CV for acetic acid (5.7%). Such low CV of VFA analysis indicated that the proposed VFA analysis method was precise. The recovery rates for isocaproic, n-caproic, and heptanoic acids are less than 95%, which is the minimum requirement for an accurate analytical method (Pomeranz et al., Food Analysis: Theory and Practice, 2nd ed., New York: Van Nostrand Reinhold Co. (1987), which is hereby incorporated by reference). However, because this VFA analysis method is precise, it is appropriate to make this method accurate by compensating for the loss of VFA during the analysis by a correction factor. By taking into consideration the high recovery rates and low CV of the VFA analysis and the compensation for accuracy during calculation, this VFA analysis method has been proven to be an accurate and precise method.

TABLE 6

The mean recovery rates and coefficients of variation ("CV") of different volatile acids in HPLC grade deionized water collected during the instrument test by the proposed VFA analysis method.

| Voltaile fatty acid | Recovery (%)[a] | CV (%) |
|---|---|---|
| Formic + Acetic | 102.0 | 5.7 |
| Propionic | 99.8 | 2.9 |
| Isobutyric | 98.7 | 1.4 |
| Butyric | 98.9 | 1.8 |
| n-Valeric | 97.0 | 1.0 |
| Isocaproic | 91.0 | 1.1 |
| n-Caproic | 90.2 | 1.6 |
| Heptanoic | 75.5 | 4.1 |

[a]N = 4.

Effects of Oil Temperature and Water Temperature Settings on the VFA in the Trap Solution The analyses of variance for the effects of oil temperature and water temperature settings on the concentrations of VFA in the trap solution collected from sunflower oils during the instrument test are shown in Appendix B-2. Only the concentrations of caproic acids and total VFA contents in the trap solutions were different (P<0.05) among the oil temperature settings. The concentration of each VFA and the total VFA contents in the trap solution were not affected by the water temperature settings. In other words, the moisture level bubbled into the oil sample did not have an effect on production of VFA by the oil during the instrument test.

The mean concentrations of the VFA and total VFA with respect to the oil temperature setting are shown in Table 7. Formic, acetic, valeric, caproic, and heptanoic acids, as well as one unknown VFA, were quantified in this experiment. Among all the VFA, formic and acetic acids were the most abundant acids among all the VFA since these acids accounted for more than 49% of the total VFA in all cases. This finding agreed with findings of deMan, who reported that the volatile acids produced by several oils in the receiving water during the Rancimat test were composed mainly of formic acid and significant amounts of acetic acid. There was a trend for the levels of formic and acetic acids in the trap solutions at 190° C. oil temperature setting to be significantly higher than in the trap solutions at 160° C. oil temperature setting. The caproic acid in the trap solution at 190° C. was significantly higher (P<0.05) than at the lower temperatures (Table 7). Caproic acid was the second most abundant VFA, next to the formic and acetic acid group of all the VFA collected from the sunflower oil. This observation agreed also with that reported by deMan, who noted that the concentration of caproic acid collected from the sunflower oil in the receiving water during the Rancimat test was even higher than that of acetic acid. High oil temperature increased the oil production of VFA which were collected in the trap solution during the instrument test.

The total VFA concentration was measured by both GC and titration methods. The total VFA level measured by the titration method was higher than that measured by GC; this discrepancy may be due to three reasons. First, the end point of the titration as indicated by the phenolphthalein reagent was between pH 8 and pH 10, which was already beyond the neutral range; this may cause on over-titration error. Second, some VFA were not identified, and thus not quantified, in the GC analyses. Third, other VDP besides acids may contribute to the titratable acidity. However, the titration method did not distinguish between the level of total VFA collected at 160° C. and that collected at 175° C., but the total VFA in the trap solution determined by the GC method increased (P<0.05) as the oil temperature increased (Table 7).

TABLE 7

Least-squares mean concentrations[a,b] of volatile fatty acids (VFA) produced by the sunflower oil and trapped in deionized water tested by the instrument 20 at different oil temperature settings (OTS).

| Volatile fatty acid (mM) | OTS | | |
|---|---|---|---|
| | 160° C. | 175° C. | 190° C. |
| Formic Acid + Acetic Acid | 0.1131 | 0.1152 | 0.1246 |
| Valeric Acid | 0.0071 | 0.0065 | 0.0083 |
| Caproic Acid | 0.0297[b] | 0.0426[b] | 0.0867[a] |
| Heptanoic Acid | 0.0070 | 0.0042 | 0.0066 |
| Unknown | 0.0096 | 0.0244 | 0.0222 |
| Total VFA by GC | 0.1769[c] | 0.1915[b] | 0.2522[a] |
| Total VFA by titration | 0.96[b] | 1.12[b] | 1.44[a] |

[a] N = 3
[b] For any one dependent variable, means followed by unlike letters are different ( P < 0.05).

2. Effects of Oil Unsaturation Levels on Instrument Measurements and Quality of the Tested Oil The Effects of Unsaturation Levels on the Instrument Measurements The analyses of variance for the effect of oil unsaturation level, represented by the iodine value (IV), and replication on the linear slope and induction time of the instrument 20 measurements are shown in Appendix B-3. The mean linear slope and induction time of soybean oils with different IVs were different (P<0.05). The mean linear slope and induction time of the soybean oils were not different among the replications; this indicated that the measurements of the instrument 20 were consistent from time to time.

The linear slope and induction time of soybean oils with different IVs are shown in Table 8. The linear slope of soybean oil increased (P<0.05) as IV increased. The linear slope of each soybean oil was different (P<0.05) from the other; this demonstrated that the instrument 20 has the sensitivity to differentiate between oils of different unsaturation levels. The unhydrogenated soybean oil (IV=132) had the highest linear slope of all oils; linear slope decreased as the hydrogenation level of the soybean oil increased. The linear slope measured the formation rate of VDP by the oil during the initiation stage of oxidation; this rate directly measured the oxidation rate of the oils. The higher the linear slope of an oil measured by the instrument 20, the less stable the oil is. According to Lin, the oxidation rate of a fat/oil is roughly proportional to the degree of unsaturation; the greater the degree of unsaturation, the greater the oxidation rate.

Increase in unsaturation of the oil reduced the induction time of the oil tested by the instrument 20. The induction time of soybean oil ranged from 95.5 min for the most saturated oil (IV=70) to 32.4 min for the most unsaturated oil. The induction time of each oil was different (P<0.05) from the others; the oxidative stability of soybean oils with different unsaturation levels was well differentiated by the induction time of the instrument 20 measurement. Stable oil has a longer induction time than an unstable one. The induction period of fat oxidation refers to the time period before the peroxide content of the fat begins to increase. The peroxidation of the free radical may have already begun during the induction period. The formation of the peroxides during this period was relatively small, and the peroxide formation rate is equivalent to its breakdown, thus no detectable increase in the peroxide value occurred. After the induction period, the peroxide content of the fat began to rise rapidly. (Frankel et al., "Automatic Determination of Oxidation Stability of Oil and Fatty Products," *Food Technol.*, 35:71–76 (1982); Perkins, "Formation of Non-Volatile Decomposition Products in Heated Fats and Oils," *Food Technol.*, 21:611–616 (1967), which are hereby incorporated by reference).

The induction time of the unhydrogenated soybean oil (IV=132) analyzed by the instrument 20 agrees with those of Hasenhuettl and Reynhout. Hasenhuettl reported that the induction time of RBD soybean oil (unhydrogenated) analyzed by the Rancimat at 140° C. was about 2 hr. The mean induction time of the unhydrogenated soybean oil measured by the instrument 20 at 160° C. was 32.4 min, which may become 128.8 min at 140° C. if the induction time is converted to a lower temperature using the oil stability index conversion factor between temperatures. According to Reynhout, the induction time of a soybean oil analyzed by the Rancimat at 160° C. was estimated to be 24 min, which is close to that of the unhydrogenated oil analyzed by the instrument 20 (32.4 )min).

The oil stability index at 110° C. measured by the Oil Stability Instrument for the oils with IVs of 70, 94, 110, and 132 were 268, 17.6, 7.8, and 5.5 hr, respectively. The distribution patterns of the induction time of soybean oils measured by the instrument 20 were similar to those of the oil stability index values for the same oils; however, the instrument 20 required less time than the Oil Stability Instrument. The CV of all linear slopes and induction time of soybean oils tested by the instrument 20 were less than 10% and 15%, respectively, except for the CV of linear slope of the unhydrogenated soybean oil which was 20.2%. These data indicated that the instrument 20 needs improvement to obtain more precise measurements particularly covering the wide range of oil unsaturation levels tested. The CV of the instrument 20 measurements may be improved with some modifications, which will be discussed later.

TABLE 8

Least-squares means[a,b] and coefficients of variations (CV) for linear slope and induction time determined by the instrument 20 for soybean oils with different degrees of unsaturatin as measured by iodine value ("IV").

| Degree of unsaturation (IV) | Linear slope ($\mu$S/cm · min) | CV (%) | Induction time (min) | CV (%) |
|---|---|---|---|---|
| 70 | 0.1169[d] | 9.23 | 95.94[a] | 0.94 |
| 94 | 0.2362[c] | 5.19 | 49.75[b] | 5.95 |
| 110 | 0.3108[b] | 2.97 | 39.05[c] | 1.65 |
| 132 | 0.4524[a] | 20.19 | 32.39[d] | 14.42 |

[a] N = 3.
[b] For any one dependent variable, means followed by unlike letters are different (P < 0.05).

The Effects of Oil Unsaturation Levels on the VFA in the Volatile Trap Solution

The analyses of variance for the effects of oil unsaturation levels ("IVs") and replication on the concentration of VFA trapped in DW from the soybean oils during the instrument test are shown in Appendix B-4. Formic, acetic, propionic, butyric, valeric, caproic, and heptanoic acids and one unknown were found in the DW trap. The concentration of each VFA identified in this study was different (P<0.05) among oils of different degrees of unsaturation but not among replications.

The mean concentrations of VFA from oils with different IVs and collected in the volatile trap are listed in Table 9. The compositions of VFA in the trap solutions were slightly different among IV levels of the soybean oils. A small amount of heptanoic acid was detected only in volatiles trapped during testing the most saturated oil (IV=70). Butyric acid was found in the volatile trap for all oils except for the unhydrogenated soybean oil. The most saturated oil produced the lowest levels of formic and acetic acids. The concentrations of propionic, butyric, valeric, and caproic acids in the volatile traps were different (P<0.05) among all IVs of the soybean oils; however, the distribution patterns of these VFA did not follow any trend with respect to the IV.

The concentration of the unknown peak found in the trap was calculated by using the RRx of the acetic acid standard. The concentration of the unknown peak in the volatile trapping products from the most saturated oil was smaller (P<0.05) than that trapped from the oils with IVs of 110 and 132. The concentration of the unknown peak in the oil with an IV of 94 was not different from that in the trap solution for the soybean oil with an IV of 110. The concentration of the unknown acid in the trapped VDP produced by the most unsaturated oil (IV=132) was much higher than that in trapped VDP for other oils and was about three times more abundant than the formic and acetic acids. This observation was not consistent with earlier findings in this study; the formic and acetic acids were the most abundant of all VFA. The unknown peak may be a VDP produced from degradation of the C18:3 with the unhydrogenated soybean oil.

The total VFA concentrations were differentiated (P<0.05) by the IVs except that the total VFA level trapped from the oil with an IV of 94 was not different from that trapped from the oil with an IV of 110. In general, the total VFA in trap solutions increased (P<0.05) as the IV of the oil increased. Total production of trapped VFA by the oil during 200 min of the instrument test relates to the formation rates of VDP in the oil during oxidation since VFA are tertiary products of lipid oxidation (Frankel, "Lipid Oxidation," *Lipid Res.*, 19:1–22 (1980), which is hereby incorporated by reference). Therefore, the total VFA in trap solution is proportional to the oxidative stability of the oil. As suggested by the total VFA level in the traps, the oxidative stability of the soybean oils is rated according with the IVs of the oils; increase of unsaturation level (IV) in oil decreases its oxidative stability. This result is consistent with the linear slopes and induction times of the same oils measured by the instrument 20.

The distribution pattern of total VFA among different IVs of the soybean oils agreed with that of linear slopes of the same oils as tested by the instrument 20. In other words, the oil sample with the higher conductivity formation rate (higher linear slope) measured by the instrument 20 yielded larger amounts of VFA in the volatile trap than the lower linear slope.

TABLE 9

Least-squares mean concentrations[a,b] of volatile fatty acids (VFA) produced by instrument-tested soybean oils with different iodine values (IVs) and trapped in the volatile trap solution

| Volatile fatty acid (mM) | Degree of unsaturation (IV) | | | |
|---|---|---|---|---|
| | 70 | 94 | 110 | 132 |
| Formic + Acetic Acids | 0.1644 b | 0.2879 a | 0.3072 a | 0.2736 a |
| Propionic Acid | 0.0134 b | 0.0214 a | 0.0208 a | 0.0158 b |
| Butyric Acid | 0.0098 b | 0.0195 a | 0.0082 b | — |
| Valeric Acid | 0.0104 b | 0.0153 a | 0.0111 b | 0.0042 c |
| Caproic Acid | 0.0165 b | 0.0281 a | 0.0194 b | 0.0188 b |
| Heptonic Acid | 0.0048 | — | — | — |
| Unknown | 0.0258 c | 0.0446 bc | 0.1136 b | 0.8001 a |
| Total VFA[c] | 0.2471 c | 0.4167 b | 0.4803 b | 1.1124 a |

TABLE 9-continued

Least-squares mean concentrations[a,b] of volatile fatty acids (VFA) produced by instrument-tested soybean oils with different iodine values (IVs) and trapped in the volatile trap solution

| Volatile fatty acid (mM) | Degree of unsaturation (IV) | | | |
|---|---|---|---|---|
| | 70 | 94 | 110 | 132 |

[a]N = 3.
[b]For any one dependent variable, means in a row followed by unlike letters are different (P < 0.05).
[c]Total VFA is the summation of the VFA measured by the GC method.

Quality of the Oils after the Instrument Test
Total Polar Components

The analyses of variance for the effects of replication, IV, treatment, and the interactions of IV and treatment on the TPC of the instrument-tested oils are shown in Appendix B-5. The mean TPC levels of soybean oils were different among the IV, treatment, and the interaction of IV and treatment. Oils with different unsaturation levels yielded different (P<0.05) amounts of TPC during the instrument test. The level of TPC in the oils increased (P<0.05) during the instrument test.

The rapid TPC method separated the non-polar components ("NPC") from the polar components in the oil according to the results of TLC analysis (AOCS, *Official and Tentative Methods of Analysis of the American Oil Chemists Society*, American Oil Chemists Society, Champaign, Ill. (1993)). The TLC chromatograms of material eluted from a mini-column, Bond Elut®, showed only one spot of NPC, which was well separated from the polar materials found in the untreated oil sample.

The TPC levels of the soybean oils with different IVs under two treatments (fresh vs instrument-tested) are shown in FIG. 6A. The levels in the fresh oils were not different among different unsaturation levels. The TPC in the instrument-tested oils were higher (P<0.05) than the fresh untested ones. This finding agreed with that of Sáchez-Muniz, who reported that the TPC in frying oil increased as the time of the oil used for frying increased. The most saturated soybean oil (IV=70) tested by the instrument 20 had the lowest TPC of all the instrument-tested oils. The TPC in both the instrument-tested oils with IVs of 94 and 110 were higher (P<0.05) than the other tested oils but were not different from each other. These results agreed with Dobarganes et al, "Thermal Stability and Frying Performance of Genetically Modified Sunflower Seed (*Helianthus annuus* L.) Oils," *J. Agric. Food Chem.*, 41:678–681 (1993) ("Dobarganes"), which is hereby incorporated by reference, who reported that the average TPC level in high oleic sunflower oil used for frying for 5 hr (15.5%) was less than that in regular sunflower oil (24.2%). Increase of unsaturation level of an oil increased the production of TPC in the oil during frying.

However, the TPC level in the unhydrogenated soybean oil (IV=132) was less than that of the oil with an IV of 94 and the oil with an IV of 110 (FIG. 6-(*a*)). This observation was not consistent with the previously stated observation of Dobarganes. The fraction of the TPC produced by the unhydrogenated soybean oil may have been more volatile than that produced by the oils with IVs of 94 and 110, thus the TPC that remained in the unhydrogenated soybean oil was less than which remained in the other two oils.

Dielectric Constant

The analyses of variance for the effects of replication and IV on the dielectric constant (FOS) of soybean oils tested by the instrument 20 are shown in Appendix B-6. The dielectric constants of soybean oils were different (P<0.05) among oils with different IVs.

The mean FOS readings of tested soybean oils with different IV levels are illustrated in FIG. 6B. The distribution pattern of FOS readings among different IV levels was similar to that of TPC of the same oils with the exception that the FOS of the oil with IV of 94 was less than that in the unhydrogenated soybean oil (IV=132). The most saturated oil (IV=70) had the lowest FOS reading of all oils while the oil with an IV of 110 had the highest FOS reading. The distribution pattern of the FOS readings among different IVs of the soybean oils agreed with that of Fritsch et al., "Changes in Dielectric Constant as a Measure of Frying Oil Deterioration," *J. Am. Oil Chem. Soc.*, 56:746–750 (1979), which is hereby incorporated by reference. The authors noted that hydrogenation of soybean oil reduced the production of the electrically conductive materials in the oil during frying.

The FOS reading of the unhydrogenated soybean oil was between those of the oil with an IV of 110 and the oil with an IV of 94. As mentioned in the previous section, the decomposition compounds produced by the unhydrogenated soybean oil during the instrument test may be volatile and escape from the oil so that there is less electrically conductive material contributing to conductivity.

Free Fatty Acid

The analyses of variance for the effect of IV, treatment, replication, and the interactions of IV and treatment on the free fatty acid (FFA) content in the instrument-tested oils are shown Appendix B-7. The mean free fatty acid levels of soybean oils were different (P<0.05) among the IVs and the interactions of IV X treatment.

Figure 7B:
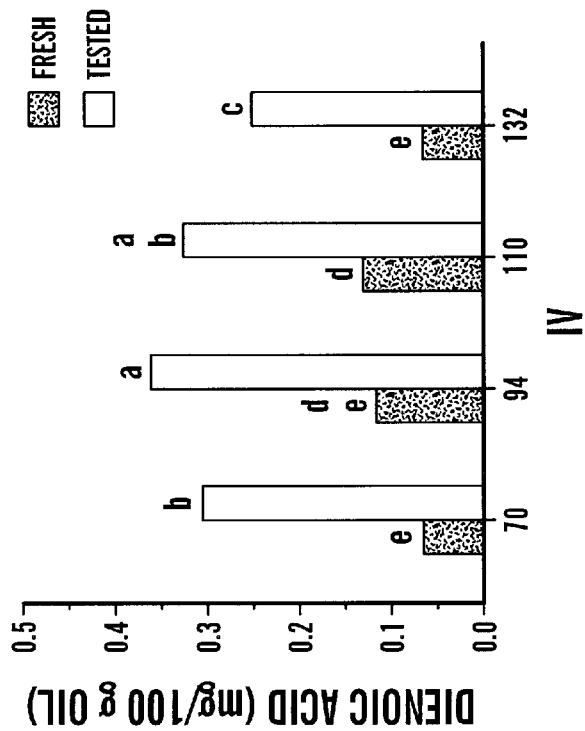
FIGS. 7A–B are a least-squares mean free fatty acid contents and dienoic acid contents, respectively, of soybean oils with different unsaturation levels (IV) under two treatments (fresh versus instrument-tested); bars with unlike letters are different (P<0.05).
Figure 7A:
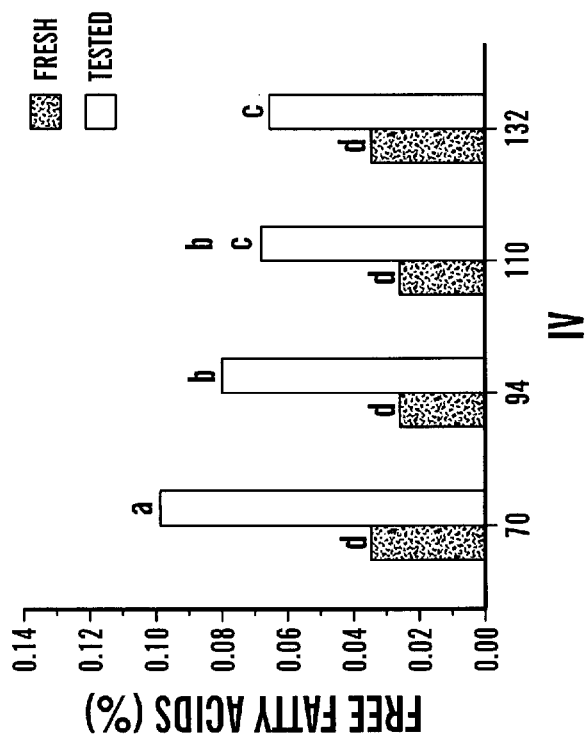

The means FFA contents of soybean oils with different IVs under two treatments (fresh vs instrument-tested) are shown in FIG. 7A. The mean FFA levels in the fresh soybean oils were not different among oils with different IVs. All mean FFA in the fresh oils were less than 0.05%; this indicated that the quality of oil samples used in this study was good (Weiss). The instrument-tested oils had higher FFA than the fresh oils; the instrument test increased the amounts of FFA in the oil. This observation agrees with that of Stevenson, who reported that the FFA in frying oil increased steadily over the frying time.

The moisturized air bubbled into the heated oil during the instrument test increased the oxidation and hydrolysis reaction rates in the oil, and thus increased its FFA level. In contract to Lin's observation that the FFA in both high oleic sunflower and cottonseed oils after the oils were heated at 160° C. for 3 hr were not different from those in the unheated oils, the FFA in all IV levels of the soybean oils increased after 200 min of the instrument test (P<0.05). The difference in the experimental conditions between the current study and Lin study was that the instrument 20 bubbled the heated oils with moisturized air. The bubbling air increased the contact between the oil and oxygen and promoted the degradation of the oil, and the moisture in air increased the hydrolysis reaction in the oil. Therefore, the FFA in the oil increased during the instrument test.

The soybean oils with higher levels of unsaturation yielded less FFA than oils with lower levels of unsaturation after the instrument test (FIG. 7A). The most saturated oil (IV=70) yielded the highest amounts of FFA of all soybean oils. The unhydrogenated soybean oil (IV=132) had the lowest (P<0.05) level of FFA of all oils. Hydrolytic reactions in the soybean oils with the two lowest levels of unsaturation may have contributed to the higher levels of more saturated, less volatile FFA than in those with higher unsaturation levels. Melton noted that accumulation of FFA in frying oils was dependent upon their volatility.

Dienoic Acid

The analyses of variance for the effects of IV, treatment, and the interaction of IV with treatment on the levels of dienoic acid in the fresh and instrument-tested oils are shown in Appendix B-8. The mean dienoic acid levels in oils were different (P<0.05) among the IVs and the treatments.

Lowest levels of dienoic acids were found in the fresh oils with IVs of 70 and 94 and the fresh, most unsaturated oil (IV=132) (FIG. 7B), with higher levels in the oil with an IV of 110. Hydrogenation of soybean oil also forms conjugated dienes in polyunsaturated oil (Weiss), but an oil can be hydrogenated to the point where polyunsaturated fatty acids (conjugated or nonconjugated) are present in low levels such as in the fresh oil with an IV of 70. In contrast, the dienoic acid levels in fresh oil with an IV of 132 are a result of processing (refining, bleaching, and deodorizing) a highly polyunsaturated oil. Higher levels of dienoic acids in the fresh oils with an IV of 110 are most likely due to hydrogenation (Weiss).

The mean dienoic acid levels of soybean oils with different IVs under two treatment (fresh vs instrument-tested) are also shown in FIG. 7-(b). Dienoic acids in each oil increased after the instrument test. The mean dienoic acid level of the oils after the instrument test (0.31 mg/100 g oil) was higher (P<0.05) than that before the test (0.10 mg/100 g oil). The increase of the dienoic acids in oils by the instrument test was caused by thermal oxidation during the test and agreed with Eskin et al., "Stability of Low Linolenic Acid Canola Oil to Frying Temperature," *J. Am. Oil Chem. Soc.*, 66:1081–1084 (1989), which is hereby incorporated by reference, who reported that the dienoic acids in both high and low linolenic acid canola oils increased (P<0.05) as the oils were heated to 185° C.

Levels of conjugated dienoic acid in the tested oils mirror to a large extent the patterns of levels in the fresh oils (FIG. 7B). The main exception to this observation is that the most unsaturated oil (IV=132) had the smallest increase in conjugated dienoic acid levels of all oils. The reason for this may have been that the dienoic acids in the oil with an IV of 132 may have degraded to volatile products at a more rapid rate than in the other oils. This oil (IV=132) did produce, by far, the largest level of VFA during the instrument test (Table 9).

Tocopherols

The analyses of variance for the effects of unsaturation level (IV), treatment, replication, and the interactions of IV and treatment on the concentrations of tocopherols, and the destruction percentages of tocopherols in the instrument-tested oil are shown in Appendix B-9. The mean concentrations of any individual tocopherol in the oils were different (P<0.05) among the IVs, treatment, and the different IV values within treatment. Total levels of tocopherols were also different (P<0.05) by IV, treatment, and their interaction. Percentage destruction of tocopherols was measured by the percentage of the reduction of the total tocopherols in the oil during the instrument test. The destruction percentages of total tocopherols were different (P<0.05) among the IVs of the oils.

The mean concentrations of tocopherols in the soybean oils before and after the instrument test and their mean destruction levels are shown in Table 10. In general, the mean concentrations of tocopherols in the oils decreased after they were tested by the instrument 20. In other words, thermal oxidation reduced the tocopherol content in the oils. The finding is consistent with that of Yoshida et al., "Influence of Fatty Acids on the Tocopherol Stability in Vegetable Oils During Microwave Heating," *J. Am. Oil Chem. Soc.,* 69:119–125 (1992), which is hereby incorporated by reference, who reported that the tocopherols in oils decreased over time as the oils were exposed to air during microwave heating.

The fresh soybean oils with IVs of 94 and 132 had the highest levels of tocopherols while the fresh oil with an IV of 110 had the lowest level. Differences in tocopherol concentrations among oils with different IVs for the individual and total tocopherols, most likely were due to the degree of processing which the oils received. All oils were refined, bleached and deodorized, while those with IVs less than 132 were partially hydrogenated, and the soybean oil with an IV of 110 also was fractionally crystallized to remove saturated triacyl glycerols. With each step of processing, the levels of tocopherols in oils have been reported to decrease (Weiss); conditions used in deodorization, in particular, can be adjusted to remove additional tocopherols from oils/fats (Weiss). These differences in processing most likely are responsible for the difference in levels of tocopherols present in the fresh oils.

In the actual weight loss of total tocopherols, the more unsaturated soybean oils (IVs of 110 and 132) lost less (45 and 30 mg/100 g oil, respectively) than the more saturated oils; the more saturated oils with IVs of 70 and 94, respectively, lost 63 and 77 mg tocopherols/100 g oil (Table 10). These observations contradict the expected results that the more unsaturated oils, which are more susceptible to oxidation, should lose a greater quantity of tocopherols. Besides being destroyed directly by oxidation, tocopherols also are destroyed by oxidizing fatty acids and peroxides (Weiss). Other factors, which also influence the rate of oxidation of oils and antioxidants, include the exposure to air, light and heat; presence of pro-oxidant metals and metal chelators, and the initial levels of tocopherols (Weiss). The oils were exposed to the same levels of heat and air during the instrument testing; however, the levels of proxidant metals and metal chelators in the different soybean oils are unknown. Also, perhaps the highly unsaturated fatty acid, linolenic acid, present in higher levels in the IV 132 soybean oil than in the other oils, competed with the tocopherols during oxidation, resulting in a lower amount of tocopherols destroyed than in the more saturated oils (Table 10).

If the effectiveness of an antioxidant can be measured by its destruction, then the tocopherol isomers in order of decreasing antioxidant effectiveness but increasing oxidative stability during the instrument test were $\gamma$, $\alpha$, and $\Delta$. The average destruction for $\gamma$-, $\alpha$-, and $\Delta$-tocopherols were 90, 70, and 62%, respectively. Jung I, reported that the oxidative stability of tocopherols in oil was $\alpha$-<$\gamma$-<$\Delta$-tocopherol. The different experimental conditions used in the instant application versus that of Jung I may have caused the difference in the order of oxidative stability of tocopherols.

TABLE 10

Least-squares mean concentrations[a,b] of tocopherols in soybean oils with different iodine values (IVs) before and after the instrument test and level of tocopherol destruction during the test

| Degree of unsaturation (IV) | Tocopherol (mg/100 g oil) | | | | | | | | Destruction of total tocopherols (%) |
|---|---|---|---|---|---|---|---|---|---|
| | $\alpha$ | | $\gamma$ | | $\Delta$ | | Total | | |
| | Fresh | Tested | Fresh | Tested | Fresh | Tested | Fresh | Tested | |
| 70 | 5.48 b | 0.37 f | 42.17 b | 0.80 e | 15.27 c | 4.28 e | 62.92 b | 5.44 e | 91.33 a |
| 94 | 6.40 a | 2.88 c | 47.88 a | 1.29 e | 18.61 b | 4.69 e | 72.90 a | 8.86 d | 87.81 a |
| 110 | 5.10 b | 1.72 e | 19.22 c | 1.05 e | 7.73 d | 2.59 f | 32.04 c | 5.36 e | 83.19 b |
| 132 | 6.55 a | 2.32 d | 47.51 a | 15.15 d | 21.96 a | 14.63 c | 76.02 a | 32.10 c | 57.63 c |

[a]$N = 3$.
[b]For concentration of any one tocopherol or total destruction, means followed by unlike letters are different ($P < 0.05$).

Fatty Acid Composition

The analyses of variance for the effects of IV, treatment, replication, and the interactions of IV and treatment on the fatty acid compositions of soybean oils tested by the instrument 20 are shown in Appendix B-10. Five fatty acids, C16:0, C18:0, C18:1, C18:2, and C18:3, were found in the soybean oils. Most of the fatty acid levels in soybean oils were different ($P<0.05$) between the treatments (fresh vs instrument-tested) and among the IVs except for the mean concentration of C18:1, which was not different between the treatments. The mean concentrations of C18:0 and C18:1 in oils were affected ($P<0.05$) also by the interaction of IV and treatment.

The means concentrations of fatty acids in soybean oils with different IVs under two different treatments (fresh vs tested) are shown in Table 11. The concentrations of both C18:2 and C18:3 decreased as the IV of the oil decreased while the concentration of C18:0 and C18:1 increased with decreasing IV. Hydrogenation of soybean oils reduced the concentrations of C18:3 and C18:2 and increased the amounts of C18:0 and C18:1 in the oils. These results agreed with the results of Weiss, who noted that hydrogenation decreased levels of polyunsaturated acids in oils.

In general, the 200-min instrument test decreased the amounts of C18:2 in most of the oils but increased the relative concentrations of C16:0, C18:0, and C18:1. The C16:0 concentration increased ($P<0.05$) in oils with IV of 70 and 132 after the instrument test. The C18:0 level in the instrument-tested oils with an IV of 110 was higher ($P<0.05$) than in its fresh state. The C18:2 level of IVs of 94 and 110 increased ($P<0.05$) following the instrument test (Table 11). These results agreed with that of McGill, "The Chemistry of Frying," *Bakers Dig.,* 54:38–42 (1980) ("McGill"), which is hereby incorporated by reference, who noted that oxidation of polyunsaturated fatty acids in the oils produced shorter chain or less unsaturated fatty acids.

TABLE 11

Least-squares mean percentages[a,b] of fatty acids in soybean oils
with different levels of unsaturation before and after the instrument test

| Degree of unsaturation (IV[c]) | Fatty acid (%) | | | | | | | | | |
|---|---|---|---|---|---|---|---|---|---|---|
| | C16:0 | | C18:0 | | C18:1 | | C18:2 | | C18:3 | |
| | Fresh | Tested | Fresh | Tested | Fresh | Tested | Fresh | Tested | Fresh | Tested |
| 70 | 10.19 b | 10.63 a | 12.04 a | 12.06 a | 77.77 a | 77.30 a | —[d] | — | — | 0 |
| 94 | 8.42 e | 8.67 e | 3.69 cd | 3.77 c | 62.30 c | 62.97 b | 25.00 d | 24.05 e | 0.59 c | 0.55 c |
| 110 | 9.27 cd | 9.46 c | 3.60 cd | 3.91 b | 40.56 e | 41.72 d | 43.92 b | 42.44 c | 2.65 b | 2.46 b |
| 132 | 8.59 e | 8.93 d | 3.50 d | 3.60 d | 19.93 f | 19.84 f | 57.40 a | 57.25 a | 10.58 a | 10.38 a |

[a]N = 3.
[b]For any one fatty acid, means followed by unlike letters are different (P < 0.10).
[c]IV = Iodine value.
[d]Not present.

3. The Effects of Additives on Instrument Measurements and Quality of the Tested Oils The Effects of Additives on Instrument Measurements The analyses of variance for the effects of additive and replication on the linear slopes and induction times of soybean oil (IV=94) measured by the instrument 20 are shown in Appendix B-11. Both linear slopes and induction time of soybean oils were different (P<0.05) among the additive treatment but not different among replications. The non-significant difference in the instrument 20 measurement (linear slope and induction time) among replications showed again that the results of the instrument 20 were reproducible.

The mean linear slopes and induction time of soybean oils, which had been treated with different additives and measured by the instrument 20, are shown in Table 12. The control oil exhibited the highest linear slope and lowest induction time among all oils, indicating that this Oil had the least oxidative stability as measured by the instrument 20. The value of either linear slope or induction time of the oil treated with 5 ppm dimethyl siloxane ("DMS") was between that of the oil treated with 100 ppm tertiary-butylatedhydroquinone ("TBHQ") and that of the oil treated with both DMS and TBHQ ("BOTH"). The linear slope or induction time of the oil containing TBHQ was not different from their respective counterpart in the oil treated with BOTH. From the instrument 20 measurement point of view, the order of oxidative stability of the oils treated with additives was control <DMS<TBHQ=BOTH.

Addition of DMS to a frying oil increases in oxidative stability during frying. Addition of 5 ppm DMS decreased (P<0.05) the linear slope of soybean oil from 0.2326 to 0.1628 µS/cm.min and increased the induction time from 49.75 to 61.32 min. DMS can increase the oxidative stability of frying oil by reducing the foaming and by forming a thin film above the frying oil surface to reduce the contact area between the oil and oxygen. DMS is usually added to frying shortening, except for doughnut production, and the maximum addition level is 10 ppm (Weiss). According to the instrument 20 design, there are at least two conditions under which the oil sample comes into contact with oxygen: the moisturized air and the headspace above the oil sample. Since the flow rate of moisturized air was held constant throughout the experiment, the reduced oxygen contact between the oil sample and the headspace by DMS contributed to its increased oxidative stability.

The Oil Stability Instrument did not detect the difference in oxidative stability between the control and the oil treated with 5 ppm DMS as did the instrument 20. The oil stability index values of the control oil and the oil treated with DMS, TBHQ, and BOTH measured by the Oil Stability Instrument were 17.55, 17.40, 38.40, and 38.90 hr, respectively. Apparently, the Oil stability index of the DMS oil (17.40 hr) was not different from that of the control (17.55 hr); the Oil Stability Instrument was not sensitive enough to detect the difference. The high air flow rate (140 mL/min) with respect to small sample size (5 g) used by the Oil Stability Instrument may account for this lack of sensitivity. Since the oil sample in Oil Stability Instrument was vigorously agitated by the bubbled air, the antifoaming effect of DMS was offset by the agitation. The instrument 20 was more sensitive than the Oil Stability Instrument in detecting the effects of DMS on the oxidative stability of frying fats/oils.

The oils containing 100 ppm TBHQ (including the oil with BOTH) had the greatest oxidative stability among all the treatments as tested by the instrument 20. The oils with TBHQ and BOTH had the lowest linear slopes and highest induction time of all oils. Addition of 100 ppm TBHQ to a frying oil increased its oxidative stability. The oil stability indexes of the TBHQ and BOTH oils (38.4 and 38.9, respectively) measured by the Oil Stability Instrument agreed with the results from the instrument 20.

Further addition of 5 ppm DMS to the frying oil containing 100 ppm TBHQ did not present any synergistic effect in the increasing oxidative stability as measured by the instrument 20. The linear slopes and induction time in the TBHQ and BOTH oils were not different from each other. The synergistic effect of adding both DMS and TBHQ to the frying oil in increasing its oxidative stability was not detected by the instrument 20.

The TBHQ evaporates and is oxidized during frying. Chemical analysis showed that TBHQ decreased from the original level of 109 ppm to 22 and 15 ppm, respectively, in the oil containing TBHQ and BOTH. Approximately 80% of the added TBHQ in the oils evaporated or was destroyed during the 200 min of the instrument test. In other words, addition of TBHQ into a frying oil may have only a short term antioxidative effect. According to Tian et al., "Antipolymerization Activity of Oat Extract in Soybean and Cottonseed Oils Under Frying Conditions," *J. Am. Oil Chem. Soc.*, 71:1087–1094 (1994) ("Tian"), which is hereby incorporated by reference, the amounts of polymers formed in the oil treated with 200 ppm TBHQ during 4 days of heating at 180° C. was less than in the control oil, but the difference in polymer formation became insignificant after 6 days of heating.

TABLE 12

Least-squares means[a,b] and coefficients of variations (CV) for linear slope and induction time of soybean oils treated with different additives and tested by the instrument 20.

| Treatment | Linear slope ($\mu$S/cm · min) | CV (%) | Induction time (min) | CV (%) |
|---|---|---|---|---|
| Control | 0.2326[a] | 5.19 | 49.75[c] | 5.95 |
| 5 ppm DMS[c] | 0.1628[b] | 6.92 | 61.32[b] | 12.92 |
| 100 ppm TBHQ[c] | 0.1322[c] | 1.94 | 72.07[a] | 1.34 |
| 100 ppm TBHQ + 5 ppm DMS | 0.1261[c] | 4.03 | 72.38[a] | 1.28 |

[a]N = 3.
[b]For any one dependent variable, means in a column followed by unlike letters are different (P < 0.05).
[c]DMS = dimethyl siloxane; TBHQ tertiary-butylatedhydroquinone.

The Effects of Additives on the Volatile Fatty Acids in the Volatile Trap Solutions

TABLE 13

Least-squares mean concentrations[a,b] of volatile fatty acids collected from soybean oils (IV = 94) treated with different additives and tested by the instrument 20 and trapped in the volatile trap solution

| | Volatile fatty acid (nM) | | | | | | |
|---|---|---|---|---|---|---|---|
| Treatment | Formic + Acetic | Propionic | Butyric | Valeric | Caproic | Unknown | Total[c] |
| Control | 0.2879 a | 0.0214 a | 0.0195 a | 0.0153 a | 0.0281 a | 0.0446 a | 0.4167 a |
| 5 ppm DMS[d] | 0.1552 d | 0.0112 c | 0.0077 b | 0.0095 c | 0.0210 b | 0.0340 ab | 0.2387 c |
| 100 ppm TBHQ[d] | 0.2270 b | 0.0151 b | 0.0096 b | 0.0127 b | 0.0213 b | 0.0224 b | 0.3079 b |
| 5 ppm DMS + 100 ppm TBHQ | 0.1691 c | 0.0113 c | 0.0092 b | 0.0121 b | 0.0194 c | 0.0214 b | 0.2424 c |

[a]N = 3.
[b]For any one dependent variable, means followed by unlike letters are different (P < 0.05).
[c]Total VFA is the summation of the VFA measured by the GC method.
[d]DMS = dimethyl siloxane; TBHQ = tertiary-butylatedhydroquinone.

The analyses of variance for the effects of additive treatment and replication on the concentrations of VFA collected in the trap solution during the instrument test are shown in Appendix B-12. As mentioned previously, seven VFA and one unknown peak were found in the DW in this study. The VFA in the volatile trap solution were different (P<0.05) among the additive treatments. Most of the VFA in the trap solution were different (P<0.05) among the replications except for the unknown, butyric acid, and valeric acid. The significant difference (P<0.05) found in VFA in the trap among replications indicated that the production of VFA by the oils during the instrument test was not consistent from time to time. Therefore, either production of VFA during the instrument test, VFA measurement, or both, needs greater control to reduce variation among replications.

The mean concentrations of VFA trapped in the trap solution from the oils treated with different additives during the instrument test are listed in Table 13. Formic and acetic acids were the major components of the total VFA. The control oil generated a higher level (P<0.05) of total VFA than did oil containing antioxidant, defoaming agent, or both. Addition of 5 ppm DMS and/or 100 ppm TBHQ to the frying oils reduced the production of VFA in the oil during frying.

Both DMS and TBHQ increased the oxidative stability of the oil as measured by the reduced production of the VFA in the oil during the instrument test. The oil containing DMS generated the smallest amounts of formic and acetic, propionic, and valeric acids and total VFA under the instrument test conditions (Table 13). The oil treated with TBHQ produced smaller amounts of VFA and total VFA during the instrument test. TBHQ also increased the oxidative stability of the oil by reducing the production of VFA by the oil during drying. However, DMS is more effective in increasing oxidative stability of a frying oil than TBHQ. The levels of formic and acetic, propionic, and valeric acids and the total VFA in the water trap attached to the oil treated with DMS were lower (P<0.05) than in that attached to the oil containing TBHQ.

The total VFA level collected from the oil that contained BOTH was not different from that collected from the oil containing DMS during the instrument test. However, concentrations of some of the individual VFA, formic and acetic acid group and valeric acid, were greater in the volatile trap from oil treated with BOTH compared with that from the oil containing DMS only (Table 13). The production of VFA in oil during the instrument test was not synergistically reduced by the combined use of DMS and TBHQ.

Quality of the Oils Following the Instrument Test
Total Polar Components

The analyses of variance for the effects of replication and additive treatment on the TPC of the oils tested by the instrument 20 are shown in Appendix B-13. The levels of TPC in the oils were different (P<0.05) among the additive treatments but were not different among the replications.

Figure 8B:
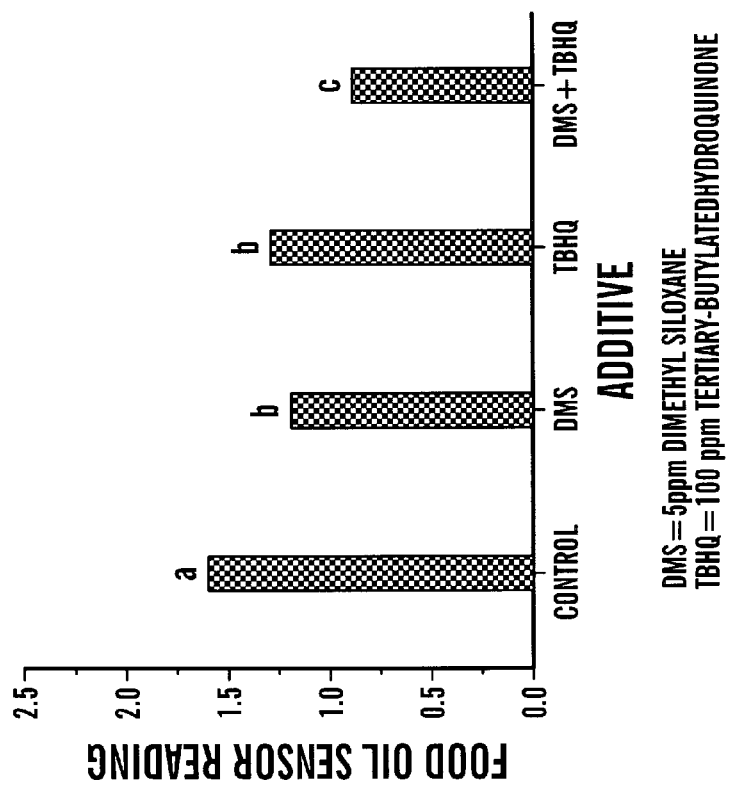
FIGS. 8A–B are a least-squares means for total polar component levels and dielectric constants (Food Oil Sensor reading), respectively, of fresh soybean oil (IV=94) and soybean oil (IV=94) treated with different additives and tested by the instrument for 200 min; bars with unlike letters are different (P<0.05).
Figure 8A:
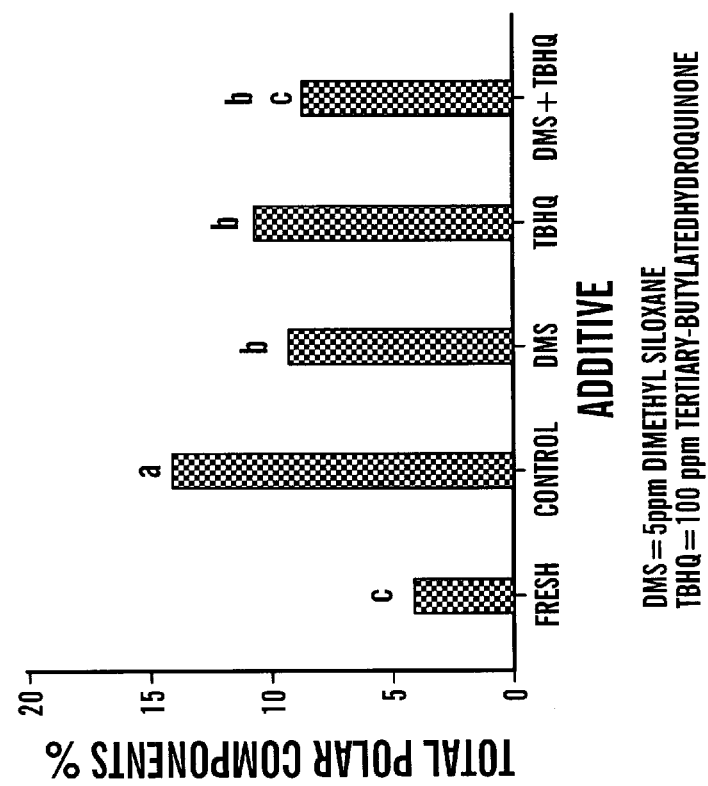

The mean TPC concentrations of the soybean oil (IV=94) treated with different additives and tested by the instrument 20 are shown in FIG. 8A. The TPC in the instrument-tested oils were higher in amounts than those in the fresh oil; the levels in TPC in oils increased after the oils were subjected to the instrument test conditions for 200 min. The control oil had the highest amounts of TPC of all tested oils. The TPC levels in the additive treated oils were not different from each other. Addition of DMS, TBHQ, or BOTH to oils reduced production of polar components during frying.

The TPC level in the oil with BOTH after the instrument test was not different from that in the oils with DMS or TBHQ alone. Addition of 5 ppm DMS to the oil containing 100 ppm of TBHQ did not further reduce the production of polar materials in the oil during frying compared to use of either DMS or TBHQ alone.

Dielectric Constant

The analyses of variance for the effects of replication and additive treatment on the dielectric constant (FOS) of the oils after the instrument test are shown in Appendix B-14. The FOS of the oils were different (P<0.05) among the additive treatments but not different among the replications.

The mean FOS levels of the oils treated with different additives are shown in FIG. 8B. The distribution pattern of FOS of the oils treated with different additives was similar to that of TPC of the same oils except that the TPC level in the oil treated with BOTH was smaller (P<0.05) than in the oil treated with either DMS or TBHQ alone. The similar distribution pattern of the FOS in the oils to that of TPC levels indicated that the total polar materials in oils probably contributed to the electrical conductivity of the oils. The instrument-tested control oil had a higher (P<0.05) FOS than other tested oils. The FOS of the oil with DMS was not different from that of the oil containing TBHQ. The oil with BOTH had the smallest FOS of all the oils. Addition of 5 ppm DMS or 100 ppm TBHQ to a frying oil increased its oxidative stability. The combined use of DMS and TBHQ reduced (P<0.05) synergistically the FOS of the instrument-tested oil.

Free Fatty Acids

The analyses of variance for the effects of additive and replication on the FFA content in the oils tested by the instrument 20 are shown in Appendix B-15. The FFA in oils treated with different additives were different (P<0.05) among the additive treatments and replications. The production of FFA in the oil during the instrument test was not consistent from test to test.

Figure 9B:
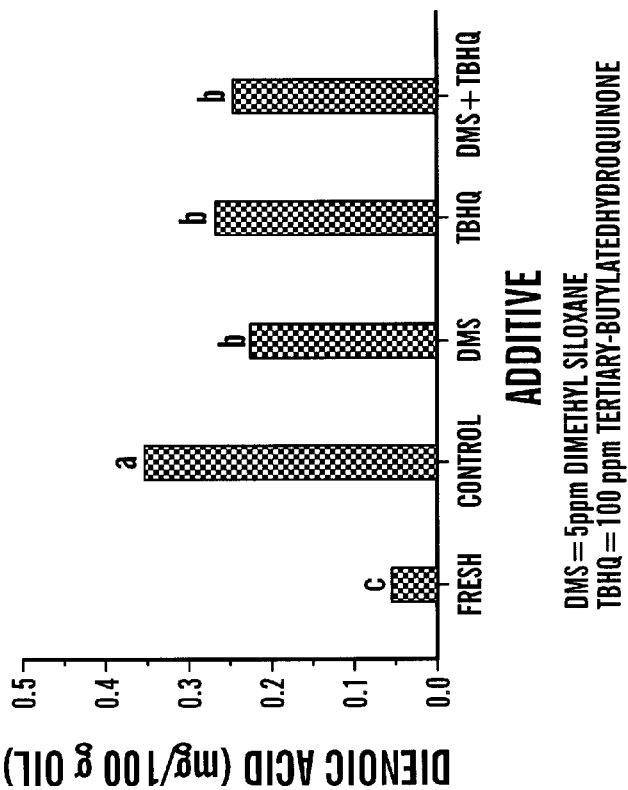
FIGS. 9A–B are a least-squares means for free fatty acid contents and dienoic acid contents, respectively, in fresh soybean oil (IV=94) and soybean oil (IV=94) treated with different additives and tested by the instrument for 200 min; bars with unlike letters are different (P<0.05).
Figure 9A:
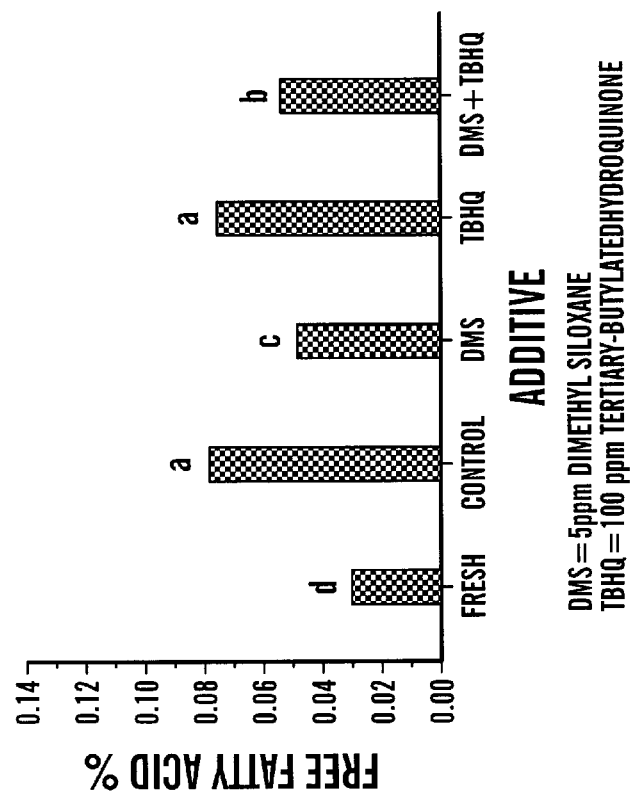

The mean FFA contents in the soybean oils treated with different additives are shown in FIG. 9A. The FFA content in the oils increased after the oils were subjected to the instrument test conditions for 200 min. The fresh untested oil had the lowest FFA content of all the oils but the level of FFA increased after the oils were tested by the instrument 20. As mentioned previously, moisture most likely caused hydrolysis in the oil sample during the instrument test. The FFA contents in the control oil and the oil containing TBHQ were higher than in the other oils. The oil with DMS had the lowest level of FFA of all the instrument-tested oils. Addition of TBHQ to DMS-containing oil may have interfered with the effectiveness of DMS in reducing production of FFA during the instrument test; the FFA level of the oil containing BOTH was higher (P<0.05) than that in DMS treated oil. The greater effectiveness of DMS than TBHQ in reducing production of VFA (Table 13) and FFA levels indicated that a surface active agent was more effective than an antioxidant in reducing thermal oxidation and possibly hydrolysis of oil at high temperatures.

Dienoic Acids

The analyses of variance for the effects additive treatment and replication on the levels of dienoic acids in the instrument-tested oils are shown in Appendix B-16. The dienoic acid contents in the oils were different (P<0.05) among the additive treatments but not different among replications.

The mean dienoic acid contents of the fresh untested oil and treated with different additives and then tested by the instrument 20 are plotted in FIG. 9B. The dienoic acid content in the fresh untested oil was lower (P<0.05) than that in the tested oils. The dienoic acids in the oil increased after the oil was subjected to 200 min of the instrument test conditions. The control oil had the highest dienoic acid content of all the oils. The oils treated with DMS, TBHQ, or BOTH developed fewer dienoic acids than the control oil. According to the results of dienoic acid analysis, addition of DMS or TBHQ to frying oil increased the oil's oxidative stability. The dienoic acid level in the oil with BOTH was not different from that in the oil with DMS or TBHQ. The combination of DMS and TBHQ in a frying oil did not further reduce the oxidative reactions in the oil during frying.

Tocopherols

The analysis of variance for the effects of additive treatment and replication on the concentrations of tocopherols, total tocopherol contents, and tocopherol destruction percentage in the instrument-tested oils are shown in Appendix B-17. As mentioned previously, α-, γ-, and Δ-tocopherols were identified in the study. Every individual tocopherol level in the tested oil was different (P<0.05) from each other among the additive treatments. Replication was different (P<0.05) for α-tocopherol level, but not for γ- or Δ-tocopherol levels, total level of tocopherols, or tocopherol destruction percentage (P>0.05). Degradation of α-tocopherol in the oils during the instrument test was not consistent among replications in this study.

The mean concentrations of tocopherols in the additive-treated soybean oils (IV=94) before and after the instrument test are shown in Table 14. Each tocopherol concentration in each oil decreased after the oil was tested by the instrument 20. Reduction of tocopherol concentrations in the oil may be due to reaction of tocopherols with pro-oxidative materials in the oil during frying and their subsequent degradation.

The α-tocopherol in the control oil after the instrument test was higher (P<0.05) than that in oils treated with additives; this was not expected. The reason for the relatively higher amounts of the α-tocopherol surviving in the control oil following the instrument test is not known. The control oil had the lowest amount of γ, Δ-, and total tocopherols of all tested oils. The destruction of tocopherols in the control oil following the instrument test (87.7%) also was higher (P<0.05) than that in the oils treated with additives. More destruction of tocopherols occurred in the control oil during the instrument test than in other oils due to a lack of protection imparted by the DMS and/or TBHQ. The antifoaming function of DMS and the quenching of pro-oxidant radicals by TBHQ reduced the destruction of tocopherols in the oil during the instrument test.

DMS was more protective than TBHQ against the destruction of the tocopherols in the oil during frying. A comparison of each tocopherol and the total tocopherol contents of the oil with DMS or TBHQ showed that tocopherols survived better in the oil with DMS than in the oil with TBHQ during the instrument test. The tocopherol destruction percentage (79.0%) of the oil with DMS was less (P<0.05) than that (84.7%) of the oil with TBHQ (Table 14); DMS provided more antioxidative protection to the oil than TBHQ during the instrument test.

The synergistic effect of the combination of both DMS and TBHQ in a frying oil on increasing oxidative stability of the oil was shown by the reduced degree of the tocopherol destruction in the oil with BOTH (71.2%) compared with that in other oils (Table 14). Therefore, the combination of DMS and TBHQ in the oil provided a synergistic protection against oxidation of the oil during instrument testing.

TABLE 14

Least-squares mean concentrations[a,b] of tocopherols in soybean oil (IV = 94) before instrument test and in soybean oil (IV = 94) treated with different additives and tested by the instrument 20 method for 200 min

| Treatment | Tocopherol (mg/100 g oil) | | | | Destruction of total toco-pherols (%) |
| --- | --- | --- | --- | --- | --- |
| | α | γ | Δ | Total | |
| Before test | 6.46[a] | 47.52[a] | 18.37[a] | 72.35[a] | |
| Control | 2.88[b] | 1.29[e] | 4.69[e] | 8.86[e] | 87.82[a] |

TABLE 14-continued

Least-squares mean concentrations[a,b] of tocopherols in soybean oil (IV = 94) before instrument test and in soybean oil (IV = 94) treated with different additives and tested by the instrument 20 method for 200 min

| Treatment | Tocopherol (mg/100 g oil) | | | | Destruction of total toco-pherols (%) |
|---|---|---|---|---|---|
| | α | γ | Δ | Total | |
| 6 ppm DMS[c] | 1.21[c] | 5.84[c] | 8.08[c] | 15.13[c] | 78.99[c] |
| 100 ppm TBHQ[c] | 1.40[c] | 2.89[d] | 6.74[d] | 11.03[d] | 84.74[b] |
| 5 ppm DMS + 100 ppm TBHQ | 1.42[c] | 9.60[b] | 10.72[b] | 21.74[b] | 71.20[d] |

[a]N = 3.
[b]For any one tocopherol or destruction of total tocopherols, means followed by unlike letters are different (P < 0.05).
[c]DMS dimethyl siloxane; TBHQ tertiary-butylatedhydroquinone.

Fatty Acid Composition

The analysis of variance for the effects of additive and replication on the concentrations of fatty acids in soybean oil (IV=94) tested by the instrument 20 are shown in Appendix B-18. In addition to the five fatty acids (C16:0, C18:0, C18:1, C18:2, and C18:3) identified in the soybean oil (IV=94) in this study, the ratio of C18:2 to C16:0 (RATIO) was also used to compare the impact of the additives on oxidative stability of the oils. The concentration of each fatty acid and the RATIO in the oils were different (P<0.05) among the additive treatments.

The mean concentrations of fatty acids in fresh soybean oils (IV=94) and in the same oil treated with different additives and tested by the instrument 20 are shown in Table 15. In general, the concentration of C18:2 in the soybean oils decreased, and the concentration of C16:0 increased in all oils after 200 min of the instrument test. This observation agrees with that of McGill, who reported that the breakdown of double bonds in polyunsaturated fatty acids such as C18:2 reduced its concentrations during thermal oxidation. Reduction in relative concentration of polyunsaturated C18:2 can increase the levels (%) of more stable fatty acids such as C16:0. The concentration of C16:0 in the oil with TBHQ and BOTH were higher (P<0.05) than in the control and other oils. This degree of increase of C16:0 in the oil with TBHQ and BOTH may be the result of the breakdown of C18:0, the oil containing TBHQ or BOTH had lower levels of C18:0 than the fresh and control oils or oil with DMS (Table 15).

An increase in the C18:1 level and the largest decrease in C18:2 level occurred in the control oil during testing. The control oil had the least oxidative stability of all the oils. Oils treated with either DMS or BOTH had a smaller degree of increase in C18:1 and decrease in C18:2 than the control oil during the instrument test. RATIO measures the relative oxidative stability of the oils; a higher RATIO represents greater oxidative stability of the oil. According to Tian, RATIO correlated with the iodine value and dielectric constant and provided an indication of oil deterioration. The fresh oil had the highest RATIO of all the oils, but the RATIO decreased in the tested oils. Of all tested oils, the oil with DMS had the highest RATIO; addition of DMS to the oil increased its oxidative stability. The oil containing TBHQ and BOTH had similar RATIOs to that of the control oil, perhaps indicating that RATIO is not as good of an indicator of oil deterioration as reported.

Compared with the fresh oil, the control oil had the only increase (P<0.05) in C18:1 of all instrument-tested oils. The control oil also had the largest decrease in C18:2 level and one of the smaller increases in C16:0 levels among the tested oils. McGill also reported that relative concentrations of C18:1 increased with decreasing level of C18:2 in frying oils. These fatty acid profiles indicate while DMS protected oil polyunsaturated acids fatty acids from thermal oxidation, TBHQ was not as effective.

TABLE 15

Least-squares mean percentage[a,b] of fatty acids in fresh soybean oil (IV = 94) and the same oil treated with different additives and tested with the instrument 20 method for 200 min

| Variable | Treatment | | | | | | | | | |
|---|---|---|---|---|---|---|---|---|---|---|
| | Fresh | | Control | | 5 ppm DMS[c] | | 100 ppm TBHQ[c] | | DMS + TBMQ | |
| C16:0 (%) | 8.39 | c | 8.67 | b | 8.69 | b | 9.01 | a | 8.97 | a |
| C18:0 (%) | 3.70 | a | 3.77 | a | 3.75 | a | 3.58 | b | 3.62 | b |
| C18:1 (%) | 61.64 | b | 62.97 | a | 61.58 | b | 62.41 | ab | 62.12 | b |
| C18:2 (%) | 25.64 | a | 24.05 | c | 25.29 | a | 24.31 | bc | 24.59 | b |
| C18:3 (%) | 0.62 | | 0.55 | | 0.69 | | 0.69 | | 0.70 | |
| RATIO[d] | 3.056 | a | 2.774 | c | 2.910 | b | 2.699 | c | 2.741 | c |

[a]N = 3.
[b]For any one variable, means in a row followed by unlike letters are different (P < 0.05).
[c]DMS = dimethyl siloxane; TBHQ = tertiary-butylatedhydroquinone.
[d]Ratio = concentration of C18:2/concentration of C16:0.

4. The Accuracy of the Instrument

The ability of the instrument 20 measurements, linear slope and induction time, to measure oil oxidative stability is expressed by the correlation relationship between the oil stability index and the linear slope or induction time of the soybean oils analyzed in this study, except for the oil containing DMS. As mentioned previously, the oil stability index of the oil with DMS analyzed by the Oil Stability Instrument was not different from the control, but the instrument 20 method detected a significant difference (P<0.05) in the oxidative stability between the two oils. Therefore, the data of the oil with DMS was removed from the correlation analysis between oil stability index values and instrument 20 results.

Figure 10:
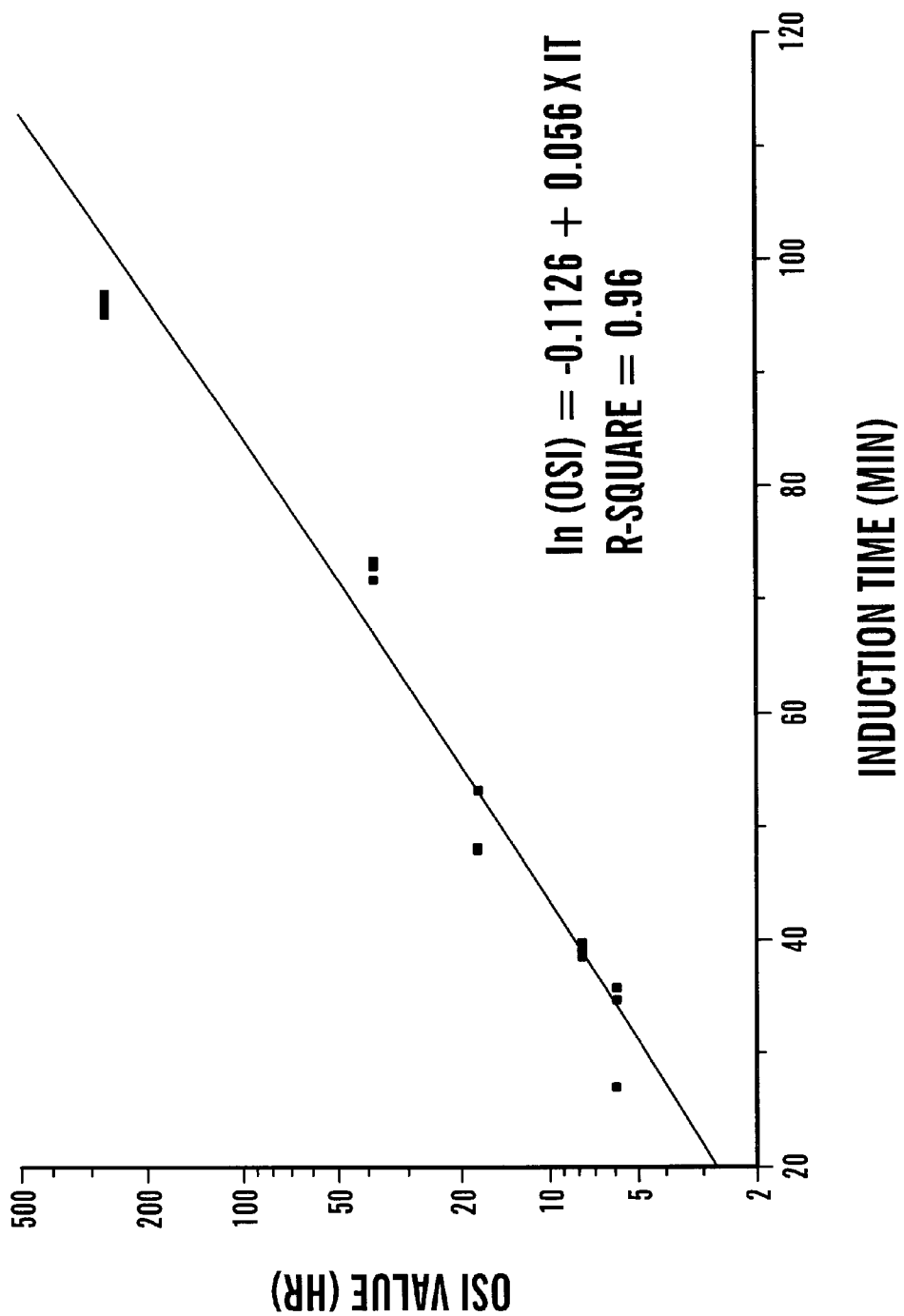
FIG. 10 is the regression between the Oil Stability Index (OSI) at 110° C. and induction time of the soybean oils (IVs=70, 94, 110, and 132) and soybean oil (IV=94) treated with tertiary-butylatedhydroquinone (TBHQ) or both dimethyl siloxane and TBHQ (n=18).

The relationship between the oil stability index values and induction time is exponential and can be expressed by the regression equation shown in FIG. 10; the statistical analysis for this regression is shown in Appendix C-1. The R-square (0.96) of the regression line indicated a high linear correlation between the oil stability index values at 110° C. and the induction time of the instrument 20 measurement. The estimate of the oil oxidative stability determined by induction time of the instrument 20 is very close to that estimated by the Oil Stability Instrument.

Figure 11:
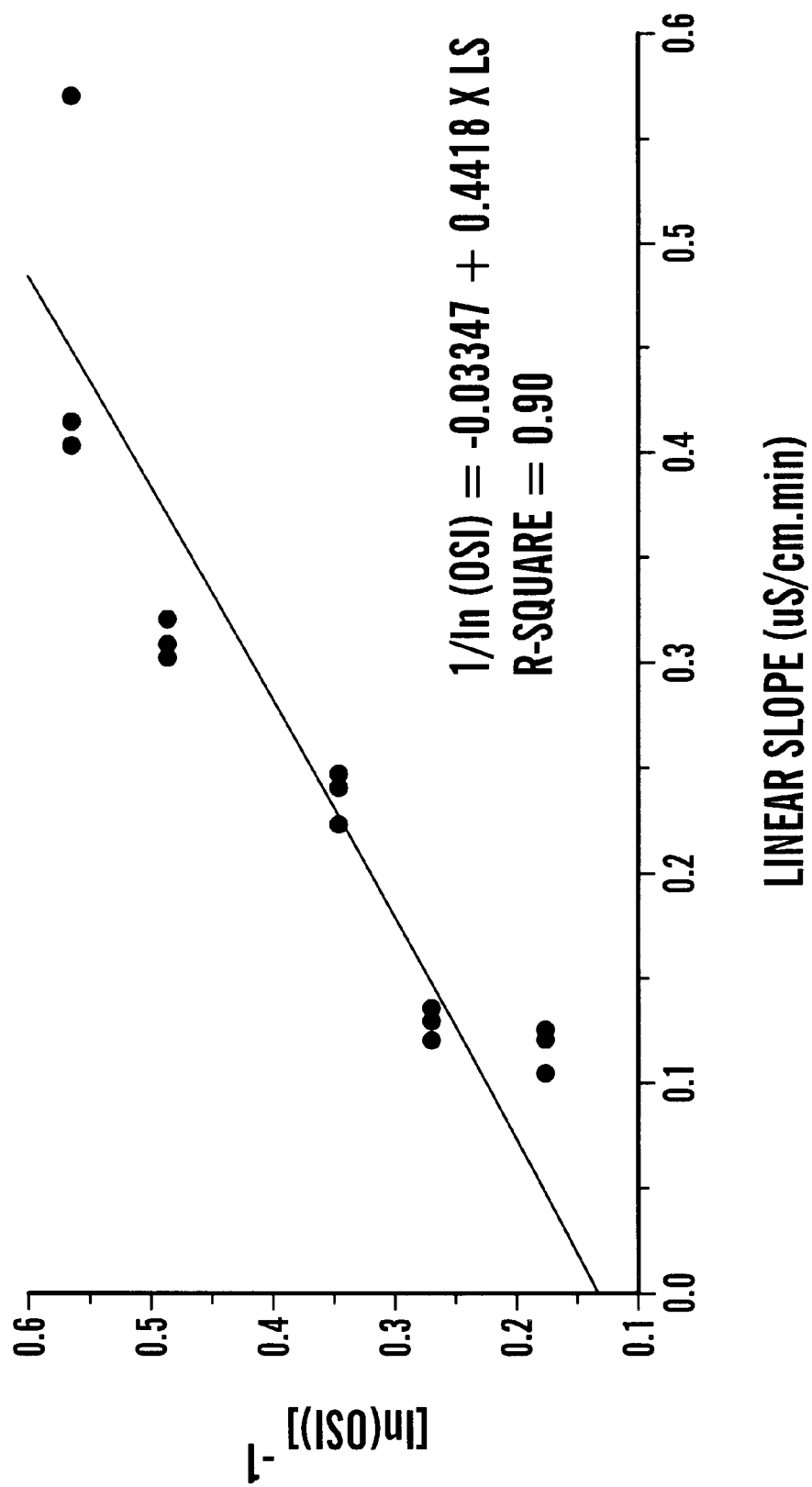
FIG. 11 is the regression between the Oil Stability Index (OSI) at 110° C. and linear slope of the soybean oils (IVs=70, 94, 110, and 132) and soybean oil (IV=94) treated with tertiary-butylatedhydroquinone (TBHQ) or both dimethyl siloxane and TBHQ (n=18).

The relationship between the reciprocal of the oil stability index and linear slope is linear and can be expressed by the regression equation shown in FIG. 11; the statistical analysis for this regression is shown in Appendix C-2. A high R-square (0.90) was observed for the regression line; therefore, it can be concluded that the correlation (P<0.0001) between the reciprocal of the oil stability index at 110° C. and the linear slope of the instrument 20 measurement was high. The linear slope of the instrument 20 measurement provided information that has never been reported before. The VDP production rate of an oil during the initiation stage of lipid oxidation under instrument test conditions is directly proportional to the oxidative stability of the oil.

The estimation of oxidative stability of both induction time and linear slope measured by the instrument 20 is very close to the oil stability index at 110° C. The AOM had been the most widely used method to determine the oxidative stability of a fat/oil. The oil stability index value measured by the Rancimat or the Oxidative Stability Instrument provides an alternative estimation of the AOM without the time-consuming and labor intensive work. The instrument 20 can provide two estimates, linear slope and induction time, to determine oil oxidative stability.

5. The Advantages and Improvement of the Instrument Test for Oil Stability Measurement Since the induction time of the most stable oil (IV=70) in this study and the time used to measure the linear slope of the oil were less than 96 min, the induction time of most of the fats/oils measured by the instrument test are postulated to be less than 2 hr. Therefore, the instrument 20 measurement of the fat/oil oxidative stability should be conducted within 2 hr, a time period much less than that required for measurement of oil stability index (OSI), currently the most widely used measurement for oil stability. Also, the instrument 20 measurements showed that adding DMS to an oil increased its stability when the OSI measurement failed to do so indicating the instrument 20 measurement has wider applications than the OSI measurement. OSI values of soybean oils of different levels of unsaturation and containing TBHQ also can be accurately calculated from either of the instrument 20 measurements, an added advantage since OSI is the accepted standard for oil stability in the oil industry.

Although results of the present study indicate the instrument 20 provides a fast, fairly reproducible, accurate and simple method to determine oxidative stability of fats/oils, care should be take in preparing the equipment for the instrument test. A reliable instrument 20 measurement depends on the quality of the HPLC-grade water and clean tubing. Since the instrument 20 uses a very sensitive conductivity probe, impurities in the water trap interfere with the baseline of the instrument 20 measurements. The conductivity of the HPLC water should be less than 4 $\mu$S/cm, a requirement that is usually met by HPLC grade water. Clean tubing protects the instrument 20 measurement from interferences by impurities and deposits of VDP inside the tubing; such deposits reduce the reproducibility of the instrument 20.

To increase the reliability and productivity of measuring oil stability by the instrument 20 method, many potential improvements can be made in the instrument 20. The efficiency of the oil heating devices can be improved by replacing the hot plate with an aluminum cooling/heating block with excellent temperature control. The oil sample vessels can be replaced by a U-shaped glass tube to increase the heat transfer area between oil sample and the heating block. Such a design may control oil temperature more effectively than the current design. The computer software can be improved by including a real-time graphic presentation of the instrument curve and the acid curve and a real-time reading of the linear slope value. The time efficiency of the instrument 20 can be further improved by a multi-channel design that handles many samples at one time.

Although the invention has been described in detail for the purpose of illustration, it is understood that such detail is solely for that purpose, and variations can be made therein by those skilled in the art without departing from the spirit and scope of the invention which is defined by the following claims.

APPENDIX A

The Instrument
Control and Data Acquisition Program

```
'****************************************************************
'*     UT Food Science & Technology Dept.     *
'*     Instrument                             *
'*     Automatic Device Control Program       *
'*     Created by: Hung-Wei Lin               *
'*     Date: Dec. 24, 1995                    *
'****************************************************************
'****************************************************************
'*     General Constant Set Up                *
'****************************************************************
Const BoardNum = 0
Const Direction % = DIGITALOUT
Dim ot
Dim wtins
Dim wt
Dim CON
Dim os
Dim OSi
Dim ws
Dim cs
Dim inwt
Dim tim
'****************************************************************
'*     Initiating and Operation Starter Program    *
'****************************************************************
Sub cmdstartconvert_Click ()
    ws = hsbwatertemp.Value
    os = hsboilset.Value
    cs = hsbcoolingbox.Value
    OSi = os - 20
    cmdStartConvert.Visible = 0
    cmdstartConvert.Default = 0
    cmdStopConvert.Visible = 1
    cmdStopConvert.Default = 1
    tmrConvert.Interval = 3000
    ULStat% = cbDConfigPort%(BoardNum, firstportcl, Direction%)
```

APPENDIX A-continued

The Instrument
Control and Data Acquisition Program

```
If ULStat% <> 0 Then Stop
ULStat% = cbDout%(BoardNum, firstportcl, 0)
If ULStat% <> 0 Then Stop
ULStat% = cbDConfigPort%(BoardNum, firstportch, Direction%)
If ULStat% <> 0 Then Stop
ULStat% = cbDout%(BoardNum firstportch, 0)
If ULStat% <> 0 Then Stop
Time = "00:00:00"
End Sub
'***************************************************************
'*      Operation Stopper Program        *
'***************************************************************
Sub cmdStopConvert_Click ()
   ULStat% = cbDout%(BoardNum, firstportch, 0)
   if ULStat% <> 0 Then Stop
   For n = 1 To 100000
   Next n
   ULStat% = cbDout%(BoardNum, firstportcl, 0)
   if ULStat% <> 0 Then Stop
   End
End Sub
'***************************************************************
'*      Screen Loading and Data Storing Program    *
'***************************************************************
Sub Form_Load ()
Dim FileName As String
ULStat% = cbErrHandling%(PRINTALL, DONTSTOP)
if ULStat% <> 0 Then Stop
FileName = InputBox("Enter The File Name For Current Sample?", "Data Management Center")
   On Error Resume Next
   Do
      Err = 0
      Open FileName For Output As #1
      Select Case Err
         Case 0
         MsgBox "Are you sure to proceed this test!"
         Case 52, 64
         FileName = InputBox("File name was invalid. Try Again!")
         Case 61
         MsgBox "Disk is full."
         Case 68
         FileName = InputBox("Device is not available. Try Again!")
         Case 71
         MsgBox "Drive Error -- Close the drive door"
         Case 76
         MsgBox "This Directory was not found."
         Case Else
         MsgBox "Error: Cannot Continue This Operation!!!"
         Stop
      End Select
   Loop Until Err = 0
'---------------------------------------------------------------
'-      Electronic Scale Initiation Sub-program      -
'---------------------------------------------------------------
   total = 0
   For q = 1 To 200
   ULStat% = cbAIn%(BoardNum, 4, BIP1VOLTS, wi%)
   'If ULStat% <> 0 Then Stop
   total = total + wi%
   Next q
   ave = total/200
   inwt = -966.204 + .444657 * ave
   If inwt <= 0 Then wt = 0
   lbInitial(1).Caption = Format$(inwt, "0.0")
End Sub
'***************************************************************
'*      Data Displaying Programs             *
'***************************************************************
Sub hsbcoolingbox_Change ()
Datavalue% = hsbcoolingbox.Value
txtcoolingbox.Text = Format$(Datavalue%, "0")
End Sub
Sub hsboilset_Change ()
Datavalue% = hsboilset.Value
txtoilset.Text = Format$(Datavalue%, "0")
End Sub
```

APPENDIX A-continued

The Instrument
Control and Data Acquisition Program

```
Sub hsbwatertemp_Change ()
Datavalue% = hsbwatertemp.Value
txtwaterset.Text = Format$(Datavalue%, "0")
End Sub
'****************************************************************
'*      On Screen On/Off Bottom Control      *
'****************************************************************
Sub startconvert_Click ()
  tmrConvert.Interval = 300
  cmdStartConvert.Visible = 0
  cmdStartConvert.Default = 0
  cmdStopConvert.Visible = 1
  cmdStopConvert.Default = 1
End Sub
Sub StopConvert_Click ()
  End
End Sub
Next k
cbt = total2/100 + .00125
cb = .10086091 + 25727.94369 * cbt − 767345.8295 * cbt ^ 2 + 78025595.81 * cbt ^ 3 − 9247486589# * cbt ^ 4 + 697688000000# * cbt ^ 5 − 26119200000000# *cbt ^ 6 +  394078000000000# * cbt ^ 7
lblcool(1).Caption = Format$(cb, "0.00")
'---------------------------------------------------------------
'-      Weight Change Measurement       -
'---------------------------------------------------------------
total3 = 0
For q = 1 To 200
ULStat% = cbAIn%(BoardNum, 4, BIP1VOLTS, wti%)
'If ULStat% <> 0 Then Stop
total3 = total3 + wti%
Next q
ave = total3/200
wtf = −966.204 + .444657 * ave
wt = wtf − inwt
lblwtincrease(1).Caption = Format$(wt, "0.0")
'---------------------------------------------------------------
'-      Conductivity Measurement        -
'---------------------------------------------------------------
total5 = 0
For h = 1 To 100
ULStat% = cbAIn%(BoardNum, 5, BtP5VOLTS, A5%)
v = (A5% − 2048)/2048*5
total5 = total5 + v
Next h
av = total5/100
CON = 10.7132 * ((2.8 − av)/(2.8 + av)) * ((200 + wt)/200)
If CON < 0 Then CON = 0
lblshowcon(1).Caption = Format$(CON, "0.00")
'---------------------------------------------------------------
'-      Progressing Time Recording Program     -
'---------------------------------------------------------------
If ot < os − 10 Then Time = "00:00:00"
tim = Hour(Now) * 60 + Minute(Now) + Second(Now)/60
lbltime(1).Caption = Format$(tim, "0.00")
'****************************************************************
'*      Device Control Program I: Water and Oil Temperatures *
'****************************************************************
  If ot > os And al >= ws Then
  ULStat% = cbDout%(BoardNum, firstportcl, 0)
  ElseIf ot > os And al < ws Then
  ULStat% = cbDout%(BoardNum, firstportcl, 1)
  ElseIf ot < OSi And al > ws Then
  ULStat% = cbDout%(BoardNum, firstportcl, 2)
  ElseIf ot < OSi And al <= ws Then
  ULStat% = cbDout%(BoardNum, firstportcl, 3)
  ElseIf (os >= ot And ot >= OSi) And al > ws Then
  ULStat% = cbDout%(BoardNum, firstportcl, 4)
  ElseIf (os >= ot And ot >= OSi) And al <= ws Then
  ULStat% = cbDout%(BoardNum, firstportcl, 5)
  End If
  For k = 1 To 10000
  Next k
'****************************************************************
'*      Device Control Program II: Air and Cooling Box Temp. *
'****************************************************************
If ot <= OSi And cb <= cs − .5 Then
```

APPENDIX A-continued

The Instrument
Control and Data Acquisition Program

```
    ULStat% = cbDout%(BoardNum, firstportch, 0)
  ElseIf ot <= OSi And cb > cs Then
    ULStat% = cbDout%(BoardNum, firstportch, 1)
  ElseIf ot > OSi And cb <= cs - .5 Then
    ULStat% = cbDout%(BoardNum, firstportch, 2)
  ElseIf ot > OSi And cb > cs Then
    ULStat% = cbDout%(BoardNum, firstportch, 3)
  End If
End Sub
'****************************************************************
'*      Setting Device Temperature Limits Program      *
'****************************************************************
  '--------------------------------------------------------------
  '-      Cooling Box Temperature Limits         -
  '--------------------------------------------------------------
Sub txtcoolingbox_Change ()
If Val(txtcoolingbox.Text) > 20 Then txtcoolingbox.Text = "20"
If Val(txtcoolingbox.Text) <= 0 Then txtcoolingbox.Text = "0"
hsbcoolingbox.Value = Val(txtcoolingbox.Text)
End Sub
  '--------------------------------------------------------------
  '-      Setting Oil Temperature Limits         -
  '--------------------------------------------------------------
Sub txtoilset_Change ()
If Val(txtoilset.Text) > 200 Then txtoilset.Text = "200"
If Val(txtoilset.Text) < 80 Then txtoilset.Text = "80"
hsboilset.Value = Val(txtoilset.Text)
End Sub
  '--------------------------------------------------------------
  '-      Setting Water Temperature Limits       -
  '--------------------------------------------------------------
Sub txtwaterset_Change ()
If Val(txtwaterset.Text) > 160 Then txtwaterset.Text = "160"
hsbwatertemp.Value = Val(txtwaterset.Text)
End Sub
```

APPENDIX B

ANALYSES OF VARIANCE

Appendix B-1: Analyses of variance for the effects
of OTS, WTS, and the interactions of OTS and WTS on the LSs and
ITs of the sunflower oil tested by the instrument.
General Linear Models Procedure Dependent Variable: LS

| Source | DF | Sum of Squares | Mean Square | F Value | Pr > F |
|---|---|---|---|---|---|
| Model | 10 | 0.0694999 | 0.0069500 | 3.76 | 0.0092 |
| Error | 16 | 0.0295942 | 0.0018496 | | |
| Corrected Total | 26 | 0.0990941 | | | |
| | R-Square | C.V. | Root MSE | LS Mean | |
| | 0.701353 | 16.34756 | 0.0430 | 0.2631 | |
| Source | DF | Type III SS | Mean Square | F Value | Pr > F |
| OTS | 2 | 0.0640211 | 0.0320106 | 17.31 | 0.0001 |
| WTS | 2 | 0.0026913 | 0.0013456 | 0.73 | 0.4984 |
| OTS*WTS | 4 | 0.0003747 | 0.0000937 | 0.05 | 0.9947 |
| REPLICATION | 2 | 0.0024128 | 0.0012064 | 0.65 | 0.5342 |

Dependent Variable: IT

| Source | DF | Sum of Squares | Mean Square | F Value | Pr > F |
|---|---|---|---|---|---|
| Model | 10 | 1218.0281 | 121.8028 | 3.53 | 0.0123 |
| Error | 16 | 552.5814 | 34.5363 | | |
| Corrected Total | 26 | 1770.6095 | | | |
| | R-Square | C.V. | Root MSE | IT Mean | |
| | 0.6879151 | 3.48775 | 5.8768 | 43.571 | |
| Source | DF | Type III SS | Mean Square | F Value | Pr > F |

APPENDIX B-continued

ANALYSES OF VARIANCE

| OTS | 2 | 1139.1782 | 569.5891 | 16.49 | 0.0001 |
|---|---|---|---|---|---|
| WTS | 2 | 57.4463 | 28.7231 | 0.83 | 0.4533 |
| OTS*WTS | 4 | 19.3926 | 4.8481 | 0.14 | 0.9647 |
| REPLICATION | 2 | 2.0111 | 1.0055 | 0.03 | 0.9714 |

Appendix B-2: The analyses of variance for the effect of OTS and WTS on the concentrations of volatile fatty acids in DW collected during the instrument test.
General Linear Models Procedure Dependent Variable: Formic and Acetic Acid

| Source | DF | Sum of Squares | F Value | Pr > F |
|---|---|---|---|---|
| Model | 4 | 0.00026052 | 1.95 | 0.2662 |
| Error | 4 | 0.00013331 | | |
| Corrected Total | 8 | 0.00039383 | | |
| | R-Square | C.V. | Formic and Acetic Acid Mean | |
| | 0.661513 | 4.907160 | 0.11764260 | |
| Source | DF | Type III SS | F Value | Pr > F |
| OTS | 2 | 0.00022604 | 3.39 | 0.1376 |
| WTS | 2 | 0.00003448 | 0.52 | 0.6312 |

Dependent Variable: Valeric Acid

| Source | DF | Sum of Squares | F Value | Pr > F |
|---|---|---|---|---|
| Model | 4 | 0.00000759 | 1.74 | 0.3026 |
| Error | 4 | 0.00000436 | | |
| Corrected Total | 8 | 0.00001195 | | |
| | R-Square | C.V. | Valeric Acid Mean | |
| | 0.634854 | 14.34814 | 0.00727922 | |
| Source | DF | Type III SS | F Value | Pr > F |
| OTS | 2 | 0.00000514 | 2.35 | 0.2110 |
| WTS | 2 | 0.00000245 | 1.12 | 0.4100 |

Dependent Variable: Carpoic Acid

| Source | DF | Sum of Squares | F Value | Pr > F |
|---|---|---|---|---|
| Model | 4 | 0.00549122 | 24.47 | 0.0045 |
| Error | 4 | 1.00022444 | | |
| Corrected Total | 8 | 0.00571566 | | |
| | R-Square | C.V. | Carpoic Acid Mean | |
| | 0.960733 | 14.14015 | 0.05297414 | |
| Source | DF | Type III SS | F Value | Pr > F |
| OTS | 2 | 0.00535761 | 47.74 | 0.0016 |
| WTS | 2 | 0.00013362 | 1.19 | 0.3929 |

Dependent Variable: Heptanoic Acid

| Source | DF | Sum of Squares | F Value | Pr > F |
|---|---|---|---|---|
| Model | 4 | 0.00002350 | 1.18 | 0.4389 |
| Error | 4 | 0.00001995 | | |
| Corrected Total | 8 | 0.00004345 | | |
| | R-Square | C.V. | Heptanoic Acid Mean | |
| | 0.540824 | 37.64360 | 0.00593311 | |
| Source | DF | Type III SS | F Value | Pr > F |
| OTS | 2 | 0.00001419 | 1.42 | 0.3415 |
| WTS | 2 | 0.00000931 | 0.93 | 0.4650 |

Dependent Variable: Unknown

| Source | DF | Sum of Squares | F Value | Pr > F |
|---|---|---|---|---|
| Model | 4 | 0.00067175 | 2.14 | 0.2398 |
| Error | 4 | 0.00031410 | | |

APPENDIX B-continued

ANALYSES OF VARIANCE

| | | | | |
|---|---|---|---|---|
| Corrected Total | 8 | 0.00098584 | | |
| | R-Square | C.V. | | Unknown Mean |
| | 0.881391 | 47.30526 | | 0.01873242 |
| Source | DF | Type III SS | F Value | Pr > F |
| OTS | 2 | 0.00038344 | 2.44 | 0.2028 |
| WTS | 2 | 0.00028831 | 1.84 | 0.2719 |

Dependent Variable: Total VFA by GC

| Source | DF | Sum of Squares | F Value | Pr > F |
|---|---|---|---|---|
| Model | 4 | 0.01073467 | 30.26 | 0.0030 |
| Error | 4 | 0.00035475 | | |
| Corrected Total | 8 | 0.01108942 | | |
| | R-Square | C.V. | | Total VFA by GC Mean |
| | 0.968010 | 4.597065 | | 0.20485556 |
| Source | DF | Type III SS | F Value | Pr > F |
| OTS | 2 | 0.01070647 | 60.36 | 0.0010 |
| WTS | 2 | 0.00002820 | 0.16 | 0.8581 |

Dependent Variable: Total VFA by Titration

| Source | DF | Sum of Squares | F Value | Pr > F |
|---|---|---|---|---|
| Model | 4 | 0.44800000 | 7.00 | 0.0430 |
| Error | 4 | 0.06400000 | | |
| Corrected Total | 8 | 0.51200000 | | |
| | R-Square | C.V. | | Total VFA by Titration Mean |
| | 0.875000 | 10.78049 | | 1.17333333 |
| Source | DF | Type III SS | F Value | Pr > F |
| OTS | 2 | 0.35840000 | 11.20 | 0.0230 |
| WTS | 2 | 0.08960000 | 2.80 | 0.1736 |

Appendix B-3: The analyses of variance for the effects of oil IV and replication on the LSs and ITs of the soybean oils measured by the instrument
General Linear Models Procedure Dependent Variable: LS

| Source | DF | Sum of Squares | F Value | Pr > F |
|---|---|---|---|---|
| Model | 5 | 0.02317966 | 66.85 | 0.0001 |
| Error | 6 | 0.00041607 | | |
| Corrected Total | 11 | 0.02359573 | | |
| | R-Square | C.V. | | LS Mean |
| | 0.982367 | 5.067115 | | 0.16434167 |
| Source | DF | Type III SS | F Value | Pr > F |
| IV | 3 | 0.02297658 | 110.45 | 0.0001 |
| REPLICATION | 2 | 0.00020308 | 1.46 | 0.3035 |

Dependent Variable: IT

| Source | DF | Sum of Squares | F Value | Pr > F |
|---|---|---|---|---|
| Model | 5 | 1076.52935833 | 12.13 | 0.0043 |
| Error | 6 | 106.54173333 | | |
| Corrected Total | 11 | 1183.07109167 | | |
| | R-Square | C.V. | | INF Mean |
| | 0.909945 | 6.596674 | | 63.8791667 |
| Source | DF | Type III SS | F Value | Pr > F |
| IV | 3 | 1036.22489167 | 19.45 | 0.0017 |
| REPLICATION | 2 | 40.30446667 | 1.13 | 0.3819 |

Appendix B-4: The analyses of variance for the effects of IV and replication on the concentrations of VFA collected in DW during the instrument test

APPENDIX B-continued

ANALYSES OF VARIANCE

General Linear Models Procedure

Dependent Variable: Formic and Acetic Acid

| Source | DF | Sum of Squares | F Value | Pr > F |
|---|---|---|---|---|
| Model | 5 | 0.03695788 | 8.59 | 0.0104 |
| Error | 6 | 0.00516052 | | |
| Corrected Total | 11 | 0.04211841 | | |
| | R-Square | C.V. | Formic and Acetic Acid Mean | |
| | 0.877476 | 11.33311 | 0.25877500 | |
| Source | DF | Type III SS | F Value | Pr > F |
| IV | 3 | 0.03580770 | 13.88 | 0.0042 |
| REPLICATION | 2 | 0.00115019 | 0.67 | 0.5468 |

Dependent Variable: Propionic Acid

| Source | DF | Sum of Squares | F Value | Pr > F |
|---|---|---|---|---|
| Model | 5 | 0.00013658 | 12.16 | 0.0043 |
| Error | 6 | 0.00001348 | | |
| Corrected Total | 11 | 0.00015005 | | |
| | R-Square | C.V. | Propionic Acid Mean | |
| | 0.910196 | 8.400623 | 0.01783958 | |
| Source | DF | Type III SS | F Value | Pr > F |
| IV | 3 | 0.00013600 | 20.19 | 0.0015 |
| REPLICATION | 2 | 0.10000058 | 0.13 | 0.8818 |

Dependent Variable: Butyric Acid

| Source | DF | Sum of Squares | F Value | Pr > F |
|---|---|---|---|---|
| Model | 5 | 0.00064807 | 6.79 | 0.0186 |
| Error | 6 | 0.00011454 | | |
| Corrected Total | 11 | 0.00076261 | | |
| | R-Square | C.V. | Butyric Acid Mean | |
| | 0.849805 | 46.64894 | 0.00936614 | |
| Source | DF | Type III SS | F Value | Pr > F |
| IV | 3 | 0.00057397 | 10.02 | 0.0094 |
| REP | 2 | 0.00007409 | 1.94 | 0.2239 |

Dependent Variable: Valeric Acid

| Source | DF | Sum of Squares | F Value | Pr > F |
|---|---|---|---|---|
| Model | 5 | 0.00018925 | 63.30 | |
| Error | 6 | 0.00000359 | | |
| Corrected Total | 11 | 0.00019284 | | |
| | R-Square | C.V. | Valeric Acid Mean | |
| | 0.981395 | 7.564485 | 0.01022250 | |
| Source | DF | Type III SS | F Value | Pr > F |
| IV | 3 | 0.00018904 | 105.38 | |
| REPLICATION | 2 | 0.00000021 | 0.17 | 0.8444 |

Dependent Variable: Carpoic Acid

| Source | DF | Sum of Squares | F Value | Pr > F |
|---|---|---|---|---|
| Model | 5 | 0.00024532 | 5.41 | 0.0316 |
| Error | 6 | 0.00005443 | | |
| Corrected Total | 11 | 0.00029975 | | |
| | R-Square | C.V. | Carpoic Acid Mean | |
| | 0.818432 | 14.56082 | 0.02068417 | |
| Source | DF | Type III SS | F Value | Pr > F |
| IV | 3 | 0.00023273 | 8.55 | 0.0138 |
| REPLICATION | 2 | 0.00001260 | 0.69 | 0.5355 |

APPENDIX B-continued

ANALYSES OF VARIANCE

Dependent Variable: Heptanoic Acid

| Source | DF | Sum of Squares | F Value | Pr > F |
|---|---|---|---|---|
| Model | 5 | 0.00005206 | 112.26 | 0.0001 |
| Error | 6 | 0.00000056 | | |
| Corrected Total | 11 | 0.00005262 | | |
| | R-Square | C.V. | Heptanoic Acid Mean | |
| | 0.989424 | 25.37055 | 0.00120042 | |
| Source | DF | Type III SS | F Value | Pr > F |
| IV | 3 | 0.00005188 | 186.43 | |
| REPLICATION | 2 | 0.00000019 | 1.00 | 0.4219 |

Dependent Variable: Unknown

| Source | DF | Sum of Squares | F Value | Pr > F |
|---|---|---|---|---|
| Model | 5 | 1.24396326 | 121.26 | 0.0001 |
| Error | 6 | 0.01231007 | | |
| Corrected Total | 11 | 1.25627334 | | |
| | R-Square | C.V. | UNK Mean | |
| | 0.990201 | 18.40952 | 0.24604375 | |
| Source | DF | Type III SS | F Value | Pr > F |
| IV | 3 | 1.24073929 | 201.58 | 0.0001 |
| REPLICATION | 2 | 0.00322397 | 0.79 | 0.4977 |

Dependent Variable: Total VFA

| Source | DF | Sum of Squares | F Value | Pr > F |
|---|---|---|---|---|
| Model | 5 | 1.29037209 | 144.19 | 0.0001 |
| Error | 6 | 0.01073901 | | |
| Corrected Total | 11 | 1.30111110 | | |
| | R-Square | C.V. | Total VFA Mean | |
| | 0.991746 | 7.499366 | 0.56413352 | |
| Source | DF | Type III SS | F Value | Pr > F |
| IV | 3 | 1.28958322 | 240.17 | 0.0001 |
| REPLICATION | 2 | 0.00078887 | 0.22 | 0.8084 |

Appendix B-5: The analyses of variance for the effects of IV and replications on the TPC in the oils tested by the instrument
General Linear Models Procedure Dependent Variable: TPC

| Source | DF | Sum of Squares | Mean Square | F Value | Pr > F |
|---|---|---|---|---|---|
| Model | 9 | 0.0266104 | 0.0029567 | 31.81 | 0.0002 |
| Error | 6 | 0.0005576 | 0.0000929 | | |
| Corrected Total | 15 | 0.0271680 | | | |
| | R-Square | C.V. | Root MSE | TPC Mean | |
| | 0.979474 | 9.442901 | 0.0096 | 0.1021 | |
| Source | DF | Type III SS | Mean Square | F Value | Pr > F |
| IV | 3 | 0.0032127 | 0.0010709 | 11.52 | 0.0067 |
| TREATMENT | 1 | 0.0121524 | 0.0121524 | 130.75 | 0.0001 |
| REPLICATION | 2 | 0.0001387 | 0.0000694 | 0.75 | 0.5135 |
| IV*TREATMENT | 3 | 0.0013532 | 0.0004511 | 4.85 | 0.0480 |

Appendix B-6: The analyses of variance for the effects unsaturation level (IV) on the dielectric constant (FOS) of the soybean oils
General Linear Models Procedure Dependent Variable: FOS

| Source | DF | Sum of Squares | F Value | Pr > F |
|---|---|---|---|---|
| Model | 5 | 0.68166667 | 98.16 | 0.0001 |
| Error | 6 | 0.00833333 | | |
| Corrected Total | 11 | 0.69000000 | | |

APPENDIX B-continued

ANALYSES OF VARIANCE

| | R-Square | C.V. | | FOS Mean | |
|---|---|---|---|---|---|
| | 0.987923 | 2.981424 | | 1.25000000 | |
| Source | DF | Type III SS | F Value | Pr > F | |
| IV | 3 | 0.67666667 | 162.40 | 0.0001 | |
| REPLICATION | 2 | 0.0050000D | 1.80 | 0.2441 | |

Appendix B-7: The analyses of variance for the effects of unsaturation level (IV), treatment, and the interactions of IV and treatment on the free fatty acid content in the instrument tested oil
General Linear Models Procedure Dependent Variable: FFA

| Source | DF | Sum of Squares | Mean Square | F Value | Pr > F |
|---|---|---|---|---|---|
| Model | 9 | 0.0089050 | 0.0009894 | 25.67 | 0.0004 |
| Error | 6 | 0.0002313 | 0.0000385 | | |
| Corrected Total | 15 | 0.0091363 | | | |
| | R-Square | C.V. | Root MSE | FFA Mean | |
| | 0.974688 | 9.239452 | 0.0062 | 0.0672 | |
| Source | DF | Type III SS | Mean Square | F Value | Pr > F |
| IV | 3 | 0.0006717 | 0.0002239 | 5.81 | 0.0330 |
| TREATMENT | 1 | 0.0049380 | 0.0049380 | 128.12 | 0.0001 |
| IV*TREATMENT | 3 | 0.0004676 | 0.0001559 | 4.04 | 0.0687 |
| REPLICATION | 2 | 0.0000408 | 0.0000204 | 0.53 | 0.6141 |

Appendix B-8: The analyses of variance for the effects of unsaturation level (IV), treatment, and the interactions of IV and treatment on the dienoic acid contents in the instrument tested oils.
General Linear Models Procedure Dependent Variable: Dienoic Acid

| Source | DF | Sum of Square | Mean Square | F Value | Pr > F |
|---|---|---|---|---|---|
| Model | 7 | 0.1555386 | 0.0222198 | 71.00 | 0.0001 |
| Error | 8 | 0.0025036 | 0.0003129 | | |
| Corrected Total | 15 | 0.1580421 | | | |
| | R-Square | C.V. | Root MSE | Dienoic Acid Mean | |
| | 0.984159 | 6.831770 | 0.0177 | 0.2589 | |
| Source | DF | Type III SS | Mean Square | F Value | Pr > F |
| IV | 3 | 0.0126216 | 0.0042072 | 13.44 | 0.0017 |
| TREATMENT | 1 | 0.1337741 | 0.1337741 | 427.47 | 0.0001 |
| IV*TREATMENT | 3 | 0.0020297 | 0.0006766 | 2.16 | 0.1705 |

Appendix B-9: The analyses of variance for the effects of unsaturation level (IV), treatment, and the interactions of IV and treatment on the concentrations of tocopherols in the instrument tested oils
General Linear Models Procedure Dependent Variable: α-Tocopherol

| Source | DF | Sum of Squares | Mean Square | F Value | Pr > F |
|---|---|---|---|---|---|
| Model | 9 | 63.497653 | 7.055295 | 172.00 | 0.0001 |
| Error | 6 | 0.246111 | 0.041019 | | |
| Corrected Total | 15 | 63.743764 | | | |
| | R-Square | C.V. | Root MSE | α-Tocopherol Mean | |
| | 0.996139 | 7.094534 | 0.2025 | 2.8547 | |
| Source | DF | Type III SS | Mean Square | F Value | Pr > F |
| IV | 3 | 6.041036 | 2.013679 | 49.09 | 0.0001 |
| TREATMENT | 1 | 33.013094 | 33.013094 | 804.83 | 0.0001 |
| REPLICATION | 2 | 0.063526 | 0.031763 | 0.77 | 0.5022 |
| IV*TREATMENT | 3 | 1.421863 | 0.473954 | 11.55 | 0.0066 |

Dependent Variable: γ-Tocopherol

| Source | DF | Sum of Squares | Mean Square | F Value | Pr > F |
|---|---|---|---|---|---|

APPENDIX B-continued

ANALYSES OF VARIANCE

| | | | | | |
|---|---|---|---|---|---|
| Model | 9 | 4606.9835 | 511.8871 | 640.95 | 0.0001 |
| Error | 6 | 4.7918 | 0.7986 | | |
| Corrected Total | 15 | 4611.7753 | | | |
| | R-Square | C.V. | Root MSE | γ-Tocopherol Mean | |
| | 0.998961 | 6.749650 | 0.8937 | 13.240 | |
| Source | DF | Type III SS | Mean Square | F Value | Pr > F |
| IV | 3 | 704.1665 | 234.7222 | 293.90 | 0.0001 |
| TREATMENT | 1 | 2397.2913 | 2397.2913 | 3001.74 | 1.0001 |
| REPLICATION | 2 | 1.0616 | 0.5308 | 0.66 | 0.5486 |
| IV*TREATMENT | 3 | 348.6396 | 116.2132 | 145.51 | 0.0001 |

Dependent Variable: Δ-Tocopherol

| Source | DF | Sum of Squares | Mean Square | F Value | Pr > F |
|---|---|---|---|---|---|
| Model | 9 | 627.18309 | 69.68701 | 99.67 | 0.0001 |
| Error | 6 | 4.19490 | 0.69915 | | |
| Corrected Total | 15 | 631.37799 | | | |
| | R-Square | C.V. | Root MSE | Δ-Tocopherol Mean | |
| | 0.993356 | 9.488320 | 0.8362 | 8.8124 | |
| Source | DF | Type III SS | Mean Square | F Value | Pr > F |
| IV | 3 | 267.32330 | 89.10777 | 127.45 | 0.0001 |
| TREATMENT | 1 | 174.61217 | 174.61217 | 249.75 | 0.0001 |
| REPLICATION | 2 | 1.00371 | 0.50185 | 0.72 | 0.5254 |
| IV*TREATMENT | 3 | 34.04870 | 11.34957 | 16.23 | 0.0028 |

Dependent Variable: Total Tocopherols

| Source | DF | Sum of Squares | Mean Square | F Value | Pr > F |
|---|---|---|---|---|---|
| Model | 9 | 9566.9137 | 1062.9904 | 481.62 | 0.0001 |
| Error | 6 | 13.2426 | 2.2071 | | |
| Corrected Total | 15 | 9580.1563 | | | |
| | R-Square | C.V. | Root MSE | TOTAL Mean | |
| | 0.998618 | 5.966137 | 1.4856 | 24.901 | |
| Source | DF | Type III SS | Mean Square | F Value | Pr > F |
| IV | 3 | 1941.3337 | 647.1112 | 293.20 | 0.0001 |
| TREATMENT | 1 | 4608.5760 | 4608.5760 | 2088.07 | 0.0001 |
| REPLICATION | 2 | 2.6384 | 1.3192 | 0.60 | 0.5798 |
| IV*TREATMENT | 3 | 614.0372 | 204.6791 | 92.74 | 0.0001 |

Dependent Variable: Destruction

| Source | DF | Sum of Squares | Mean Square | F Value | Pr > F |
|---|---|---|---|---|---|
| Model | 5 | 0.2104521 | 0.0420904 | 91.61 | 0.0001 |
| Error | 6 | 0.0027568 | 0.0104595 | | |
| Corrected Total | 11 | 0.2132088 | | | |
| | R-Square | C.V. | Root MSE | Destruction Mean | |
| | 0.987070 | 2.679749 | 0.0214 | 0.7999 | |
| Source | DF | Type III SS | Mean Square | F Value | Pr > F |
| IV | 3 | 0.2100250 | 0.0700083 | 152.37 | 0.0001 |
| REPLICATION | 2 | 0.0004271 | 0.0002135 | 0.46 | 0.6491 |

Appendix B-10: The analyses of variance for the effects of replication, treatment (fresh vs instrument tested), unsaturation level (IV), and the interactions of treatment and IV on the concentrations of fatty acids in the soybean oils General Linear Models Procedure
FA = C16:0

Dependent Variable: CONC

| Source | DF | Sum of Squares | F Value | Pr > F |
|---|---|---|---|---|
| Model | 8 | 0.00090199 | 79.87 | 0.0001 |
| Error | 7 | 0.00000988 | | |
| Corrected Total | 15 | 0.00091187 | | |
| | R-Square | C.V. | CONC Mean | |

APPENDIX B-continued

ANALYSES OF VARIANCE

| Source | DF | Type III SS | F Value | Pr > F |
|---|---|---|---|---|
| | 0.989163 | 1.271158 | 0.09346875 | |
| TREATMENT | 1 | 0.00002424 | 17.17 | 0.0043 |
| IV | 3 | 0.00062780 | 148.24 | 0.0001 |
| TREAT*IV | 3 | 0.00000270 | 0.64 | 0.6149 |
| REPLICATION | 1 | 0.00000060 | 0.43 | 0.5336 |

FA = C18:0

Dependent Variable: CONC

| Source | DF | Sum of Squares | F Value | Pr > F |
|---|---|---|---|---|
| Model | 8 | 0.02088547 | 6569.73 | 0.0001 |
| Error | 7 | 0.00000278 | | |
| Corrected Total | 15 | 0.02088825 | | |
| R-Square | C.V. | | CONC Mean | |
| 0.999867 | 1.086280 | | 0.05803125 | |

| Source | DF | Type III SS | F Value | Pr > F |
|---|---|---|---|---|
| TREATMENT | 1 | 0.00000289 | 7.26 | 0.0309 |
| IV | 3 | 0.01578511 | 13241.0 | 0.0001 |
| TREAT*IV | 3 | 0.00000367 | 3.08 | 0.0998 |
| REPLICATION | 1 | 0.00000012 | 0.31 | 0.5924 |

FA = C18:1

Dependent Variable: CONC

| Source | DF | Sum of Squares | F Value | Pr > F |
|---|---|---|---|---|
| Model | 8 | 0.75886368 | 9235.72 | 0.0001 |
| Error | 7 | 0.00007190 | | |
| Corrected Total | 15 | 0.75893558 | | |
| R-Square | C.V. | | CONC Mean | |
| 0.999905 | 0.636126 | | 0.50380000 | |

| Source | DF | Type III SS | F Value | Pr > F |
|---|---|---|---|---|
| TREATMENT | 1 | 0.00001635 | 1.59 | 0.2475 |
| IV | 3 | 0.57086515 | 18527.2 | 0.0001 |
| TREATMENT*IV | 3 | 0.00012078 | 3.92 | 0.0622 |
| REPLICATION | 1 | 0.00000171 | 0.17 | 0.6953 |

FA = C18:2

Dependent Variable: CONC

| Source | DF | Sum of Squares | F Value | Pr > F |
|---|---|---|---|---|
| Model | 6 | 0.21916237 | 2604.36 | 0.0001 |
| Error | 5 | 0.00007013 | | |
| Corrected Total | 11 | 0.21923250 | | |
| R-Square | C.V. | | CONC Mean | |
| 0.999680 | 0.903254 | | 0.41461667 | |

| Source | DF | Type III SS | F Value | Pr > F |
|---|---|---|---|---|
| TREATMENT | 1 | 0.00010914 | 7.78 | 0.0385 |
| IV | 2 | 0.16241166 | 5789.94 | 0.0001 |
| TREATMENT*IV | 2 | 0.00006698 | 2.39 | 0.1871 |
| REPLICATION | 1 | 0.00000113 | 0.08 | 0.7882 |

FA = C18:3

Dependent Variable: CONC

| Source | DF | Sum of Squares | F Value | Pr > F |
|---|---|---|---|---|
| Model | 6 | 0.02187334 | 6463.75 | 0.0001 |
| Error | 5 | 0.00000282 | | |
| Corrected Total | 11 | 0.02187616 | | |
| R-Square | C.V. | | CONC Mean | |
| 0.999871 | 1.669506 | | 0.04498333 | |

APPENDIX B-continued

ANALYSES OF VARIANCE

| Source | DF | Type III SS | F Value | Pr > F |
|---|---|---|---|---|
| TREATMENT | 1 | 0.00000357 | 6.34 | 0.0534 |
| IV | 2 | 0.01649738 | 14625.3 | 0.0001 |
| TREATMENT*IV | 2 | 0.00000123 | 1.09 | 0.4048 |
| REPLICATION | 1 | 0.00000001 | 0.01 | 0.9177 |

Appendix B-11: The analyses of variance for the effects of additive treatment (ADD) and replication on the LSs and ITs of the soybean oil (IV = 94) measured by the instrument
General Linear Models Procedure Dependent Variable: LS

| Source | DF | Sum of Squares | F Value | Pr > F |
|---|---|---|---|---|
| Model | 5 | 0.02317966 | 66.85 | 0.0001 |
| Error | 6 | 0.00041607 | | |
| Corrected Total | 11 | 0.02359573 | | |
| | R-Square | C.V. | LS Mean | |
| | 0.982367 | 5.067115 | 0.16434167 | |
| Source | DF | Type III SS | F Value | Pr > F |
| ADD | 3 | 0.02297658 | 110.45 | 0.0001 |
| REPLICATION | 2 | 0.00020308 | 1.46 | 0.3035 |

Dependent Variable: IT

| Source | DF | Sum of Squares | F Value | Pr > F |
|---|---|---|---|---|
| Model | 5 | 1076.52935833 | 12.13 | 0.0043 |
| Error | 6 | 106.54173333 | | |
| Corrected Total | 11 | 1183.07109167 | | |
| | R-Square | C.V. | IT Mean | |
| | 0.909945 | 6.596674 | 63.8791667 | |
| Source | DF | Type III SS | F Value | Pr > F |
| ADD | 3 | 1036.22489167 | 19.45 | 0.0017 |
| REPLICATION | 2 | 40.30446667 | 1.13 | 0.3819 |

Appendix B-12: The analyses of variance for the effects of additive treatment (ADD) and replication on the concentrations of VFA collected in DW during the instrument test Dependent Variable: Acetic Acid

| Source | DF | Sum of Squares | F Value | Pr > F |
|---|---|---|---|---|
| Model | 5 | 0.03630723 | 237.13 | 0.0001 |
| Error | 6 | 0.00018373 | | |
| Corrected Total | 11 | 0.03649096 | | |
| | R-Square | C.V. | Acetic Acid Mean | |
| | 0.994965 | 2.637599 | 0.20980267 | |
| Source | DF | Type III SS | F Value | Pr > F |
| ADD | 3 | 0.03311716 | 360.49 | 0.0001 |
| REPLICATION | 2 | 0.00319007 | 52.09 | 0.0002 |

Dependent Variable: Propionic Acid

| Source | DF | Sum of Squares | F Value | Pr > F |
|---|---|---|---|---|
| Model | 5 | 0.00020848 | 100.37 | 0.0001 |
| Error | 6 | 0.00000249 | | |
| Corrected Total | 11 | 0.00021098 | | |
| | R-Square | C.V. | Propionic Acid Mean | |
| | 0.988186 | 4.371636 | 0.01474354 | |
| Source | DF | Type III SS | F Value | Pr > F |
| ADD | 3 | 0.00020451 | 164.10 | 0.0001 |
| REPLICATION | 2 | 0.00000397 | 4.78 | 0.0574 |

APPENDIX B-continued

ANALYSES OF VARIANCE

Dependent Variable: Butyric Acid

| Source | DF | Sum of Squares | F Value | Pr > F |
|---|---|---|---|---|
| Model | 5 | 0.00029149 | 6.99 | 0.0173 |
| Error | 6 | 0.00005002 | | |
| Corrected Total | 11 | 0.00034151 | | |
| R-Square | C.V. | | Butyric Acid Mean | |
| 0.853546 | 25.10360 | | 0.01150108 | |

| Source | DF | Type III SS | F Value | Pr > F |
|---|---|---|---|---|
| ADD | 3 | 0.00025921 | 10.37 | 0.0087 |
| REPLICATION | 2 | 0.00003228 | 1.94 | 0.2245 |

Dependent Variable: Valeric Acid

| Source | DF | Sum of Squares | F Value | Pr > F |
|---|---|---|---|---|
| Model | 5 | 0.00005326 | 9.56 | 0.0080 |
| Error | 6 | 0.00000668 | | |
| Corrected Total | 11 | 0.00005994 | | |
| R-Square | C.V. | | Valeric Acid Mean | |
| 0.888524 | 8.533733 | | 0.01236650 | |

| Source | DF | Type III SS | F Value | Pr > F |
|---|---|---|---|---|
| ADD | 3 | 0.00005020 | 15.03 | 0.0034 |
| REPLICATION | 2 | 0.00000306 | 1.37 | 0.3229 |

Dependent Variable: Caproic Acid

| Source | DF | Sum of Squares | F Value | Pr > F |
|---|---|---|---|---|
| Model | 5 | 0.00013785 | 68.32 | 0.0001 |
| Error | 6 | 0.00000242 | | |
| Corrected Total | 11 | 0.00014027 | | |
| R-Square | C.V. | | Caproic Acid Mean | |
| 0.982740 | 2.831900 | | 0.02243108 | |

| Source | DF | Type III SS | F Value | Pr > F |
|---|---|---|---|---|
| ADD | 3 | 0.00013293 | 109.81 | 0.0001 |
| REPLICATION | 2 | 0.00000492 | 6.09 | 0.0359 |

General Linear Models Procedure

Dependent Variable: Unknown

| Source | DF | Sum of Squares | F Value | Pr > F |
|---|---|---|---|---|
| Model | 5 | 0.00108316 | 3.73 | 0.0699 |
| Error | 6 | 0.00034810 | | |
| Corrected Total | 11 | 0.00143127 | | |
| R-Square | C.V. | | Unknown Mean | |
| 0.756786 | 24.86792 | | 0.03062946 | |

| Source | DF | Type III SS | F Value | Pr > F |
|---|---|---|---|---|
| ADD | 3 | 0.00107985 | 6.20 | 0.0286 |
| REPLICATION | 2 | 0.00000331 | 0.03 | 0.9720 |

Dependent Variable: Total VFA

| Source | DF | Sum of Squares | F Value | Pr > F |
|---|---|---|---|---|
| Model | 5 | 0.06653191 | 141.15 | 0.0001 |
| Error | 6 | 0.00056564 | | |
| Corrected Total | 11 | 0.06709755 | | |
| R-Square | C.V. | | Total VFA Mean | |
| 0.991570 | 3.220661 | | 0.30147450 | |

| Source | DF | Type III SS | F Value | Pr > F |
|---|---|---|---|---|
| ADD | 3 | 0.06226596 | 220.16 | 0.0001 |
| REPLICATION | 2 | 0.00426594 | 22.63 | 0.0016 |

APPENDIX B-continued

ANALYSES OF VARIANCE

Appendix B-13: The analyses of variance for the effects of additive treatment (ADD) and replications on the TPC in the oils tested by the instrument
General Linear Models Procedure Dependent Variable: TPC

| Source | DF | Sum of Squares | F Value | Pr > F |
|---|---|---|---|---|
| Model | 6 | 0.01519727 | 38.30 | 0.0001 |
| Error | 8 | 0.00052913 | | |
| Corrected Total | 14 | 0.01572639 | | |
| | R-Square | C.V. | TPC Mean | |
| | 0.966354 | 8.602988 | 0.09453333 | |
| Source | DF | Type III SS | F Value | Pr > F |
| ADD | 4 | 0.01509547 | 57.06 | 0.0001 |
| REPLICATION | 2 | 0.00010180 | 0.77 | 0.4947 |

Appendix B-14: The analyses of variance for the effects of additive treatment (ADD) and replication on the dielectric constant (FOS) of the soybean oils
General Linear Models Procedure Dependent Variable: FOS

| Source | DF | Sum of Squares | F Value | Pr > F |
|---|---|---|---|---|
| Model | 5 | 0.68166667 | 98.16 | 0.0001 |
| Error | 6 | 0.00833333 | | |
| Corrected Total | 11 | 0.69000000 | | |
| | R-Square | C.V. | FOS Mean | |
| | 0.987923 | 2.981424 | 1.25000000 | |
| Source | DF | Type III SS | F Value | Pr > F |
| ADD | 3 | 0.67666667 | 162.40 | 0.0001 |
| REPLICATION | 2 | 0.00500000 | 1.80 | 0.2441 |

Appendix B-15: The analyses of variance for the effects of additive treatment (ADD) and replication on the free fatty acid content (FFA) in the instrument tested oils
General Linear Models Procedure Dependent Variable: FFA

| Source | DF | Sum of Squares | F Value | Pr > F |
|---|---|---|---|---|
| Model | 6 | 0.00492981 | 86.29 | 0.0001 |
| Error | 8 | 0.00007618 | | |
| Corrected Total | 14 | 0.00500598 | | |
| | R-Square | C.V. | FFA Mean | |
| | 0.984783 | 5.123475 | 0.06022893 | |
| Source | DF | Type III SS | F Value | Pr > F |
| ADD | 4 | 0.00478833 | 125.71 | 0.0001 |
| REPLICATION | 2 | 0.00014147 | 7.43 | 0.0150 |

Appendix B-16: The ananlyses of variance for the effects of replication and additive treatment (ADD) on the dienoic acid contents in the instrument tested oils
General Linear Models Procedure Dependent Variable: Dienoic Acid

| Source | DF | Sum of Squares | F Value | Pr > F |
|---|---|---|---|---|
| Model | 6 | 0.13965235 | 32.76 | 0.0001 |
| Error | 8 | 0.00568348 | | |
| Corrected Total | 14 | 0.14533583 | | |
| | R-Square | C.V. | Dienoic acid Mean | |
| | 0.960894 | 11.17286 | 0.23856000 | |
| Source | DF | Type III SS | F Value | Pr > F |
| ADD | 4 | 0.13847844 | 48.73 | 0.0001 |
| REPLICATION | 2 | 0.00117391 | 0.83 | 0.4719 |

Appendix B-17: The analyses of variance for the effects of additive treatment (ADD)

APPENDIX B-continued

ANALYSES OF VARIANCE and replication on the concentrations of tocopherols in the instrument tested oil
General Linear Models Procedure Dependent Variable: α-Tocopherol

| Source | DF | Sum of Squares | F Value | Pr > F |
|---|---|---|---|---|
| Model | 6 | 59.35407582 | 703.75 | 0.0001 |
| Error | 8 | 0.11245313 | | |
| Corrected Total | 14 | 59.46652895 | | |
| | R-Square | C.V. | α-Tocopherol Mean | |
| | 0.998109 | 4.430807 | 2.67582667 | |
| Source | DF | Type III SS | F Value | Pr > F |
| ADD | 4 | 59.15262788 | 1052.04 | 0.0001 |
| REPLICATION | 2 | 0.20144794 | 7.17 | 0.0165 |

Dependent Variable: γ-Tocopherol

| Source | DF | Sum of Squares | F Value | Pr > F |
|---|---|---|---|---|
| Model | 6 | 4478.61501810 | 2603.80 | 0.0001 |
| Error | 8 | 2.29337593 | | |
| Corrected Total | 14 | 4480.90839403 | | |
| | R-Square | C.V. | γ-Tocopherol Mean | |
| | 0.999488 | 3.987736 | 13.4266067 | |
| Source | DF | Type III SS | F Value | Pr > F |
| ADD | 4 | 4478.36295610 | 3905.48 | 0.0001 |
| REPLICATION | 2 | 0.25206200 | 0.44 | 0.6589 |

Dependent Variable: Δ-Tocopherol

| Source | DF | Sum of Squares | F Value | Pr > F |
|---|---|---|---|---|
| Model | 6 | 338.73448437 | 472.74 | 0.0001 |
| Error | 8 | 0.95537926 | | |
| Corrected Total | 14 | 339.68986363 | | |
| | R-Square | C.V. | Δ-Tocopherol Mean | |
| | 0.997187 | 3.555145 | 9.72043333 | |
| Source | DF | Type III SS | F Value | Pr > F |
| ADD | 4 | 337.98598984 | 707.54 | 0.0001 |
| REPLICATION | 2 | 0.74849453 | 3.13 | 0.0988 |

Dependent Variable: Total Tocopherols

| Source | DF | Sum of Squares | F Value | Pr > F |
|---|---|---|---|---|
| Model | 6 | 8409.22456422 | 2249.44 | 0.0001 |
| Error | 8 | 4.98447647 | | |
| Corrected Total | 14 | 8414.20904069 | | |
| | R-Square | C.V. | Total Tocopherols Mean | |
| | 0.999408 | 3.056753 | 25.8228667 | |
| Source | DF | Type III SS | F Value | Pr > F |
| ADD | 4 | 8406.55272037 | 3373.09 | 0.0001 |
| REPLICATION | 2 | 2.67184386 | 2.14 | 0.1796 |

Dependent Variable: Destruction

| Source | DF | Sum of Squares | F Value | Pr > F |
|---|---|---|---|---|
| Model | 5 | 0.04884468 | 97.83 | 0.0001 |
| Error | 6 | 0.00059914 | | |
| Corrected Total | 11 | 0.04944382 | | |
| | R-Square | C.V. | Destruction Mean | |
| | 0.987882 | 1.238466 | 0.80687418 | |
| Source | DF | Type III SS | F Value | Pr > F |
| ADD | 3 | 0.04804685 | 160.38 | 0.0001 |
| REPLICATION | 2 | 0.00079783 | 3.99 | 0.0789 |

APPENDIX B-continued

ANALYSES OF VARIANCE

Appendix 18: The analyses of variance for the effects of additive treatment (ADD) and replication on the concentrations of fatty acids in soybean oil (IV = 94) tested by the Instrument
General Linear Models Procedure
FA = C16:0

Dependent Variable: CONC

| Source | DF | Sum of Squares | F Value | Pr > F |
|---|---|---|---|---|
| Model | 6 | 0.00007649 | 24.62 | 0.0001 |
| Error | 8 | 0.00000414 | | |
| Corrected Total | 14 | 0.00008064 | | |
| | R-Square | C.V. | CONC Mean | |
| | 0.948626 | 0.822846 | 0.08745333 | |
| Source | DF | Type III SS | F Value | Pr > F |
| ADD | 4 | 0.00007558 | 36.49 | 0.0001 |
| REPLICATION | 2 | 0.00000092 | 0.89 | 0.4493 |

FA = C18:0

Dependent Variable: CONC

| Source | DF | Sum of Squares | F Value | Pr > F |
|---|---|---|---|---|
| Model | 6 | 0.00000903 | 10.37 | 0.0021 |
| Error | 8 | 0.00000116 | | |
| Corrected Total | 14 | 0.00001019 | | |
| | R-Square | C.V. | CONC Mean | |
| | 0.886069 | 1.034409 | 0.03683333 | |
| Source | DF | Type III SS | F Value | Pr > F |
| ADD | 4 | 0.00000791 | 13.62 | 0.0012 |
| REPLICATION | 2 | 0.00000113 | 3.88 | 0.0665 |

FA = C18:1

Dependent Variable: CONC

| Source | DF | Sum of Squares | F Value | Pr > F |
|---|---|---|---|---|
| Model | 6 | 0.00039467 | 5.38 | 0.0166 |
| Error | 8 | 0.00009784 | | |
| Corrected Total | 14 | 0.00049252 | | |
| | R-Square | C.V. | CONC Mean | |
| | 0.801341 | 0.562738 | 0.62146000 | |
| Source | DF | Type III SS | F Value | Pr > F |
| ADD | 4 | 0.00039455 | 8.06 | 0.0066 |
| REPLICATION | 2 | 0.00000012 | 0.01 | 0.9949 |

FA = C18:2

Dependent Variable: CONC

| Source | DF | Sum of Squares | F Value | Pr > F |
|---|---|---|---|---|
| Model | 6 | 0.00054080 | 9.63 | 0.0027 |
| Error | 8 | 0.00007487 | | |
| Corrected Total | 14 | 0.00061567 | | |
| | R-Square | C.V. | CONC Mean | |
| | 0.878400 | 1.234641 | 0.24777333 | |
| Source | DF | Type III SS | F Value | Pr > F |
| ADD | 4 | 0.00053804 | 14.37 | 0.0010 |
| REPLICATION | 2 | 0.00000276 | 0.15 | 0.8651 |

FA = C18:3

Dependent Variable: CONC

APPENDIX B-continued

ANALYSES OF VARIANCE

| Source | DF | Sum of Squares | F Value | Pr > F |
|---|---|---|---|---|
| Model | 6 | 0.00001391 | 1.11 | 0.4346 |
| Error | 8 | 0.00001677 | | |
| Corrected Total | 14 | 0.00003069 | | |
| | R-Square | C.V. | | CONC Mean |
| | 0.453404 | 22.25478 | | 0.00650667 |
| Source | DF | Type III SS | F Value | Pr > F |
| ADD | 4 | 0.00000495 | 0.59 | 0.6795 |
| REPLICATION | 2 | 0.00000897 | 2.14 | 0.1804 |

RATIO

Dependent Variable: RATIO

| Source | DF | Sum of Squares | F Value | Pr > F |
|---|---|---|---|---|
| Model | 6 | 0.25508920 | 20.67 | 0.0002 |
| Error | 8 | 0.01645373 | | |
| Corrected Total | 14 | 0.27154293 | | |
| | R-Square | C.V. | | RATIO Mean |
| | 0.939407 | 1.598706 | | 2.83673333 |
| Source | DF | Type III SS | F Value | Pr > F |
| ADD | 4 | 0.25466627 | 30.96 | 0.0001 |
| REPLICATION | 2 | 0.00042293 | 0.10 | 0.9035 |

APPENDIX C

Statistical Analyses of the Accuracy of the Instrument

Appendix C-1: The regression between the ln(OSI) and induction time (IT) of soybean oils (with IVs of 70, 94, 110, and 132, and treated with DMS, TBHQ, and BOTH)
Analysis of Variance Dependent Variable: LOG(OSI)

| Source | DF | Sum of Squares | Mean Square | F Value | P > F |
|---|---|---|---|---|---|
| Model | 1 | 27.44597 | 27.44597 | 373.896 | 0.0001 |
| Error | 16 | 1.17449 | 0.07341 | | |
| C Total | 17 | 28.62046 | | | |
| | Root MSE | 0.27093 | R-square | 0.9590 | |
| | Dep Mean | 3.26135 | Adj R-sq | 0.9564 | |
| | C.V. | 8.30742 | | | |

Parameter Estimates

| Variable | DF | Parameter Estimate | Standard Error | T for H0 parameter = 0 |
|---|---|---|---|---|
| INTERCEPT | 1 | −0.112606 | 0.18580638 | −0.606 |
| IT | 1 | 0.055988 | 0.00289550 | 19.336 |

| Variable | DF | P > |T| |
|---|---|---|
| INTERCEPT | 1 | 0.5530 |
| IT | 1 | 0.0001 |

Appendix C-2: The regression between 1/(OSI) and linear slope (LS) of the soybean oils (with IVs of 70, 94, 110, and 132, and treated with DMS, TBHQ, and BOTH)
Analysis of Variance Dependent Variable: 1/OSI

| Source | DF | Sum of Squares | Mean Square | F Value | P > F |
|---|---|---|---|---|---|
| Model | 1 | 0.05840 | 0.05840 | 141.499 | 0.0001 |

APPENDIX C-continued

| Statistical Analyses of the Accuracy of the Instrument | | | | |
|---|---|---|---|---|
| Error | 16 | 0.00660 | 0.00041 | |
| C Total | 17 | 0.06500 | | |
| | Root MSE | 0.02032 | R-square | 0.8984 |
| | Dep Mean | 0.06847 | Adj R-sq | 0.8921 |
| | C.V. | 29.66984 | | |

| Parameter Estimates | | | | |
|---|---|---|---|---|
| Variable | DF | Parameter Estimate | Standard Error | T for H0: parameter = 0 |
| INTERCEPT | 1 | −0.033468 | 0.00981684 | −3.409 |
| LS | 1 | 0.441746 | 0.03713609 | 11.895 |

| Variable | DF | P > \|T\| |
|---|---|---|
| INTERCEPT | 1 | 0.0036 |
| LS | 1 | 0.0001 |

What is claimed is:

1. A method of determining a stability of an oil or fat comprising:
   heating an oil or a fat;
   contacting the oil or fat with a moisturized gas;
   contacting the moisturized gas with water to form a trap solution;
   measuring the electrical conductivity of the trap solution; and
   determining the stability of the oil or fat.

2. The method according to claim 1, wherein the stability of the oil or fat is determined by the change in conductivity of the trap solution with respect to time.

3. The method according to claim 1, wherein the gas comprises air.

4. The method according to claim 1, wherein the gas comprises oxygen.

5. The method according to claim 1, wherein the water is deionized water.

6. The method according to claim 5, wherein the deionized water is high performance liquid chromatography grade deionized water.

7. The method according to claim 1, wherein the oil or fat is heated to a temperature between about 100° C. and 220° C.

8. The method according to claim 1, wherein the oil or fat is heated to a temperature between about 150° C. and 160° C.

9. The method according to claim 1, wherein the oil or fat is heated to a temperature of about 160° C.

10. The method according to claim 1, wherein the moisturized gas is at a temperature between about 40° C. and 60° C.

11. The method according to claim 1, wherein the moisturized gas is at a temperature of about 50° C.

12. The method according to claim 1, wherein the electrical conductivity of the trap solution is determined at a temperature below about 20° C.

13. The method according to claim 1, wherein the electrical conductivity of the trap solution is determined by a probe having a sensitivity between 0 and 300 $\mu$S/cm.

14. The method according to claim 1, wherein the electrical conductivity of the trap solution is determined by a probe having a sensitivity between 0 to 22 $\mu$S/cm conductivity and a linear response to the conductivity between 0 and 11 $\mu$S/cm.

15. The method according to claim 1, wherein the moisturized gas has a flow rate of about 200 mL/min.

16. The method according to claim 1, wherein the weight of the trap solution is measured to detect weight change due to moisture condensation from the moisturized gas.

17. The method according to claim 16, wherein the conductivity of the trap solution is adjusted proportionally by the weight change of the trap solution.

18. The method according to claim 1, wherein the stability of the oil or fat is determined by a rate of conductivity change between measured conductivities of 4.0 and 11.0 $\mu$S/cm.

19. The method according to claim 1, wherein the stability of the oil or fat is determined by a period of time for the conductivity of the trap solution to reach an equivalent acetic acid concentration of about 0.2 mM as determined by the following equation:

$$\text{acetic acid concentration} = e^{(\text{conductivity of the trap solution} - 15.56)/2.442}.$$

20. The method according to claim 1, wherein the stability of the oil or fat is determined by a period of time for the conductivity of the trap solution to reach 4 $\mu$S/cm.

21. An instrument for measurement of stability of oils and fats comprising:
   a sample reaction vessel for containing a sample of an oil or fat;
   a moisturized gas source operably connected to the vessel for contacting a moisturized gas with the sample;
   a compound trap containing water operably connected to the vessel to contact the moisturized gas from the vessel with the water; and
   an automatic data acquisition and control system for monitoring the electrical conductivity of the water.

22. The instrument according to claim 21, wherein the sample reaction vessel has a heat source for heating the sample and a temperature sensor to monitor the temperature of the sample.

23. The instrument according to claim 21, wherein the sample reaction vessel is maintained at a temperature between about 100° C. and 220° C.

24. The instrument according to claim 21, wherein the sample reaction vessel is maintained at a temperature between about 150° C. and 160° C.

25. The instrument according to claim 21, wherein the sample reaction vessel is maintained at a temperature of about 160° C.

26. The instrument according to claim 21, wherein the moisturized gas source comprises a gas source, a gas regulating device to control gas flow rate, and a moisture supplier to provide moisture to the gas.

27. The instrument according to claim 21, wherein the moisturized gas is maintained at a flow rate of about 200 mL/min.

28. The instrument according to claim 21, wherein the moisturized gas source is maintained at a temperature between about 40° C. and 60° C.

29. The instrument according to claim 21, wherein the moisturized gas source is maintained at a temperature of about 50° C.

30. The instrument according to claim 21, wherein the gas comprises oxygen.

31. The instrument according to claim 21, wherein the gas comprises air.

32. The instrument according to claim 21, wherein the compound trap comprises a container to hold the water, a temperature sensor to monitor the temperature of the water, and a cooling device to maintain the compound trap at a desired temperature.

33. The instrument according to claim 32, wherein the compound trap further comprises a weight measuring device to measure the weight of the water.

34. The instrument according to claim 21, wherein the compound trap is maintained at a temperature below about 20° C.

35. The instrument according to claim 21, wherein the automatic data acquisition and control system comprises a conductivity probe having a sensitivity between 0 to 22 $\mu$S/cm conductivity and a linear response to the conductivity between 0 and 11 $\mu$S/cm operably disposed in the compound trap.

36. The instrument according to claim 22, wherein the automatic data acquisition and control system further comprises a computer to record and control temperatures of the sample reaction vessel, the moisturized air source, and the compound trap, to record and control moisturized gas flow rate, to record water weight with respect to time, and to record the electrical conductivity of the water with respect to time.

37. The instrument according to claim 21, wherein the water is deionized water.

38. The instrument according to claim 21, wherein the deionized water is high performance liquid chromatography grade deionized water.

39. A quality control instrument utilized in the manufacturing of oils or fats comprising the instrument of claim 21.

* * * * *